United States Patent
Lindsley et al.

(10) Patent No.: US 11,851,406 B2
(45) Date of Patent: Dec. 26, 2023

(54) POSITIVE ALLOSTERIC MODULATORS OF THE MUSCARINIC ACETYLCHOLINE RECEPTOR M₁

(71) Applicant: Vanderbilt University, Nashville, TN (US)

(72) Inventors: Craig W. Lindsley, Brentwood, TN (US); P. Jeffrey Conn, Nashville, TN (US); Darren W. Engers, Brentwood, TN (US); Julie L. Engers, Brentwood, TN (US); Aaron M. Bender, Spring Hill, TN (US); Madeline Long, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 555 days.

(21) Appl. No.: 17/251,649

(22) PCT Filed: Jun. 13, 2019

(86) PCT No.: PCT/US2019/036893
§ 371 (c)(1),
(2) Date: Dec. 11, 2020

(87) PCT Pub. No.: WO2019/241467
PCT Pub. Date: Dec. 19, 2019

(65) Prior Publication Data
US 2021/0261526 A1    Aug. 26, 2021

Related U.S. Application Data

(60) Provisional application No. 62/684,472, filed on Jun. 13, 2018.

(51) Int. Cl.
*C07D 401/14* (2006.01)
*C07D 405/14* (2006.01)
*C07D 413/14* (2006.01)

(52) U.S. Cl.
CPC ......... *C07D 401/14* (2013.01); *C07D 405/14* (2013.01); *C07D 413/14* (2013.01)

(58) Field of Classification Search
None
See application file for complete search history.

(56) References Cited

U.S. PATENT DOCUMENTS

| 2013/0090352 A1 | 4/2013 | Gilbert et al. |
| 2016/0016907 A1 | 7/2016 | Lindsley et al. |
| 2017/0121308 A1 | 5/2017 | Ogino et al. |

FOREIGN PATENT DOCUMENTS

| WO |   0183472 A1 | 11/2001 | |
| WO |   2017143041 A1 | 8/2017 | |
| WO | WO-2017143041 A1 * | 8/2017 | ......... A61K 31/4365 |
| WO |   2018063552 A1 | 4/2018 | |

OTHER PUBLICATIONS

Ciapetti et al., "Molecular variations based on isosteric replacements," in The practice of medicinal chemistry, Academic Press, 2008, pp. 290-342.

Davoren et al., "Design and optimization of selective azaindole amide M1 positive allosteric modulators," Bioorg Med Chem Lett., 2016, vol. 26, No. 2, pp. 650-655.

Engers et al., "VU6007477, a Novel M1 PAM Based on a Pyrrolo[2,3-b]pyridine Carboxamide Core Devoid of Cholinergic Adverse Events," ACS Med. Chem. Lett., 2018, vol. 9, pp. 917-922.

PubCHEM SID 112354745, 'N-(2-Hydroxycydohexyl)-6-pyraizol-1-ylpyridine-2-carboxamide', U.S. National Library of Medicine, Jan. 20, 2016, <https://pubcllem.ncbi.nlm.nih.gov/compound/112354745>.

Rook et al., "Diverse Effects on M1 Signaling and Adverse Effect Liability within a Series of M1 Ago-PAMs," ACS Chem Neurosci., 2017, vol. 8, No. 4, pp. 866-883.

International Search Report and Written Opinion for Application No. PCT/US2019/036893 dated Sep. 10, 2019 (12 pages).

International Preliminary Report on Patentability for Application No. PCT/US2019/036893 dated Dec. 24, 2020 (5 pages).

* cited by examiner

*Primary Examiner* — Traviss C McIntosh, III
(74) *Attorney, Agent, or Firm* — Michael Best & Friedrich LLP

(57) ABSTRACT

Described are positive allosteric modulators of muscarinic acetylcholine receptor $M_1$ (mAChR $M_1$), pharmaceutical compositions including the compounds, and methods of using the compounds and compositions for treating neurological disorders, psychiatric disorders, or a combination thereof.

20 Claims, No Drawings

POSITIVE ALLOSTERIC MODULATORS OF THE MUSCARINIC ACETYLCHOLINE RECEPTOR $M_1$

RELATED APPLICATIONS

This patent application is the U.S. national stage entry, under 35 U.S.C. § 371, of International Application Number PCT/US2019/036893, filed Jun. 13, 2019, which claims priority to U.S. Provisional Application No. 62/684,472, filed Jun. 13, 2018, the entire contents of each of which are hereby incorporated by reference.

STATEMENT OF GOVERNMENT INTEREST

This invention was made with government support under Grant number MH106839 awarded by the National Institutes of Health. The government has certain rights in the invention.

TECHNICAL FIELD

The present disclosure relates to compounds, compositions, and methods for treating muscarinic acetylcholine receptor $M_1$ related diseases and/or disorders, such as neurological and psychiatric disorders.

BACKGROUND

Positive allosteric modulators are compounds that bind to a site distinct from that of the orthosteric agonist binding site of a target protein. These modulators enhance the affinity or efficacy of an orthosteric agonist. For example, a selective muscarinic $M_1$ positive allosteric modulator would result in an increased affinity at the orthosteric binding site for acetylcholine (ACh), the endogenous agonist for the muscarinic $M_1$ receptor, or an increase in the efficacy induced by ACh. In some systems, the compound may also have an intrinsic activity to activate the receptor in the absence of orthosteric ligand. Positive allosteric modulation (potentiation), therefore, can be an attractive mechanism for enhancing appropriate physiological receptor activation.

Cholinergic neurotransmission involves the activation of nicotinic acetylcholine receptors (nAChRs) or the muscarinic acetylcholine receptors (mAChRs) by the binding of the endogenous orthosteric agonist ACh. Acetylcholinesterase (AChE) inhibitors, which inhibit the hydrolysis of ACh, have been approved in the United States for use in the palliative, but not disease-modifying, treatment of the cognitive deficits in Alzheimer's disease (AD) patients.

mAChRs are members of the family A GPCRs, and include five subtypes, designated $M_1$, $M_2$, $M_3$, $M_4$, and $M_5$. $M_1$, $M_3$ and $M_5$ mainly couple to Gq and activate phospholipase C, whereas $M_2$ and $M_4$ mainly couple to $G_{i/o}$ and associated effector systems. These five distinct mAChR subtypes have been identified in the mammalian central nervous system where they are prevalent and differentially expressed. $M_1$-$M_5$ mAChRs have varying roles in cognitive, sensory, motor and autonomic functions. Activation of various muscarinic receptors, particularly the $M_1$ subtype, has been proposed as a mechanism to enhance cognition in disorders such as AD and schizophrenia (as well as negative symptoms). Thus, selective positive allosteric modulators of mAChR subtypes that regulate processes involved in cognitive function could prove superior to AChE inhibitors for treatment of AD and related disorders as these compounds may exhibit improved selectivity for specific mAChRs.

Efforts to create selective $M_1$ agonists have been largely unsuccessful, in part due to the high conservation of the orthosteric ACh binding site. As a result, mAChR agonists in clinical studies induce the same adverse effects of AChE inhibitors by activation of peripheral mAChRs. To fully understand the physiological roles of individual mAChR subtypes and to further explore the therapeutic utility of mACh receptors in AD, schizophrenia and other disorders, there exists a need to develop compounds that are highly selective modulators of $M_1$ and other individual mAChR subtypes. Accordingly, allosteric modulation may be an advantageous pathway because allosteric sites on mAChRs are less highly conserved.

Despite advances in muscarinic receptor (mAChR) research, there remains a scarcity of compounds that are potent, efficacious and selective positive allosteric modulators of the $M_1$ mAChR that are also effective in the treatment of neurological and psychiatric disorders associated with cholinergic activity, or other neurologic diseases in which the muscarinic $M_1$ receptor may be involved.

SUMMARY

In one aspect, disclosed are compounds of formula (I), or pharmaceutically acceptable salts thereof,

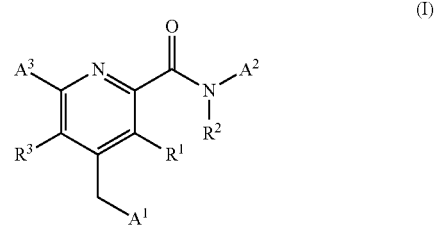

(I)

wherein
$A^1$ is $Cyc^1$ or -$Cyc^2$-$Cyc^3$;
$Cyc^1$ is a 6- to 12-membered aryl or 5- to 12-membered heteroaryl;
$Cyc^2$ is a 6- to 12-membered aryl, 5- to 12-membered heteroaryl, or 4- to 12-membered heterocycle;
$Cyc^3$ is a 6- to 12-membered aryl or 5- to 12-membered heteroaryl;
wherein $Cyc^1$, $Cyc^2$, and $Cyc^3$ are each independently optionally substituted with 1-5 substituents independently selected from the group consisting of halogen, $C_{1-4}$alkyl, $C_{1-4}$haloalkyl, —$OC_{1-4}$alkyl, —$OC_{1-4}$haloalkyl, OH, oxo, cyano, $C_{3-6}$cycloalkyl, and —$C_{1-3}$alkylene-$C_{3-6}$cycloalkyl, wherein each cycloalkyl is optionally substituted with 1-4 substituents independently selected from halogen and $C_{1-4}$alkyl;
$A^2$ is $C_{1-6}$alkyl, $C_{1-6}$haloalkyl, or -$L^1$-$G^1$, wherein the $C_{1-6}$alkyl and $C_{1-6}$haloalkyl are optionally substituted with 1-2 substituents independently selected from cyano, oxo, OH, —$OC_{1-4}$alkyl, and $C_{3-6}$cycloalkyl;
$L^1$ is a bond, $C_{2-6}$alkenylene, or $C_{1-6}$alkylene, wherein the $C_{2-6}$alkenylene and $C_{1-6}$alkylene are optionally substituted with 1-4 substituents independently selected from the group consisting of halogen, cyano, OH, oxo, and —$OC_{1-4}$alkyl;
$G^1$ is $C_{3-12}$cycloalkyl or 4- to 12-membered heterocycle, wherein $G^1$ is optionally substituted with 1-4 substituents independently selected from the group consisting of $C_{1-4}$alkyl, $C_{1-4}$haloalkyl, OH, —$OC_{1-4}$alkyl, cyano, oxo, and $C_{3-6}$cycloalkyl;

$A^3$ is a 5-membered heteroaryl containing 1-3 heteroatoms independently selected from O, N, and S, the heteroaryl being optionally substituted with 1-4 substituents independently selected from the group consisting of halogen, $C_{1-4}$alkyl, $C_{1-4}$haloalkyl, —$OC_{1-4}$alkyl, —$OC_{1-4}$haloalkyl, cyano, $C_{3-6}$cycloalkyl, and —$C_{1-3}$alkylene-$C_{3-6}$cycloalkyl, wherein each cycloalkyl is optionally substituted with 1-4 substituents independently selected from halogen and $C_{1-4}$alkyl;

$R^1$ and $R^3$ are independently hydrogen, halogen, cyano, $C_{1-4}$alkyl, $C_{1-4}$haloalkyl, —$OC_{1-4}$alkyl, or —$C_{1-3}$alkylene-$OC_{1-4}$alkyl; and $R^2$ is hydrogen, $C_{1-6}$alkyl, or $C_{1-6}$haloalkyl.

In another aspect, the invention provides a pharmaceutical composition comprising a compound of formula (I), or a pharmaceutically acceptable salt thereof, and a pharmaceutically acceptable carrier.

In another aspect, the invention provides a method for the treatment of a disorder associated with muscarinic acetylcholine receptor activity in a mammal, comprising administering to the mammal an effective amount of a compound of formula (I), or a pharmaceutically acceptable salt or composition thereof.

In another aspect, the invention provides a compound of formula (I), or a pharmaceutically acceptable salt or composition thereof, for use in the treatment of a disorder associated with muscarinic acetylcholine receptor activity.

In another aspect, the invention provides the use of a compound of formula (I), or a pharmaceutically acceptable salt or composition thereof, in the manufacture of a medicament for the treatment of a disorder associated with muscarinic acetylcholine receptor activity.

In another aspect, the invention provides a kit comprising a compound of formula (I), or a pharmaceutically acceptable salt or composition thereof, and instructions for use.

Also disclosed are methods of making the compounds, and methods of using the compounds for treatment of $M_1$ muscarinic acetylcholine receptor related diseases and/or disorders.

In another aspect, the invention provides a compound of formula (I), or a pharmaceutically acceptable salt or composition thereof, with minimal to substantially no $M_1$ agonist activity compared to acetylcholine. The relative absence of $M_1$ agonist activity is expected to avoid or reduce cholinergic adverse effect liability at therapeutic concentrations and/or doses.

DETAILED DESCRIPTION

Disclosed herein are positive allosteric modulators of the $M_1$ muscarinic acetylcholine receptor $M_1$ (mAChR $M_1$). The modulators can have the structure of formula (I). Compounds of formula (I) exhibit high affinity for mAChR $M_1$, and can also exhibit selectivity over other muscarinic acetylcholine receptors. Compounds of formula (I) can be used to treat or prevent diseases and disorders associated with mAChR $M_1$ by modulating mAChR $M_1$ activity. mAChR $M_1$ has been implicated in a number of different diseases and disorders including, but not limited to, neurological and psychiatric disorders.

Since the orthosteric binding sites of the mAChR isoforms are highly conserved, selective modulators of the mAChRs that bind at the orthosteric site remain elusive. One strategy to selectively bind and modulate the mAChRs includes identifying allosteric sites which may be amenable to modulation by a small molecule. In particular, positive allosteric modulation of mAChR $M_1$ can result in potentiation of the mAChR $M_1$ receptor and provide therapeutic benefits for disorders associated with mAChR $M_1$ dysfunction.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis,* 3$^{rd}$ Edition, Cambridge University Press, Cambridge, 1987; the entire contents of each of which are incorporated herein by reference.

The term "alkyl," as used herein, means a straight or branched, saturated hydrocarbon chain. The term "lower alkyl" or "$C_{1-6}$alkyl" means a straight or branched chain hydrocarbon containing from 1 to 6 carbon atoms. The term "$C_{1-4}$alkyl" means a straight or branched chain saturated hydrocarbon containing from 1 to 4 carbon atoms. Representative examples of alkyl include, but are not limited to, methyl, ethyl, n-propyl, iso-propyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkenyl," as used herein, means a straight or branched, hydrocarbon chain containing at least one carbon-carbon double bond.

The term "alkylene," as used herein, refers to a divalent group derived from a straight or branched saturated chain hydrocarbon, for example, of 1 to 6 carbon atoms. Representative examples of alkylene include, but are not limited to, —CH$_2$CH$_2$—, —CH$_2$CH$_2$CH$_2$—, —CH$_2$CH$_2$CH$_2$CH$_2$—, and —CH$_2$CH$_2$CH$_2$CH$_2$CH$_2$—.

The term "alkenylene," as used herein, refers to a divalent group derived from a straight or branched chain hydrocarbon having at least one carbon-carbon double bond The term "aryl," as used herein, refers to a phenyl or a phenyl appended to the parent molecular moiety and fused to a cycloalkyl group (e.g., indanyl), a phenyl group (i.e., naphthyl), or a non-aromatic heterocycle (e.g., benzo[d][1,3]dioxol-5-yl).

The term "cycloalkyl," as used herein, refers to a carbocyclic ring system containing zero heteroatoms and zero double bonds. Representative examples of cycloalkyl include, but are not limited to, cyclopropyl, cyclobutyl, cyclopentyl, cyclohexyl, cycloheptyl, cyclooctyl, cyclononyl, cyclodecyl, adamantyl, and bicyclo[1.1.1]pentanyl.

The term "cycloalkenyl," as used herein, means a non-aromatic monocyclic or multicyclic all-carbon ring system containing at least one carbon-carbon double bond and preferably having from 5-10 carbon atoms per ring. Exemplary monocyclic cycloalkenyl rings include cyclopentenyl, cyclohexenyl or cycloheptenyl.

The term "halogen" or "halo," as used herein, means Cl, Br, I, or F.

The term "haloalkyl," as used herein, means an alkyl group, as defined herein, in which one, two, three, four, five, six, seven or eight hydrogen atoms are replaced by a halogen.

The term "heteroaryl," as used herein, refers to an aromatic monocyclic heteroatom-containing ring (monocyclic heteroaryl) or a bicyclic ring system containing at least one monocyclic heteroaryl (bicyclic heteroaryl). The monocyclic heteroaryl are five or six membered rings containing at least one heteroatom independently selected from the group consisting of N, O and S (e.g. 1, 2, 3, or 4 heteroatoms independently selected from O, S, and N). The five membered aromatic monocyclic rings have two double bonds and the six membered six membered aromatic monocyclic rings have three double bonds. The bicyclic heteroaryl is an 8- to 12-membered ring system having a monocyclic heteroaryl ring fused to a monocyclic aromatic, saturated, or partially saturated carbocyclic ring, a monocyclic heteroaryl, or a monocyclic heterocycle. The bicyclic heteroaryl group includes a 9-membered fused bicyclic aromatic ring system having four double bonds and at least one heteroatom contributing a lone electron pair to a fully aromatic 10π electron system, such as ring systems with a nitrogen atom at the ring junction (e.g., imidazopyridine) or a benzoxadiazolyl. The bicyclic heteroaryl is attached to the parent molecular moiety at an aromatic ring atom. Representative examples of heteroaryl include, but are not limited to, indolyl (e.g., indol-1-yl, indol-2-yl, indol-4-yl), pyridinyl (including pyridin-2-yl, pyridin-3-yl, pyridin-4-yl), pyrimidinyl, pyrazinyl, pyridazinyl, pyrazolyl (e.g., pyrazol-4-yl), pyrrolyl, benzopyrazolyl, 1,2,3-triazolyl (e.g., triazol-4-yl), 1,3,4-thiadiazolyl, 1,2,4-thiadiazolyl, 1,3,4-oxadiazolyl, 1,2,4-oxadiazolyl, imidazolyl, thiazolyl (e.g., thiazol-4-yl), isothiazolyl, thienyl, benzimidazolyl (e.g., benzimidazol-5-yl), benzothiazolyl, benzoxazolyl, benzoxadiazolyl, benzothienyl, benzofuranyl, isobenzofuranyl, furanyl, oxazolyl, isoxazolyl, purinyl, isoindolyl, quinoxalinyl, indazolyl (e.g., indazol-4-yl, indazol-5-yl), quinazolinyl, 1,2,4-triazinyl, 1,3,5-triazinyl, isoquinolinyl, quinolinyl, 6,7-dihydro-1,3-benzothiazolyl, imidazo[1,2-a]pyridinyl (e.g., imidazo[1,2-a]pyridin-6-yl), naphthyridinyl, pyridoimidazolyl, thiazolo[5,4-b]pyridin-2-yl, and thiazolo[5,4-d]pyrimidin-2-yl.

The term "heterocycle" or "heterocyclic," as used herein, means a monocyclic heterocycle, a bicyclic heterocycle, or a tricyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, 2-oxo-3-piperidinyl, 2-oxoazepan-3-yl, oxadiazolinyl, oxadiazolidinyl, oxazolinyl, oxazolidinyl, oxetanyl, oxepanyl, oxocanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, a monocyclic heterocycle fused to a monocyclic heteroaryl, or a spiro heterocycle group, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. The bicyclic heterocycle is attached to the parent molecular moiety at a non-aromatic ring atom (e.g., 2-oxaspiro[3.3]heptan-6-yl, indolin-1-yl, hexahydrocyclopenta[b]pyrrol-1(2H)-yl). Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, 2-azaspiro[3.3]heptan-2-yl, 2-oxa-6-azaspiro[3.3]heptan-6-yl, azabicyclo[2.2.1]heptyl (including 2-azabicyclo[2.2.1]hept-2-yl), azabicyclo[3.1.0]hexanyl (including 3-azabicyclo[3.1.0]hexan-3-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but are not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1 3,7]decane), and oxa-adamantane (2-oxatricyclo[3.3.1.1 3,7]decane). The monocyclic, bicyclic, and tricyclic heterocycles are connected to the parent molecular moiety at a non-aromatic ring atom.

The term "hydroxyl" or "hydroxy," as used herein, means an —OH group.

Terms such as "alkyl," "cycloalkyl," "alkylene," etc. may be preceded by a designation indicating the number of atoms present in the group in a particular instance (e.g., "$C_{1-4}$alkyl," "$C_{3-6}$cycloalkyl," "$C_{1-4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1-4}$," the members of the group that follows may have any number of carbon atoms falling within the recited range. A "$C_{1-4}$alkyl," for example, is an alkyl group having from 1 to 4 carbon atoms, however arranged (i.e., straight chain or branched).

The term "substituted" refers to a group that may be further substituted with one or more non-hydrogen substituent groups. Substituent groups may include, for example, halogen, =O (oxo), =S (thioxo), cyano, nitro, fluoroalkyl, alkoxyfluoroalkyl, fluoroalkoxy, alkyl, alkenyl, alkynyl, haloalkyl, haloalkoxy, heteroalkyl, cycloalkyl, cycloalkenyl, aryl, heteroaryl, heterocycle, cycloalkylalkyl, heteroarylalkyl, arylalkyl, hydroxy, hydroxyalkyl, alkoxy, alkoxyalkyl, alkylene, aryloxy, phenoxy, benzyloxy, amino, alkylamino, acylamino, aminoalkyl, arylamino, sulfonylamino, sulfinylamino, sulfonyl, alkylsulfonyl, arylsulfonyl, aminosulfonyl, sulfinyl, —COOH, ketone, amide, carbamate, and acyl.

For compounds described herein, groups and substituents thereof may be selected in accordance with permitted valence of the atoms and the substituents, such that the selections and substitutions result in a stable compound, e.g., which does not spontaneously undergo transformation such as by rearrangement, cyclization, elimination, etc.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. Compounds

A first aspect of the invention provides compounds of formula (I), wherein $R^1$, $R^2$, $R^3$, $A^1$, $A^2$, and $A^3$ are as defined herein. The embodiments of formula (I) provided herein include any combinations of the variables $R^1$, $R^2$, $R^3$, $A^1$, $A^2$, and $A^3$, as these variables are described herein, including with sub-variables such as $Cyc^2$, $Cyc^3$, $R^6$, etc.

In some embodiments, $A^3$ is a 5-membered heteroaryl containing two nitrogen atoms and optionally substituted as defined herein, wherein $R^1$, $R^2$, $R^3$, $A^1$, and $A^2$ are as defined herein. In further embodiments, $A^3$ is optionally substituted pyrazolyl. In still further embodiments, $A^3$ is optionally substituted pyrazol-1-yl, pyrazol-3-yl, or pyrazol-4-yl. In yet further embodiments, $A^3$ is optionally substituted with $C_{1-4}$alkyl (e.g., pyrazolyl optionally substituted with $C_{1-4}$alkyl). In exemplary embodiments, $A^3$ is

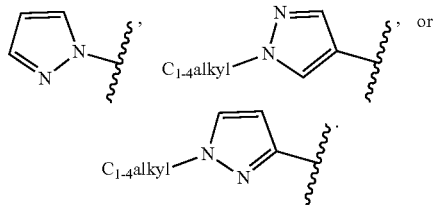

In some embodiments, $A^1$ is -$Cyc^2$-$Cyc^3$, wherein $Cyc^2$, $Cyc^3$, $R^1$, $R^2$, $R^3$, $A^2$, and $A^3$ are as defined herein.

In some embodiments, $Cyc^2$ is an optionally substituted 6- to 12-membered aryl. In some embodiments, $Cyc^2$ is an optionally substituted phenyl. In other embodiments, $Cyc^2$ is an optionally substituted 5- to 12-membered heteroaryl. In still further embodiments, $Cyc^2$ is an optionally substituted pyridinyl. In yet further embodiments, $Cyc^2$ is

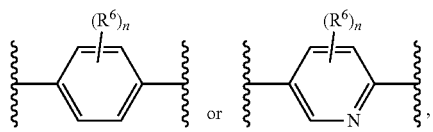

wherein -$Cyc^2$-$Cyc^3$ is

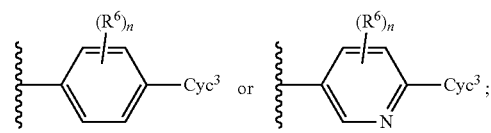

$R^6$, at each occurrence, is independently selected from the group consisting of halogen, $C_{1-4}$alkyl, $C_{1-4}$haloalkyl, —O$C_{1-4}$alkyl, —O$C_{1-4}$haloalkyl, OH, cyano, $C_{3-6}$cycloalkyl, and —$C_{1-3}$alkylene-$C_{3-6}$cycloalkyl; and n is 0, 1, 2, 3, or 4. In some of these embodiments, n is 0.

In some embodiments, $Cyc^3$ is an optionally substituted 5- to 12-membered heteroaryl. In some embodiments, $Cyc^3$ is an optionally substituted 5- to 6-membered monocyclic heteroaryl. In further embodiments, $Cyc^3$ is an optionally substituted 5-membered monocyclic heteroaryl containing two heteroatoms independently selected from O and N. In still further embodiments, $Cyc^3$ is an optionally substituted pyrazolyl or oxazolyl. In yet further embodiments, $Cyc^3$ is optionally substituted with $C_{1-4}$alkyl. In exemplary embodiments, $Cyc^3$ is

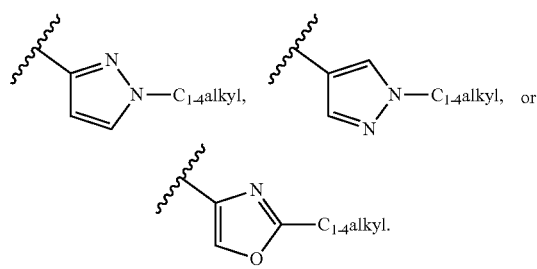

In the compounds described herein, Cyc³ may be

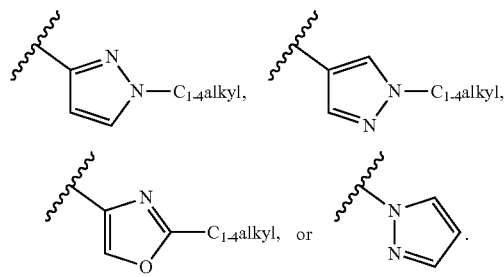

In some embodiments, Cyc³ may be

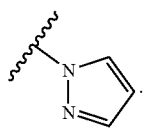 [SMILES: *n1cccn1]

In the compounds described herein, -Cyc²-Cyc³ may be

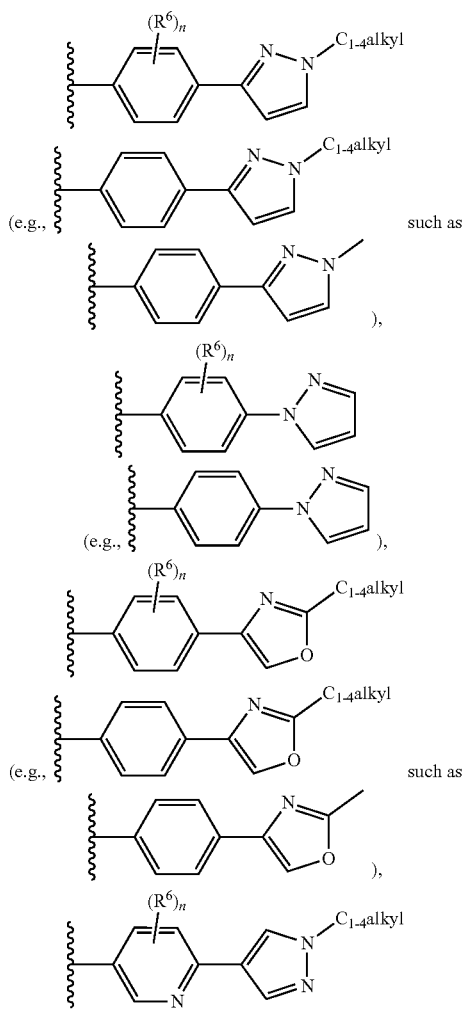

(e.g.,

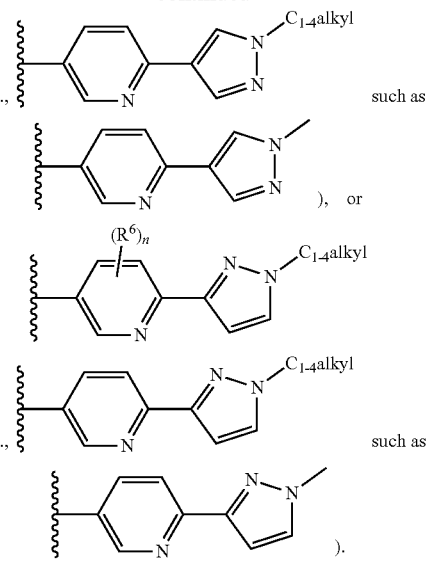

such as

), or (e.g., such as

).

In some embodiments, A¹ is Cyc¹. Cyc¹ may be a 5- to 6-membered optionally substituted heteroaryl. The 5- to 6-membered heteroaryl may contain 1-3 nitrogen ring atoms. The 5- to 6-membered heteroaryl may be a 6-membered heteroaryl containing 1-2 nitrogen ring atoms. The 6-membered heteroaryl may be a pyridyl. The Cyc¹ described herein may be substituted with 0-3 $C_{1-4}$alkyl groups. For example, Cyc¹ may be

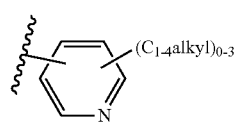

such as

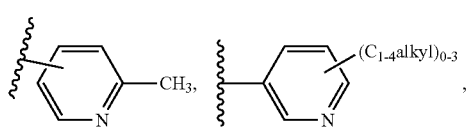

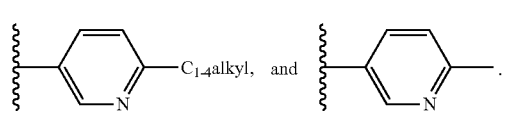

In some embodiments, A² is -L¹-G¹, wherein L¹, G¹, R¹, R², R³, A¹, and A³ are as defined herein. In some embodiments, G¹ is an optionally substituted $C_{3-12}$cycloalkyl or an optionally substituted 4- to 12-membered heterocycle containing one oxygen atom. In further embodiments, G¹ is a monocyclic $C_{3-8}$cycloalkyl, a monocyclic 4- to 8-membered heterocycle containing one oxygen atom, or a 7- to 12-membered spirocyclic heterocycle containing one oxygen atom, wherein G¹ is optionally substituted with 1-2 substituents selected from OH and $C_{1-4}$alkyl. In still further embodiments, G¹ is

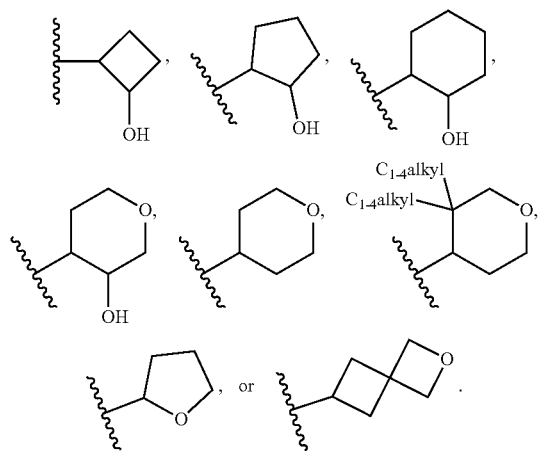

In still further embodiments, $G^1$ is

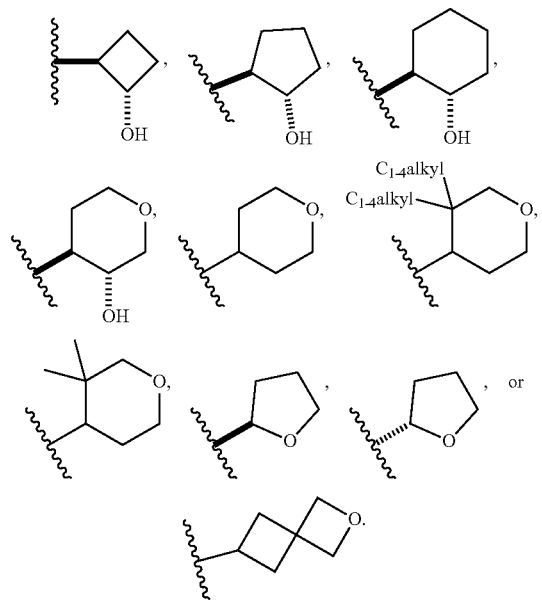

According to any of the embodiments herein $L^1$ may be a bond. Further according to any of the embodiments herein $L^1$ maybe $CH_2$.

In the compounds described herein, $A^2$ may be -$L^1$-$G^1$, wherein -$L^1$-$G^1$ is

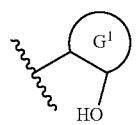

(i.e., $L^1$ is a bond) and $G^1$ is a 4- to 6-membered saturated alicyclic ring optionally having one carbon ring atom replaced by oxygen. In

$G^1$ is substituted with OH on the carbon atom adjacent to the position of attachment to the parent molecular moiety, but $G^1$ has no other non-hydrogen substituents. An alicyclic ring refers to a non-aromatic ring composed of carbon atoms. In the case of

one carbon ring atom of the alicyclic ring is optionally replaced by oxygen. For example, $A^2$ may be where $X^1$ is O or $CH_2$ (i.e., $G^1$ is tetrahydropyranyl or cyclohexyl).

In any of the embodiments herein, $R^1$ may be hydrogen, wherein $R^2$, $R^3$, $A^1$, $A^2$, and $A^3$ are as defined herein.

In any of the embodiments herein, $R^2$ may be hydrogen, wherein $R^1$, $R^3$, $A^1$, $A^2$, and $A^3$ are as defined herein.

In any of the embodiments herein, $R^3$ may be hydrogen or $C_{1-4}$alkyl (e.g., methyl), wherein $R^1$, $R^2$, $A^1$, $A^2$, and $A^3$ are as defined herein.

In some embodiments, $R^1$, $R^2$, and $R^3$ are hydrogen. In other embodiments, $R^1$ and $R^2$ are hydrogen, and $R^3$ is $C_{1-4}$alkyl (e.g., methyl).

In an exemplary combination, $R^1$ and $R^2$ are hydrogen; $R^3$ is hydrogen or $C_{1-4}$alkyl; $A^1$ is -$Cyc^2$-$Cyc^3$; $Cyc^2$ is an optionally substituted 6- to 12-membered aryl or an optionally substituted 5- to 12-membered heteroaryl; $Cyc^3$ is an optionally substituted 5- to 12-membered heteroaryl; $A^2$ is $L^1$-$G^1$; $G^1$ is an optionally substituted $C_{3-12}$cycloalkyl or an optionally substituted 4- to 12-membered heterocycle containing one oxygen atom; $A^3$ is an optionally substituted 5-membered heteroaryl; and $L^1$ is as defined herein. In a further exemplary combination, $Cyc^2$ is an optionally substituted phenyl or pyridinyl; $Cyc^3$ is an optionally substituted 5-membered monocyclic heteroaryl containing two heteroatoms independently selected from O and N; $G^1$ is a monocyclic $C_{3-8}$cycloalkyl, a monocyclic 4- to 8-membered heterocycle containing one oxygen atom, or a 7- to 12-membered spirocyclic heterocycle containing one oxygen atom, wherein $G^1$ is optionally substituted with 1-2 substituents selected from OH and $C_{1-4}$alkyl; $L^1$ is a bond or $CH_2$; and $A^3$ is an optionally substituted pyrazolyl. In a further exemplary combination, $Cyc^2$ is or

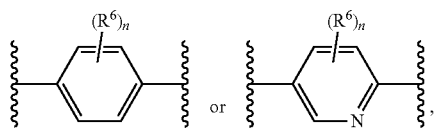

wherein -Cyc²-Cyc³ is

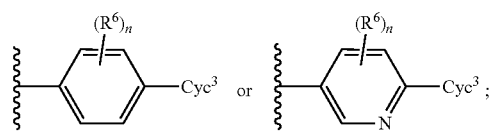

n is 0; Cyc³ is pyrazolyl or oxazolyl, each optionally substituted with C₁₋₄alkyl; G¹ is

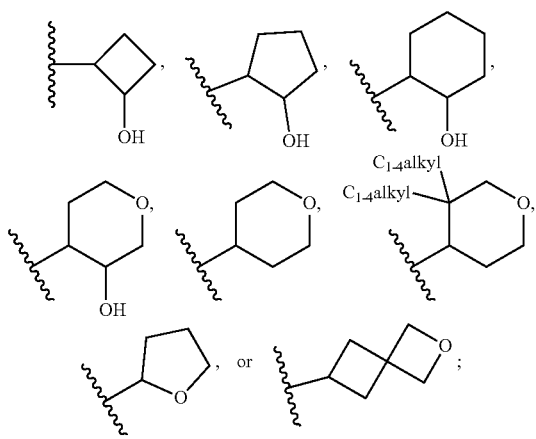

L¹ is a bond or CH₂; and A³ is pyrazolyl optionally substituted with C₁₋₄alkyl.

Representative compounds of formula (I) include, but are not limited to:

N-((3R,4S)-3-hydroxytetrahydro-2H-pyran-4-yl)-4-(4-(1-methyl-1H-pyrazol-3-yl)benzyl)-6-(1H-pyrazol-1-yl)picolinamide;
N-((1S,2S)-2-hydroxycyclohexyl)-4-(4-(1-methyl-1H-pyrazol-3-yl)benzyl)-6-(1H-pyrazol-1-yl)picolinamide;
4-(4-(1-methyl-1H-pyrazol-3-yl)benzyl)-6-(1H-pyrazol-1-yl)-N-(tetrahydro-2H-pyran-4-yl)picolinamide;
4-(4-(1-methyl-1H-pyrazol-3-yl)benzyl)-6-(1H-pyrazol-1-yl)-N-(2-oxaspiro[3.3]heptan-6-yl)picolinamide;
N-((1S,2S)-2-hydroxycyclobutyl)-4-(4-(1-methyl-1H-pyrazol-3-yl)benzyl)-6-(1H-pyrazol-1-yl)picolinamide;
N-((1S,2S)-2-hydroxycyclopentyl)-4-(4-(1-methyl-1H-pyrazol-3-yl)benzyl)-6-(1H-pyrazol-1-yl)picolinamide;
N-((1S,2S)-2-hydroxycyclohexyl)-6-(1-methyl-1H-pyrazol-3-yl)-4-(4-(1-methyl-1H-pyrazol-3-yl)benzyl)picolinamide;
6-(1-methyl-1H-pyrazol-3-yl)-4-(4-(1-methyl-1H-pyrazol-3-yl)benzyl)-N-(tetrahydro-2H-pyran-4-yl)picolinamide;
6-(1-methyl-1H-pyrazol-3-yl)-4-(4-(1-methyl-1H-pyrazol-3-yl)benzyl)-N-(2-oxaspiro[3.3]heptan-6-yl)picolinamide;
N-((3R,4S)-3-hydroxytetrahydro-2H-pyran-4-yl)-6-(1-methyl-1H-pyrazol-3-yl)-4-(4-(1-methyl-1H-pyrazol-3-yl)benzyl)picolinamide;
N-((1S,2S)-2-hydroxycyclopentyl)-6-(1-methyl-1H-pyrazol-3-yl)-4-(4-(1-methyl-1H-pyrazol-3-yl)benzyl)picolinamide;
N-((3R,4S)-3-hydroxytetrahydro-2H-pyran-4-yl)-4-(4-(1-methyl-1H-pyrazol-3-yl)benzyl)-6-(1-methyl-1H-pyrazol-4-yl)picolinamide;
N-((1S,2S)-2-hydroxycyclohexyl)-4-(4-(1-methyl-1H-pyrazol-3-yl)benzyl)-6-(1-methyl-1H-pyrazol-4-yl)picolinamide;
N-((1S,2S)-2-hydroxycyclohexyl)-6-(1-methyl-1H-pyrazol-3-yl)-4-((6-(1-methyl-1H-pyrazol-4-yl)pyridin-3-yl)methyl)picolinamide;
6-(1-methyl-1H-pyrazol-3-yl)-4-((6-(1-methyl-1H-pyrazol-4-yl)pyridin-3-yl)methyl)-N-(tetrahydro-2H-pyran-4-yl)picolinamide;
6-(1-methyl-1H-pyrazol-3-yl)-4-((6-(1-methyl-1H-pyrazol-4-yl)pyridin-3-yl)methyl)-N-(2-oxaspiro[3.3]heptan-6-yl)picolinamide;
N-((1S,2S)-2-hydroxycyclopentyl)-6-(1-methyl-1H-pyrazol-3-yl)-4-((6-(1-methyl-1H-pyrazol-4-yl)pyridin-3-yl)methyl)picolinamide;
(S)-6-(1-methyl-1H-pyrazol-3-yl)-4-((6-(1-methyl-1H-pyrazol-4-yl)pyridin-3-yl)methyl)-N-((tetrahydrofuran-2-yl)methyl)picolinamide;
N-(3,3-dimethyltetrahydro-2H-pyran-4-yl)-6-(1-methyl-1H-pyrazol-3-yl)-4-((6-(1-methyl-1H-pyrazol-4-yl)pyridin-3-yl)methyl)picolinamide;
N-((3R,4S)-3-hydroxytetrahydro-2H-pyran-4-yl)-5-methyl-6-(1-methyl-H-pyrazol-3-yl)-4-(4-(1-methyl-1H-pyrazol-3-yl)benzyl)picolinamide;
N-((1S,2S)-2-hydroxycyclohexyl)-5-methyl-6-(1-methyl-1H-pyrazol-3-yl)-4-(4-(1-methyl-1H-pyrazol-3-yl)benzyl)picolinamide;
5-methyl-6-(1-methyl-1H-pyrazol-3-yl)-4-(4-(1-methyl-1H-pyrazol-3-yl)benzyl)-N-(tetrahydro-2H-pyran-4-yl)picolinamide;
5-methyl-6-(1-methyl-1H-pyrazol-3-yl)-4-(4-(1-methyl-1H-pyrazol-3-yl)benzyl)-N-(2-oxaspiro[3.3]heptan-6-yl)picolinamide;
N-((1S,2S)-2-hydroxycyclopentyl)-5-methyl-6-(1-methyl-1H-pyrazol-3-yl)-4-(4-(1-methyl-1H-pyrazol-3-yl)benzyl)picolinamide;
N-((1S,2S)-2-hydroxycyclobutyl)-5-methyl-6-(1-methyl-1H-pyrazol-3-yl)-4-(4-(1-methyl-1H-pyrazol-3-yl)benzyl)picolinamide;
5-methyl-6-(1-methyl-1H-pyrazol-3-yl)-4-(4-(1-methyl-1H-pyrazol-3-yl)benzyl)-N-((tetrahydro-2H-pyran-4-yl)methyl)picolinamide;
(S)-5-methyl-6-(1-methyl-1H-pyrazol-3-yl)-4-(4-(1-methyl-1H-pyrazol-3-yl)benzyl)-N-((tetrahydrofuran-2-yl)methyl)picolinamide;
(R)-5-methyl-6-(1-methyl-1H-pyrazol-3-yl)-4-(4-(1-methyl-1H-pyrazol-3-yl)benzyl)-N-((tetrahydrofuran-2-yl)methyl)picolinamide;
N-(3,3-dimethyltetrahydro-2H-pyran-4-yl)-5-methyl-6-(1-methyl-1H-pyrazol-3-yl)-4-(4-(1-methyl-1H-pyrazol-3-yl)benzyl)picolinamide;
N-((3R,4S)-3-hydroxytetrahydro-2H-pyran-4-yl)-4-((6-(1-methyl-1H-pyrazol-4-yl)pyridin-3-yl)methyl)-6-(1H-pyrazol-1-yl)picolinamide;
N-((3R,4S)-3-hydroxytetrahydro-2H-pyran-4-yl)-4-(4-(2-methyloxazol-4-yl)benzyl)-6-(1H-pyrazol-1-yl)picolinamide;
N-((1S,2S)-2-hydroxycyclohexyl)-4-((6-(1-methyl-1H-pyrazol-4-yl)pyridin-3-yl)methyl)-6-(1H-pyrazol-1-yl)picolinamide;

4-((6-(1-methyl-1H-pyrazol-4-yl)pyridin-3-yl)methyl)-6-(1H-pyrazol-1-yl)-N-(2-oxaspiro[3.3]heptan-6-yl)picolinamide;

N-((1S,2S)-2-hydroxycyclohexyl)-4-(4-(2-methyloxazol-4-yl)benzyl)-6-(1H-pyrazol-1-yl)picolinamide;

4-(4-(2-methyloxazol-4-yl)benzyl)-6-(1H-pyrazol-1-yl)-N-(2-oxaspiro[3.3]heptan-6-yl)picolinamide;

N-((1S,2S)-2-hydroxycyclopentyl)-4-(4-(2-methyloxazol-4-yl)benzyl)-6-(1H-pyrazol-1-yl)picolinamide;

N-((1S,2S)-2-hydroxycyclobutyl)-4-(4-(2-methyloxazol-4-yl)benzyl)-6-(1H-pyrazol-1-yl)picolinamide;

4-((6-(1-methyl-1H-pyrazol-4-yl)pyridin-3-yl)methyl)-6-(1H-pyrazol-1-yl)-N-(tetrahydro-2H-pyran-4-yl)picolinamide;

4-(4-(2-methyloxazol-4-yl)benzyl)-6-(1H-pyrazol-1-yl)-N-(tetrahydro-2H-pyran-4-yl)picolinamide;

N-((3R,4S)-3-hydroxytetrahydro-2H-pyran-4-yl)-5-methyl-4-(4-(1-methyl-1H-pyrazol-3-yl)benzyl)-6-(1H-pyrazol-1-yl)picolinamide;

N-((1S,2S)-2-hydroxycyclohexyl)-5-methyl-4-(4-(1-methyl-1H-pyrazol-3-yl)benzyl)-6-(1H-pyrazol-1-yl)picolinamide;

5-methyl-4-(4-(1-methyl-1H-pyrazol-3-yl)benzyl)-6-(1H-pyrazol-1-yl)-N-(tetrahydro-2H-pyran-4-yl)picolinamide;

N-((1S,2S)-2-hydroxycyclopentyl)-5-methyl-4-(4-(1-methyl-1H-pyrazol-3-yl)benzyl)-6-(1H-pyrazol-1-yl)picolinamide;

N-((3R,4S)-3-hydroxytetrahydro-2H-pyran-4-yl)-5-methyl-4-((6-(1-methyl-1H-pyrazol-3-yl)pyridin-3-yl)methyl)-6-(1H-pyrazol-1-yl)picolinamide;

N-((3R,4S)-3-hydroxytetrahydro-2H-pyran-4-yl)-5-methyl-4-(4-(2-methyloxazol-4-yl)benzyl)-6-(1H-pyrazol-1-yl)picolinamide;

N-((1S,2S)-2-hydroxycyclohexyl)-5-methyl-4-((6-(1-methyl-1H-pyrazol-3-yl)pyridin-3-yl)methyl)-6-(1H-pyrazol-1-yl)picolinamide;

N-((1S,2S)-2-hydroxycyclohexyl)-5-methyl-4-((6-(1-methyl-1H-pyrazol-4-yl)pyridin-3-yl)methyl)-6-(1H-pyrazol-1-yl)picolinamide;

N-((1S,2S)-2-hydroxycyclohexyl)-5-methyl-4-(4-(2-methyloxazol-4-yl)benzyl)-6-(1H-pyrazol-1-yl)picolinamide;

5-methyl-4-((6-(1-methyl-1H-pyrazol-3-yl)pyridin-3-yl)methyl)-6-(1H-pyrazol-1-yl)-N-(tetrahydro-2H-pyran-4-yl)picolinamide;

5-methyl-4-((6-(1-methyl-1H-pyrazol-4-yl)pyridin-3-yl)methyl)-6-(1H-pyrazol-1-yl)-N-(tetrahydro-2H-pyran-4-yl)picolinamide;

5-methyl-4-(4-(2-methyloxazol-4-yl)benzyl)-6-(1H-pyrazol-1-yl)-N-(tetrahydro-2H-pyran-4-yl)picolinamide;

N-((1S,2S)-2-hydroxycyclopentyl)-5-methyl-4-((6-(1-methyl-1H-pyrazol-3-yl)pyridin-3-yl)methyl)-6-(1H-pyrazol-1-yl)picolinamide;

N-((1S,2S)-2-hydroxycyclopentyl)-5-methyl-4-((6-(1-methyl-1H-pyrazol-4-yl)pyridin-3-yl)methyl)-6-(1H-pyrazol-1-yl)picolinamide;

N-((1S,2S)-2-hydroxycyclopentyl)-5-methyl-4-(4-(2-methyloxazol-4-yl)benzyl)-6-(1H-pyrazol-1-yl)picolinamide;

4-(4-(1H-pyrazol-1-yl)benzyl)-N-((3R,4S)-3-hydroxytetrahydro-2H-pyran-4-yl)-5-methyl-6-(1-methyl-1H-pyrazol-3-yl)picolinamide;

4-(4-(1H-pyrazol-1-yl)benzyl)-N-((1S,2S)-2-hydroxycyclohexyl)-5-methyl-6-(1-methyl-1H-pyrazol-3-yl)picolinamide;

4-(4-(1H-pyrazol-1-yl)benzyl)-5-methyl-6-(1-methyl-1H-pyrazol-3-yl)-N-(tetrahydro-2H-pyran-4-yl)picolinamide;

4-(4-(1H-pyrazol-1-yl)benzyl)-5-methyl-6-(1-methyl-1H-pyrazol-3-yl)-N-(2-oxaspiro[3.3]heptan-6-yl)picolinamide;

4-(4-(1H-pyrazol-1-yl)benzyl)-N-((1S,2S)-2-hydroxycyclopentyl)-5-methyl-6-(1-methyl-1H-pyrazol-3-yl)picolinamide;

4-(4-(1H-pyrazol-1-yl)benzyl)-N-((1S,2S)-2-hydroxycyclobutyl)-5-methyl-6-(1-methyl-1H-pyrazol-3-yl)picolinamide;

4-(4-(1H-pyrazol-1-yl)benzyl)-5-methyl-6-(1-methyl-1H-pyrazol-3-yl)-N-((tetrahydro-2H-pyran-4-yl)methyl)picolinamide;

(S)-4-(4-(1H-pyrazol-1-yl)benzyl)-5-methyl-6-(1-methyl-1H-pyrazol-3-yl)-N-((tetrahydrofuran-2-yl)methyl)picolinamide;

(R)-4-(4-(1H-pyrazol-1-yl)benzyl)-5-methyl-6-(1-methyl-1H-pyrazol-3-yl)-N-((tetrahydrofuran-2-yl)methyl)picolinamide;

4-(4-(1H-pyrazol-1-yl)benzyl)-N-(3,3-dimethyltetrahydro-2H-pyran-4-yl)-5-methyl-6-(1-methyl-1H-pyrazol-3-yl)picolinamide;

N-((3R,4S)-3-hydroxytetrahydro-2H-pyran-4-yl)-5-methyl-6-(1-methyl-1H-pyrazol-3-yl)-4-((6-methylpyridin-3-yl)methyl)picolinamide;

N-((1S,2S)-2-hydroxycyclohexyl)-5-methyl-6-(1-methyl-1H-pyrazol-3-yl)-4-((6-methylpyridin-3-yl)methyl)picolinamide; and N-((1S,2S)-2-hydroxycyclopentyl)-5-methyl-6-(1-methyl-1H-pyrazol-3-yl)-4-((6-methylpyridin-3-yl)methyl)picolinamide; or a pharmaceutically acceptable salt thereof.

Compound names can be assigned by using the Struct=Name naming algorithm as part of CHEMDRAW® ULTRA v. 14.0.0.117.

The compound may exist as a stereoisomer wherein asymmetric or chiral centers are present. The stereoisomer is "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The disclosure contemplates various stereoisomers and mixtures thereof and these are specifically included within the scope of this invention. Stereoisomers include enantiomers and diastereomers, and mixtures of enantiomers or diastereomers. Individual stereoisomers of the compounds may be prepared synthetically from commercially available starting materials, which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry," 5th edition (1989), Longman Scientific & Technical, Essex CM20 2JE, England, or (2) direct separation of the mixture of optical enantiomers on chiral chromatographic columns, or (3) fractional recrystallization methods.

It should be understood that the compound may possess tautomeric forms, as well as geometric isomers, and that these also constitute embodiments of the disclosure.

The present disclosure also includes an isotopically-labeled compound, which is identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^2$H, $^3$H, $^{13}$C, $^{14}$C, $^{15}$N, $^{18}$O, $^{17}$O $^{31}$P, $^{32}$P, $^{35}$S, $^{18}$F, and $^{36}$Cl, respectively. Substitution with heavier isotopes such as deuterium, i.e. $^2$H, can afford certain therapeutic advantages resulting from greater metabolic stability, for example increased in vivo half-life or reduced dosage requirements and, hence, may be preferred in some circumstances. The compound may incorporate positron-emitting isotopes for medical imaging and positron-emitting tomography (PET) studies for determining the distribution of receptors. Suitable positron-emitting isotopes that can be incorporated in compounds of formula (I) are $^{11}$C, $^{13}$N, $^{15}$O, and $^{18}$F. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

In some embodiments, in compounds of formula (I), any hydrogen atom may be deuterium. For example, in compounds of formula (I), $R^1$ may be deuterium.

The disclosed compounds may exist as pharmaceutically acceptable salts. The term "pharmaceutically acceptable salt" refers to salts or zwitterions of the compounds which are water or oil-soluble or dispersible, suitable for treatment of disorders without undue toxicity, irritation, and allergic response, commensurate with a reasonable benefit/risk ratio and effective for their intended use. The salts may be prepared during the final isolation and purification of the compounds or separately by reacting an amino group of the compounds with a suitable acid. For example, a compound may be dissolved in a suitable solvent, such as but not limited to methanol and water and treated with at least one equivalent of an acid, like hydrochloric acid. The resulting salt may precipitate out and be isolated by filtration and dried under reduced pressure. Alternatively, the solvent and excess acid may be removed under reduced pressure to provide a salt. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetate, trifluoroacetate, glutamate, para-toluenesulfonate, undecanoate, hydrochloric, hydrobromic, sulfuric, phosphoric and the like. The amino groups of the compounds may also be quaternized with alkyl chlorides, bromides and iodides such as methyl, ethyl, propyl, isopropyl, butyl, lauryl, myristyl, stearyl and the like.

Basic addition salts may be prepared during the final isolation and purification of the disclosed compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts can be prepared, such as those derived from methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, 1-ephenamine and N,N'-dibenzylethylenediamine, ethylenediamine, ethanolamine, diethanolamine, piperidine, piperazine, and the like.

3. Pharmaceutical Compositions

The disclosed compounds may be incorporated into pharmaceutical compositions suitable for administration to a subject (such as a patient, which may be a human or non-human). The disclosed compounds may also be provided as formulations, such as spray-dried dispersion formulations.

The pharmaceutical compositions and formulations may include a "therapeutically effective amount" or a "prophylactically effective amount" of the agent. A "therapeutically effective amount" refers to an amount effective, at dosages and for periods of time necessary, to achieve the desired therapeutic result. A therapeutically effective amount of the composition may be determined by a person skilled in the art and may vary according to factors such as the disease state, age, sex, and weight of the individual, and the ability of the composition to elicit a desired response in the individual. A therapeutically effective amount is also one in which any toxic or detrimental effects of a compound of the invention (e.g., a compound of formula (I)) are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

For example, a therapeutically effective amount of a compound of formula (I), may be about 1 mg/kg to about 1000 mg/kg, about 5 mg/kg to about 950 mg/kg, about 10 mg/kg to about 900 mg/kg, about 15 mg/kg to about 850 mg/kg, about 20 mg/kg to about 800 mg/kg, about 25 mg/kg to about 750 mg/kg, about 30 mg/kg to about 700 mg/kg, about 35 mg/kg to about 650 mg/kg, about 40 mg/kg to about 600 mg/kg, about 45 mg/kg to about 550 mg/kg, about 50 mg/kg to about 500 mg/kg, about 55 mg/kg to about 450 mg/kg, about 60 mg/kg to about 400 mg/kg, about 65 mg/kg to about 350 mg/kg, about 70 mg/kg to about 300 mg/kg, about 75 mg/kg to about 250 mg/kg, about 80 mg/kg to about 200 mg/kg, about 85 mg/kg to about 150 mg/kg, and about 90 mg/kg to about 100 mg/kg.

The pharmaceutical compositions and formulations may include pharmaceutically acceptable carriers. The term "pharmaceutically acceptable carrier," as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such as propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Thus, the compounds and their physiologically acceptable salts and solvates may be formulated for administration by, for example, solid dosing, eye drop, in a topical oil-based formulation, injection, inhalation (either through the mouth or the nose), implants, or oral, buccal, parenteral, or rectal administration. Techniques and formulations may generally be found in "Remington's Pharmaceutical Sciences," (Meade Publishing Co., Easton, Pa.). Therapeutic compositions must typically be sterile and stable under the conditions of manufacture and storage.

The route by which the disclosed compounds are administered and the form of the composition will dictate the type of carrier to be used. The composition may be in a variety of forms, suitable, for example, for systemic administration (e.g., oral, rectal, nasal, sublingual, buccal, implants, or parenteral) or topical administration (e.g., dermal, pulmonary, nasal, aural, ocular, liposome delivery systems, or iontophoresis).

Carriers for systemic administration typically include at least one of diluents, lubricants, binders, disintegrants, colorants, flavors, sweeteners, antioxidants, preservatives, glidants, solvents, suspending agents, wetting agents, surfactants, combinations thereof, and others. All carriers are optional in the compositions.

Suitable diluents include sugars such as glucose, lactose, dextrose, and sucrose; diols such as propylene glycol; calcium carbonate; sodium carbonate; sugar alcohols, such as glycerin; mannitol; and sorbitol. The amount of diluent(s) in a systemic or topical composition is typically about 50 to about 90%.

Suitable lubricants include silica, talc, stearic acid and its magnesium salts and calcium salts, calcium sulfate; and liquid lubricants such as polyethylene glycol and vegetable oils such as peanut oil, cottonseed oil, sesame oil, olive oil, corn oil and oil of theobroma. The amount of lubricant(s) in a systemic or topical composition is typically about 5 to about 10%.

Suitable binders include polyvinyl pyrrolidone; magnesium aluminum silicate; starches such as corn starch and potato starch; gelatin; tragacanth; and cellulose and its derivatives, such as sodium carboxymethylcellulose, ethyl cellulose, methylcellulose, microcrystalline cellulose, and sodium carboxymethylcellulose. The amount of binder(s) in a systemic composition is typically about 5 to about 50%.

Suitable disintegrants include agar, alginic acid and the sodium salt thereof, effervescent mixtures, croscarmellose, crospovidone, sodium carboxymethyl starch, sodium starch glycolate, clays, and ion exchange resins. The amount of disintegrant(s) in a systemic or topical composition is typically about 0.1 to about 10%.

Suitable colorants include a colorant such as an FD&C dye. When used, the amount of colorant in a systemic or topical composition is typically about 0.005 to about 0.1%.

Suitable flavors include menthol, peppermint, and fruit flavors. The amount of flavor(s), when used, in a systemic or topical composition is typically about 0.1 to about 1.0%.

Suitable sweeteners include aspartame and saccharin. The amount of sweetener(s) in a systemic or topical composition is typically about 0.001 to about 1%.

Suitable antioxidants include butylated hydroxyanisole ("BHA"), butylated hydroxytoluene ("BHT"), and vitamin E. The amount of antioxidant(s) in a systemic or topical composition is typically about 0.1 to about 5%.

Suitable preservatives include benzalkonium chloride, methyl paraben and sodium benzoate. The amount of preservative(s) in a systemic or topical composition is typically about 0.01 to about 5%.

Suitable glidants include silicon dioxide. The amount of glidant(s) in a systemic or topical composition is typically about 1 to about 5%.

Suitable solvents include water, isotonic saline, ethyl oleate, glycerine, hydroxylated castor oils, alcohols such as ethanol, and phosphate buffer solutions. The amount of solvent(s) in a systemic or topical composition is typically from about 0 to about 100%.

Suitable suspending agents include AVICEL RC-591 (from FMC Corporation of Philadelphia, Pa.) and sodium alginate. The amount of suspending agent(s) in a systemic or topical composition is typically about 1 to about 8%.

Suitable surfactants include lecithin, Polysorbate 80, and sodium lauryl sulfate, and the TWEENS from Atlas Powder Company of Wilmington, Del. Suitable surfactants include those disclosed in the C.T.F.A. Cosmetic Ingredient Handbook, 1992, pp. 587-592; Remington's Pharmaceutical Sciences, 15th Ed. 1975, pp. 335-337; and McCutcheon's Volume 1, Emulsifiers & Detergents, 1994, North American Edition, pp. 236-239. The amount of surfactant(s) in the systemic or topical composition is typically about 0.1% to about 5%.

Although the amounts of components in the systemic compositions may vary depending on the type of systemic composition prepared, in general, systemic compositions include 0.01% to 50% of an active compound (e.g., a compound of formula (I)) and 50% to 99.99% of one or more carriers. Compositions for parenteral administration typically include 0.1% to 10% of actives and 90% to 99.9% of a carrier including a diluent and a solvent.

Compositions for oral administration can have various dosage forms. For example, solid forms include tablets, capsules, granules, and bulk powders. These oral dosage forms include a safe and effective amount, usually at least about 5%, and more particularly from about 25% to about 50% of actives. The oral dosage compositions include about 50% to about 95% of carriers, and more particularly, from about 50% to about 75%.

Tablets can be compressed, tablet triturates, enteric-coated, sugar-coated, film-coated, or multiple-compressed. Tablets typically include an active component, and a carrier comprising ingredients selected from diluents, lubricants, binders, disintegrants, colorants, flavors, sweeteners, glidants, and combinations thereof. Specific diluents include calcium carbonate, sodium carbonate, mannitol, lactose and cellulose. Specific binders include starch, gelatin, and sucrose. Specific disintegrants include alginic acid and croscarmellose. Specific lubricants include magnesium stearate, stearic acid, and talc. Specific colorants are the FD&C dyes, which can be added for appearance. Chewable tablets preferably contain sweeteners such as aspartame and saccharin, or flavors such as menthol, peppermint, fruit flavors, or a combination thereof.

Capsules (including implants, time release and sustained release formulations) typically include an active compound (e.g., a compound of formula (I)), and a carrier including one or more diluents disclosed above in a capsule comprising gelatin. Granules typically comprise a disclosed compound, and preferably glidants such as silicon dioxide to improve flow characteristics. Implants can be of the biodegradable or the non-biodegradable type.

The selection of ingredients in the carrier for oral compositions depends on secondary considerations like taste, cost, and shelf stability, which are not critical for the purposes of this invention.

Solid compositions may be coated by conventional methods, typically with pH or time-dependent coatings, such that a disclosed compound is released in the gastrointestinal tract in the vicinity of the desired application, or at various points and times to extend the desired action. The coatings typically include one or more components selected from the group consisting of cellulose acetate phthalate, polyvinyl acetate phthalate, hydroxypropyl methyl cellulose phthalate, ethyl cellulose, EUDRAGIT® coatings (available from Evonik Industries of Essen, Germany), waxes and shellac.

Compositions for oral administration can have liquid forms. For example, suitable liquid forms include aqueous solutions, emulsions, suspensions, solutions reconstituted from non-effervescent granules, suspensions reconstituted from non-effervescent granules, effervescent preparations reconstituted from effervescent granules, elixirs, tinctures, syrups, and the like. Liquid orally administered compositions typically include a disclosed compound and a carrier, namely, a carrier selected from diluents, colorants, flavors, sweeteners, preservatives, solvents, suspending agents, and surfactants. Peroral liquid compositions preferably include one or more ingredients selected from colorants, flavors, and sweeteners.

Other compositions useful for attaining systemic delivery of the subject compounds include sublingual, buccal and nasal dosage forms. Such compositions typically include one or more of soluble filler substances such as diluents including sucrose, sorbitol and mannitol; and binders such as acacia, microcrystalline cellulose, carboxymethyl cellulose, and hydroxypropyl methylcellulose. Such compositions may further include lubricants, colorants, flavors, sweeteners, antioxidants, and glidants.

The disclosed compounds can be topically administered. Topical compositions that can be applied locally to the skin may be in any form including solids, solutions, oils, creams, ointments, gels, lotions, shampoos, leave-on and rinse-out hair conditioners, milks, cleansers, moisturizers, sprays, skin patches, and the like. Topical compositions include: a disclosed compound (e.g., a compound of formula (I)), and a carrier. The carrier of the topical composition preferably aids penetration of the compounds into the skin. The carrier may further include one or more optional components.

The amount of the carrier employed in conjunction with a disclosed compound is sufficient to provide a practical quantity of composition for administration per unit dose of the compound. Techniques and compositions for making dosage forms useful in the methods of this invention are described in the following references: Modern Pharmaceutics, Chapters 9 and 10, Banker & Rhodes, eds. (1979); Lieberman et al., Pharmaceutical Dosage Forms: Tablets (1981); and Ansel, Introduction to Pharmaceutical Dosage Forms, 2nd Ed., (1976).

A carrier may include a single ingredient or a combination of two or more ingredients. In the topical compositions, the carrier includes a topical carrier. Suitable topical carriers include one or more ingredients selected from phosphate buffered saline, isotonic water, deionized water, monofunctional alcohols, symmetrical alcohols, aloe vera gel, allantoin, glycerin, vitamin A and E oils, mineral oil, propylene glycol, PPG-2 myristyl propionate, dimethyl isosorbide, castor oil, combinations thereof, and the like. More particularly, carriers for skin applications include propylene glycol, dimethyl isosorbide, and water, and even more particularly, phosphate buffered saline, isotonic water, deionized water, monofunctional alcohols, and symmetrical alcohols.

The carrier of a topical composition may further include one or more ingredients selected from emollients, propellants, solvents, humectants, thickeners, powders, fragrances, pigments, and preservatives, all of which are optional.

Suitable emollients include stearyl alcohol, glyceryl monoricinoleate, glyceryl monostearate, propane-1,2-diol, butane-1,3-diol, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, cetyl palmitate, di-n-butyl sebacate, isopropyl myristate, isopropyl palmitate, isopropyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, myristyl myristate, and combinations thereof. Specific emollients for skin include stearyl alcohol and polydimethylsiloxane. The amount of emollient(s) in a skin-based topical composition is typically about 5% to about 95%.

Suitable propellants include propane, butane, isobutane, dimethyl ether, carbon dioxide, nitrous oxide, and combinations thereof. The amount of propellant(s) in a topical composition is typically about 0% to about 95%.

Suitable solvents include water, ethyl alcohol, methylene chloride, isopropanol, castor oil, ethylene glycol monoethyl ether, diethylene glycol monobutyl ether, diethylene glycol monoethyl ether, dimethylsulfoxide, dimethyl formamide, tetrahydrofuran, and combinations thereof. Specific solvents include ethyl alcohol and homotopic alcohols. The amount of solvent(s) in a topical composition is typically about 0% to about 95%.

Suitable humectants include glycerin, sorbitol, sodium 2-pyrrolidone-5-carboxylate, soluble collagen, dibutyl phthalate, gelatin, and combinations thereof. Specific humectants include glycerin. The amount of humectant(s) in a topical composition is typically 0% to 95%.

The amount of thickener(s) in a topical composition is typically about 0% to about 95%.

Suitable powders include beta-cyclodextrins, hydroxypropyl cyclodextrins, chalk, talc, fullers earth, kaolin, starch, gums, colloidal silicon dioxide, sodium polyacrylate, tetra alkyl ammonium smectites, trialkyl aryl ammonium smectites, chemically-modified magnesium aluminum silicate, organically-modified montmorillonite clay, hydrated aluminum silicate, fumed silica, carboxyvinyl polymer, sodium carboxymethyl cellulose, ethylene glycol monostearate, and combinations thereof. The amount of powder(s) in a topical composition is typically 0% to 95%.

The amount of fragrance in a topical composition is typically about 0% to about 0.5%, particularly, about 0.001% to about 0.1%.

Suitable pH adjusting additives include HCl or NaOH in amounts sufficient to adjust the pH of a topical pharmaceutical composition.

a. Spray-Dried Dispersion Formulations

The disclosed compounds may be formulated as a spray-dried dispersion (SDD). An SDD is a single-phase, amorphous molecular dispersion of a drug in a polymer matrix. It is a solid solution with the compound molecularly "dissolved" in a solid matrix. SDDs are obtained by dissolving drug and a polymer in an organic solvent and then spray-drying the solution. The use of spray drying for pharmaceutical applications can result in amorphous dispersions with increased solubility of Biopharmaceutics Classification System (BCS) class II (high permeability, low solubility) and class IV (low permeability, low solubility) drugs. Formulation and process conditions are selected so that the solvent quickly evaporates from the droplets, thus allowing insufficient time for phase separation or crystallization. SDDs have demonstrated long-term stability and manufacturability. For example, shelf lives of more than 2 years have been demonstrated with SDDs. Advantages of SDDs include, but are not limited to, enhanced oral bioavailability of poorly water-soluble compounds, delivery using traditional solid dosage forms (e.g., tablets and capsules), a reproducible, controllable and scalable manufacturing process and broad applicability to structurally diverse insoluble compounds with a wide range of physical properties.

Thus, in one embodiment, the disclosure may provide a spray-dried dispersion formulation comprising a compound of formula (I).

4. Therapeutic Uses and Methods

The disclosed compounds are positive allosteric modulators of mAChR $M_1$. Thus, by positive allosteric modulation, the compounds indirectly activate the muscarinic receptor subtype $M_1$. In one aspect, the disclosed compounds potentiate the agonist response (e.g., acetylcholine) of mAChR $M_1$. In a further aspect, the disclosed compounds increase mAChR $M_1$ response to non-maximal concentrations of agonist in the presence of compound compared to the response to agonist in the absence of compound. The potentiation of mAChR $M_1$ activity can be demonstrated by methodology known in the art. For example, activation of mAChR $M_1$ activity can be determined by measurement of calcium flux in response to agonist, e.g. acetylcholine, in cells loaded with a $Ca^{2+}$-sensitive fluorescent dye (e.g., Fluo-4). In a further aspect, the calcium flux was measured as an increase in fluorescent static ratio. In a yet further aspect, positive allosteric modulator activity was analyzed as a concentration-dependent increase in the $EC_{20}$ acetylcholine response (i.e. the response of mAChR $M_1$ at a concentration of acetylcholine that yields 20% of the maximal response).

In an embodiment, the disclosed compounds may activate mAChR $M_1$ response as an increase in calcium fluorescence in mAChR $M_1$-transfected CHO-K1 cells in the presence of the compound, compared to the response of equivalent CHO-K1 cells in the absence of the compound. For example, a disclosed compound may have an $EC_{50}$ of less than or equal to 10 µM, less than or equal to 5 µM, less than or equal to 2.5 µM, less than or equal to 1 µM, less than or equal to 500 nM, less than or equal to 250 nM, less than or equal to 100 nM, or less than or equal to 50 nM. In an embodiment, the mAChR $M_1$-transfected CHO-K1 cells are transfected with human mAChR $M_1$. In another embodiment, the mAChR $M_1$-transfected CHO-K1 cells are transfected with rat mAChR $M_1$.

In an embodiment, the disclosed compounds exhibit weak or substantially no agonist activation of mAChR $M_1$ response (i.e., lack of activation in the absence of a known agonist such as acetylcholine). Lack of agonist activity may be measured as weak or no increase in calcium fluorescence in mAChR $M_1$-transfected CHO-K1 cells in the presence of the compound, compared to the response of equivalent CHO-K1 cells in the absence of the compound. Lack of mAChR $M_1$ agonist activity may be determined as a percent response relative to acetylcholine. For example, a disclosed compound may have less than or equal to 30%, 25%, 20%, 15%, 10%, 5%, or 1% mAChR $M_1$ agonist activity relative to acetylcholine. A disclosed compound may have substantially no mAChR $M_1$ agonist activity. In further embodiments, the disclosed compounds exhibit positive allosteric modulation of mAChR $M_1$ response to acetylcholine, as described herein, at concentrations that have weak or substantially no agonist activity, as described herein. The absence of mAChR $M_1$ agonist activity may contribute to the avoidance of cholinergic adverse effect liability.

In an embodiment, the disclosed compounds exhibit potentiation of mAChR $M_1$ response to acetylcholine as an increase in response to non-maximal concentrations of acetylcholine in CHO-K1 cells transfected with a mammalian mAChR $M_1$ in the presence of the compound, compared to the response to acetylcholine in the absence of the compound. For example, CHO-K1 cells can be transfected with human mAChR $M_1$. For example, CHO-K1 cells can be transfected with rat mAChR $M_1$. For example, a compound can exhibit positive allosteric modulation of mAChR $M_1$ with an $EC_{50}$ of less than or equal to 10 µM, less than or equal to 5 µM, less than or equal to 2.5 µM, less than or equal to 1 µM, less than or equal to 500 nM, less than or equal to 250 nM, or less than or equal to 100 nM. Alternatively, the disclosed compounds exhibit potentiation of mAChR $M_1$ response to acetylcholine as an increase in response to non-maximal concentrations of acetylcholine in CHO-K1 cells transfected with human mAChR $M_1$ in the presence of the compound, compared to the response to acetylcholine in the absence of the compound. For example, a compound can exhibit positive allosteric modulation of mAChR $M_1$ with an $EC_{50}$ of less than or equal to 10 µM, less than or equal to 5 µM, less than or equal to 2.5 µM, less than or equal to 1 µM, less than or equal to 500 nM, less than or equal to 250 nM, less than or equal to 100 nM, or less than or equal to 50 nM.

In an embodiment, the disclosed compounds exhibit positive allosteric modulation of mAChR $M_1$ response to acetylcholine as an increase in response to non-maximal concentrations of acetylcholine in CHO-K1 cells transfected with a mAChR $M_1$ in the presence of the compound, compared to the response to acetylcholine in the absence of the compound. For example, the disclosed compounds may exhibit positive allosteric modulation of the mAChR $M_1$ response to acetylcholine with an $EC_{50}$ of less than or equal to 10 µM, less than or equal to 5 µM, less than or equal to 2.5 µM, less than or equal to 1 µM, less than or equal to 500 nM, less than or equal to 250 nM, or less than or equal to 100 nM. In an embodiment, the $EC_{50}$ for positive allosteric modulation is determined in CHO-K1 cells are transfected with a mAChR $M_1$. In another embodiment, the CHO-K1 cells are transfected with a human mAChR $M_1$. In another embodiment, the CHO-K1 cells are transfected with a rat mAChR $M_1$.

In an embodiment, the compounds activate mAChR $M_1$ response in mAChR $M_1$-transfected CHO-K1 cells with an $EC_{50}$ less than the $EC_{50}$ for one or more of mAChR $M_2$, mAChR $M_3$, mAChR $M_4$, or mAChR $M_5$ response in mAChR $M_2$, $M_3$, $M_4$ or $M_5$-transfected CHO-K1 cells. That is, the disclosed compounds can have selectivity for the mAChR $M_1$ receptor vis-à-vis one or more of the mAChR $M_2$, $M_3$, $M_4$ or $M_5$ receptors. For example, the disclosed compounds can activate mAChR $M_1$ response with an $EC_{50}$ of at least 5-fold less than that for mAChR $M_2$, at least 10-fold less than that for mAChR $M_2$, at least 20-fold less than that for mAChR $M_2$, at least 30-fold less than that for mAChR $M_2$, at least 50-fold less than that for mAChR $M_2$, or at least 100-fold less than that for mAChR $M_2$. In another embodiment, the disclosed compounds can activate mAChR $M_1$ response with an $EC_{50}$ of at least 5-fold less than that for mAChR $M_3$, at least 10-fold less than that for mAChR $M_3$, at least 20-fold less than that for $M_3$, at least 30-fold less than that for mAChR $M_3$, at least 50-fold less than that for mAChR $M_3$, or at least 100-fold less than that for mAChR $M_3$. In another embodiment, the disclosed compounds can activate mAChR $M_1$ response with an $EC_{50}$ of at least 5-fold less than that for mAChR $M_4$, at least 10-fold less than that for mAChR $M_4$, at least 20-fold less than that for $M_4$, at least 30-fold less than that for mAChR $M_4$, at least 50-fold less than that for mAChR $M_4$, or at least 100-fold less than that for mAChR $M_4$. In another embodiment, the disclosed compounds can activate mAChR $M_1$ response with an $EC_{50}$ of at least 5-fold less than that for mAChR $M_5$, at least 10-fold less than that for mAChR $M_5$, at least 20-fold less than that for mAChR $M_5$, at least 30-fold less than that for mAChR $M_5$, at least 50-fold less than that for mAChR $M_5$, or at least 100-fold less than that for mAChR $M_5$. In another embodiment, the disclosed compounds can activate mAChR $M_1$ response with an $EC_{50}$ of at least 5-fold less than that for the mAChR $M_2$, $M_3$, $M_4$ or $M_5$ receptors, at least 10-fold less than that for the mAChR $M_2$, $M_3$, $M_4$ or $M_5$ receptors, at least 20-fold less than that for the mAChR $M_2$, $M_3$, $M_4$ or $M_5$ receptors, at least 30-fold less than that for the mAChR $M_2$, $M_3$, $M_4$ or $M_5$ receptors, at least 50-fold less than that for the mAChR $M_2$, $M_3$, $M_4$ or $M_5$ receptors, or at least 100-fold less than that for the mAChR $M_2$, $M_3$, $M_4$ or $M_5$ receptors. In another embodiment, the compound activates mAChR $M_1$ response in mAChR $M_1$-transfected CHO-K1 cells and is inactive for one or more of mAChR $M_1$, mAChR $M_3$, mAChR $M_4$, or mAChR $M_5$ response in mAChR $M_2$, $M_3$, $M_4$ or $M_5$-transfected CHO-K1 cells.

In an embodiment, the compounds activate mAChR $M_1$ response in $M_1$-transfected CHO-K1 cells with an $EC_{50}$ of less than or equal to 10 µM and exhibits a selectivity for the $M_1$ receptor vis-à-vis one or more of the mAChR $M_2$, $M_3$, $M_4$ or $M_5$ receptors. For example, the compounds can have an $EC_{50}$ of less than or equal to 10 µM, less than or equal to 5 µM, less than or equal to 2.5 µM, less than or equal to 1 µM, less than or equal to 500 nM, less than or equal to 250 nM, less than or equal to 100 nM, or less than or equal to 50 nM; and the compounds can also activate mAChR $M_1$ response with an $EC_{50}$ of at least 5-fold less than that for mAChR $M_2$, at least 10-fold less than that for mAChR $M_2$, at least 20-fold less than that for mAChR $M_2$, at least 30-fold less than that for mAChR $M_2$, or at least 50-fold less than that for mAChR $M_2$. In another embodiment, the compounds can have an $EC_{50}$ of less than or equal to 10 µM, less than or equal to 5 µM, less than or equal to 2.5 µM, less than or equal to 1 µM, less than or equal to 500 nM, less than or equal to 250 nM, less than or equal to 100 nM, or less than or equal to 50 nM; and the compounds can also activate mAChR $M_1$ response with an $EC_{50}$ of at least 5-fold less than that for mAChR $M_3$, at least 10-fold less than that for mAChR $M_3$, at least 20-fold less than that for mAChR $M_3$, at least 30-fold less than that for mAChR $M_3$, or at least 50-fold less than that for mAChR $M_3$. In another embodiment, the compounds can have an $EC_{50}$ of less than or equal to 10 µM, less than or equal to 5 µM, less than or equal to 2.5 µM, less than or equal to 1 µM, less than or equal to 500 nM, less than or equal to 250 nM, less than or equal to 100 nM, or less than or equal to 50 nM; and the compounds can also activate mAChR $M_1$ response with an $EC_{50}$ of at least 5-fold less than that for mAChR $M_4$, of at least 10-fold less than that for mAChR $M_4$, of at least 20-fold less than that for mAChR $M_4$, of at least 30-fold less than that for mAChR $M_4$, or at least 50-fold less than that for mAChR $M_4$. In another embodiment, the compound can have an $EC_{50}$ of less than or equal to 10 µM, less than or equal to 5 µM, less than or equal to 2.5 µM, less than or equal to 1 µM, less than or equal to 500 nM, less than or equal to 250 nM, less than or equal to 100 nM, or less than or equal to 50 nM; and the compounds can also activate mAChR $M_1$ response with an $EC_{50}$ of at least 5-fold less than that for mAChR $M_5$, of at least 10-fold less than that for mAChR $M_5$, of at least 20-fold less than that for mAChR $M_5$, of at least 30-fold less than that for mAChR $M_5$, or at least 50-fold less than that for mAChR $M_5$. In another embodiment, the compounds can have an $EC_{50}$ of less than or equal to 10 µM, less than or equal to 5 µM, less than or equal to 2.5 µM, less than or equal to 1 µM, less than or equal to 500 nM, less than or equal to 250 nM, less than or equal to 100 nM, or less than or equal to 50 nM; and the compounds can also activate mAChR $M_1$ response with an $EC_{50}$ of at least 5-fold less than that for the mAChR $M_2$, $M_3$, $M_4$ or $M_5$ receptors, at least 10-fold less than that for the mAChR $M_2$, $M_3$, $M_4$ or $M_5$ receptors, at least 20-fold less than that for the mAChR $M_2$, $M_3$, $M_4$ or $M_5$ receptors, at least 30-fold less than that for the mAChR $M_2$, $M_3$, $M_4$ or $M_5$ receptors, or at least 50-fold less than that for the mAChR $M_2$, $M_3$, $M_4$ or $M_5$ receptors.

The disclosed compounds may be used in methods for treatment of mAChR $M_1$ related medical disorders and/or diseases. The methods of treatment may comprise administering to a subject in need of such treatment a composition comprising a therapeutically effective amount of the compound of formula (I).

The compounds can be administered to a subject in need thereof to modulate mAChR $M_1$, for a variety of diverse biological processes. The present disclosure is directed to methods for administering the composition to potentiate mAChR $M_1$, a GPCR whose dysfunction is associated with neurological and psychiatric disorders, for example.

The compounds may be useful for treating and preventing certain diseases and disorders in humans and animals related to mAChR $M_1$ dysfunction. Treatment or prevention of such diseases and disorders can be effected by modulating mAChR $M_1$ in a subject, by administering a compound or composition of the disclosure, either alone or in combination with another active agent as part of a therapeutic regimen to a subject in need thereof.

In combination therapy, the other drug(s) can be administered by a route and in an amount commonly used therefore, contemporaneously or sequentially with a disclosed compound. When a disclosed compound is used contemporaneously with one or more other drugs, a pharmaceutical composition in unit dosage form containing such drugs and the disclosed compound is preferred. However, the combination therapy can also be administered on overlapping schedules. It is also envisioned that the combination of one or more active ingredients and a disclosed compound can be more efficacious than either as a single agent.

In an embodiment, the compounds can be coadministered with anti-Alzheimer's agents, beta-secretase inhibitors, gamma-secretase inhibitors, orthosteric muscarinic agonists, muscarinic potentiators, cholinesterase inhibitors, HMG-CoA reductase inhibitors, NSAIDs and anti-amyloid antibodies. In a further aspect, the compounds can be administered in combination with sedatives, hypnotics, anxiolytics, antipsychotics (typical and atypical), selective serotonin reuptake inhibitors (SSRIs), monoamine oxidase inhibitors (MAOIs), 5-HT2 antagonists, GlyT1 inhibitors and the like such as, but not limited to: risperidone, clozapine, haloperidol, fluoxetine, prazepam, xanomeline, lithium, phenobarbitol, and salts thereof and combinations thereof.

The compounds may be useful for treating a disease or disorder associated with dysfunction of mAChR $M_1$, wherein the disease or disorder is selected from at least one of Alzheimer's disease, a sleep disorder, a pain disorder, a cognitive disorder, psychosis, schizophrenia, conduct disorder, disruptive behavior disorder, bipolar disorder, psychotic episodes of anxiety, anxiety associated with psychosis, psychotic mood disorders, severe major depressive disorder, mood disorders associated with psychotic disorders, acute mania, depression associated with bipolar disorder, mood disorders associated with schizophrenia, behavioral manifestations of mental retardation, conduct disorder, autistic disorder, movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders.

The compounds may be useful for treating a pain disorder, wherein the pain disorder is neuropathic pain, central pain syndrome, postsurgical pain syndrome, bone and joint pain, repetitive motion pain, dental pain, cancer pain, myofascial pain, perioperative pain, chronic pain, dysmennorhea, inflammatory pain, headache, migraine headache, cluster headache, headache, primary hyperalgesia, secondary hyperalgesis, primary allodynia, secondary allodynia, or a combination thereof.

The compounds disclosed herein are useful for treating, preventing, ameliorating, controlling or reducing the risk of a variety of disorders wherein the patient or subject would benefit from selective positive allosteric modulation of the $M_1$ receptor. In one aspect, a treatment can include selective $M_1$ receptor modulation to an extent effective to affect cholinergic activity. Thus, a disorder can be associated with cholinergic activity, for example cholinergic hypofunction. In one aspect, provided is a method of treating or preventing a disorder in a subject comprising the step of administering to the subject at least one disclosed compound; at least one disclosed pharmaceutical composition; and/or at least one disclosed product in a dosage and amount effective to treat the disorder in the subject.

Also provided is a method for the treatment of one or more disorders, for which muscarinic receptor activation is predicted to be beneficial, in a subject comprising the step of administering to the subject at least one disclosed compound; at least one disclosed pharmaceutical composition; and/or at least one disclosed product in a dosage and amount effective to treat the disorder in the subject.

The disclosure is directed to the use of described chemical compositions to treat diseases or disorders in patients (preferably human) wherein muscarinic receptor activation would be predicted to have a therapeutic effect, such as Alzheimer's disease (both palliative cognitive and disease-modifying), cognitive impairment, schizophrenia, pain disorders (including acute pain, neuropathic pain and inflammatory pain), and sleep disorders, by administering one or more disclosed compounds or products.

Also provided is a method for the treatment of a disorder in a mammal comprising the step of administering to the mammal at least one disclosed compound, composition, or medicament.

a. Neurological and Psychiatric Disorders

The disclosed compounds have utility in treating a variety of neurological and psychiatric disorders, including one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketamine and other dissociative anesthetics, amphetamine and other psychostimulants and cocaine) psychosis psychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age-related cognitive decline; anxiety disorders including acute stress disorder, agoraphobia, generalized anxiety disorder, obsessive-compulsive disorder, panic attack, panic disorder, post-traumatic stress disorder, separation anxiety disorder, social phobia, specific phobia, substance-induced anxiety disorder and anxiety due to a general medical condition; substance-related disorders and addictive behaviors (including substance-induced delirium, persisting dementia, persisting amnestic disorder, psychotic disorder or anxiety disorder; tolerance, dependence or withdrawal from substances including alcohol, amphetamines, cannabis, cocaine, hallucinogens, inhalants, nicotine, opioids, phencyclidine, sedatives, hypnotics or anxiolytics); obesity, bulimia nervosa and compulsive eating disorders; bipolar disorders, mood disorders including depressive disorders; depression including unipolar depression, seasonal depression and post-partum depression, premenstrual syndrome (PMS) and premenstrual dysphoric disorder (PDD), mood disorders due to a general medical condition, and substance-induced mood disorders; learning disorders, pervasive developmental disorder including autistic disorder, attention disorders including attention-deficit hyperactivity disorder (ADHD) and conduct disorder; NMDA receptor-related disorders such as autism, depression, benign forgetfulness, childhood learning disorders and closed head injury; movement disorders, including akinesias and akinetic-rigid syndromes (including Parkinson's disease, drug-induced parkinsonism, post-encephalitic parkinsonism, progressive supranuclear palsy, multiple system atrophy, corticobasal degeneration, parkinsonism-ALS dementia complex and basal ganglia calcification), medication-induced parkinsonism (such as neuroleptic-induced parkinsonism, neuroleptic malignant syndrome, neuroleptic-induced acute dystonia, neuroleptic-induced acute akathisia, neuroleptic-induced tardive dyskinesia and medication-induced postural tremor), Gilles de La Tourette's syndrome, epilepsy, muscular spasms and disorders associated with muscular spasticity or weakness including tremors; dyskinesias including tremor (such as rest tremor, postural tremor and intention tremor), chorea (such as Sydenham's chorea, Huntington's disease, benign hereditary chorea, neuroacanthocytosis, symptomatic chorea, drug-induced chorea and hemiballism), myoclonus (including generalized myoclonus and focal myoclonus), tics (including simple tics, complex tics and symptomatic tics), and dystonia (including generalized dystonia such as idiopathic dystonia, drug-induced dystonia, symptomatic dystonia and paroxysmal dystonia, and focal dystonia such as blepharospasm, oromandibular dystonia, spasmodic dysphonia, spasmodic torticollis, axial dystonia, dystonic writer's cramp and hemiplegic dystonia)]; urinary incontinence; neuronal damage including ocular damage, retinopathy or macular degeneration of the eye, tinnitus, hearing impairment and loss, and brain edema; emesis; and sleep disorders including insomnia and narcolepsy.

1. Cognitive Disorders

The present disclosure provides a method for treating cognitive disorders, comprising: administering to a patient in need thereof an effective amount of a compound of the present disclosure. Particular cognitive disorders are dementia, delirium, amnestic disorders and age-related cognitive decline. The text revision of the fourth edition of the Diagnostic and Statistical Manual of Mental Disorders (DSM-IV-TR) (2000, American Psychiatric Association, Washington D.C.) provides a diagnostic tool that includes cognitive disorders including dementia, delirium, amnestic disorders and age-related cognitive decline. As used herein, the term "cognitive disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "cognitive disorders" is intended to include like disorders that are described in other diagnostic sources.

2. Anxiety Disorders

The present disclosure provides a method for treating anxiety disorders, comprising: administering to a patient in need thereof an effective amount of a compound of the present disclosure. Particular anxiety disorders are generalized anxiety disorder, obsessive-compulsive disorder and panic attack. The text revision of the fourth edition of the Diagnostic and Statistical Manual of Mental Disorders (DSM-IV-TR) (2000, American Psychiatric Association, Washington D.C.) provides a diagnostic tool that includes anxiety disorders are generalized anxiety disorder, panic disorder with or without agoraphobia, agoraphobia without history of panic disorder, specific phobia, social phobia, obsessive-compulsive disorder, post-traumatic stress disorder, acute stress disorder, generalized anxiety disorder, anxiety disorder due to a general medical condition, substance-induced anxiety disorder and anxiety disorder not otherwise specified. As used herein, the term "anxiety disorders" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "anxiety disorders" is intended to include like disorders that are described in other diagnostic sources.

3. Alzheimer's Disease

Alzheimer's disease (AD) is a neurodegenerative disease affecting the elderly, which results in progressive impairment of memory, language skills and severe behavioral deficits. Hallmarks of the disease include degeneration of cholinergic neurons in the cerebral cortex, hippocampus, basal forebrain and other regions of the brain important for memory and cognition. Other hallmarks of AD include neurofibrillary tangles composed of hyperphosphorylated tau and accumulation of amyloid β peptide (Aβ). A is a 39-43 amino acid peptide produced in the brain by proteolytic processing of β-amyloid precursor protein (APP) by the β-amyloid cleaving enzyme (BACE) and gamma secretase which leads to accumulation of Aβ in the brain, where Aβ 1-40 and 1-42 are the principal aggregate-forming species of Aβ.

Activation of various muscarinic receptors, particularly the $M_1$ subtype, has been proposed as a mechanism to enhance cognition in disorders such as AD. Thus, without wishing to be bound by theory, it is believed that selective positive allosteric modulators of mAChR subtypes that regulate processes involved in cognitive function could prove superior to AChE inhibitors for treatment of AD and related disorders as it is postulated that these compounds would exhibit improved selectivity for specific mAChRs.

Phase III clinical trials have shown that orthosteric mAChR activators can have efficacy in improving cognitive performance in AD patients. Moreover, data indicate that administration of $M_1$ activators decreases behavioral disturbances, including delusions, hallucinations, outbursts, and other symptoms in patients suffering from neurodegenerative diseases such as Alzheimer's disease. However, dose limiting adverse effects that may be due to lack of mAChR $M_1$ selectivity led to failed launches of previous $M_1$ agonists. In some cases, evidence suggests that mAChR activation also has the potential to be disease-modifying in that these agents may lower A in AD patients. The $M_1$-selective allosteric agonist TBPB was found to display effects on the processing of APP toward the non-amyloidogenic pathway and decrease Aβ 1-40 and 1-42 production in vitro. These data suggest that selective activation of $M_1$ may provide a novel approach for both symptomatic and disease modifying the treatment of Alzheimer's disease.

4. Schizophrenia

Schizophrenia is a debilitating psychiatric disorder characterized by a combination of negative (blunted affect, withdrawal, anhedonia) and positive (paranoia, hallucinations, delusions) symptoms as well as marked cognitive deficits. While schizophrenia remains an idiopathic disorder, it appears to be produced by a complex interaction of biological, environmental, and genetic factors. Over 40 years ago it was found that phencyclidine (PCP) induces a psychotic state in humans that is very similar to that observed in schizophrenic patients. The finding that the main mode of action of PCP is that of a non-competitive antagonist of the N-methyl-D-aspartate (NMDA) subtype of ionotropic glutamate receptor stimulated a series of studies that have led to the development of the NMDA receptor hypofunction model of schizophrenia.

The present disclosure provides a method for treating schizophrenia or psychosis comprising: administering to a patient in need thereof an effective amount of a compound of the present disclosure. Particular schizophrenia or psychosis pathologies are paranoid, disorganized, catatonic or undifferentiated schizophrenia and substance-induced psychotic disorder. The text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder.

NMDA receptor function can be modulated by activation of G Protein-Coupled Receptors (GPCRs) that are known to physically and/or functionally interact with the NMDA receptor. The NMDA receptor hypofunction hypothesis is a proposal to explain the underlying cause of schizophrenia. According to this hypothesis, any agent that can potentiate NMDA receptor currents, either directly by action on modulatory sites on the NMDA receptor (e.g., the glycine co-agonist binding site) or indirectly by activation of GPCRs known to potentiate NMDA receptor function (e.g. the mAChR $M_1$), has the potential to ameliorate the symptoms of schizophrenia. In both preclinical and in clinical studies, xanomeline, an $M_1/M_4$ preferring orthosteric agonist has proved efficacious with regard to positive, negative and cognitive symptoms, indicating that $M_1$ activation is a reasonable approach to the treatment of schizophrenia. More recently, the selective $M_1$ allosteric agonist TBPB demonstrated efficacy in multiple preclinical models of schizophrenia.

As used herein, the term "schizophrenia or psychosis" includes treatment of those mental disorders as described in DSM-W-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

5. Substance-Related Disorders and Addictive Behaviors

The present disclosure provides a method for treating substance-related disorders and addictive behaviors, comprising: administering to a patient in need thereof an effective amount of a compound of the present disclosure. Particular substance-related disorders and addictive behaviors are persisting dementia, persisting amnestic disorder, psychotic disorder or anxiety disorder induced by substance abuse; and tolerance of, dependence on or withdrawal from substances of abuse. The text revision of the fourth edition of the Diagnostic and Statistical Manual of Mental Disorders (DSM-IV-TR) (2000, American Psychiatric Association, Washington D.C.) provides a diagnostic tool that includes persisting dementia, persisting amnestic disorder, psychotic disorder or anxiety disorder induced by substance abuse; and tolerance of, dependence on or withdrawal from substances of abuse. As used herein, the term "substance-related disorders and addictive behaviors" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "substance-related disorders and addictive behaviors" is intended to include like disorders that are described in other diagnostic sources.

6. Pain

In another aspect, the present disclosure provides a method for treating pain, comprising: administering to a patient in need thereof an effective amount of a compound of the present disclosure. Particular pain embodiments are bone and joint pain (osteoarthritis), repetitive motion pain, dental pain, cancer pain, myofascial pain (muscular injury, fibromyalgia), perioperative pain (general surgery, gynecological), chronic pain and neuropathic pain.

7. Obesity and Eating Disorders

The present disclosure provides a method for treating obesity or eating disorders associated with excessive food intake and complications associated therewith, comprising: administering to a patient in need thereof an effective amount of a compound of the present disclosure. Obesity is included in the tenth edition of the International Classification of Diseases and Related Health Problems (ICD-10) (1992 World Health Organization) as a general medical condition. The text revision of the fourth edition of the Diagnostic and Statistical Manual of Mental Disorders (DSM-IV-TR) (2000, American Psychiatric Association, Washington D.C.) provides a diagnostic tool that includes obesity in the presence of psychological factors affecting medical condition. As used herein, the term "obesity or eating disorders associated with excessive food intake" includes treatment of those medical conditions and disorders described in ICD-10 and DSM-W-TR. The skilled artisan will recognize that there are alternative nomenclatures, nosologies and classification systems for general medical conditions, and that these systems evolve with medical and scientific progress. Thus, the term "obesity or eating disorders associated with excessive food intake" is intended to include like conditions and disorders that are described in other diagnostic sources.

The compounds are further useful in a method for the prevention, treatment, control, amelioration, or reduction of risk of the diseases, disorders and conditions noted herein. The compounds are further useful in a method for the prevention, treatment, control, amelioration, or reduction of risk of the aforementioned diseases, disorders and conditions in combination with other agents.

The present disclosure is further directed to administration of a selective $M_1$ receptor modulator for improving treatment outcomes in the context of cognitive or behavioral therapy. That is, in one aspect, the disclosure relates to a cotherapeutic method comprising the step of administering to a mammal an effective amount and dosage of at least one compound of the disclosure in connection with cognitive or behavioral therapy.

In another aspect, administration improves treatment outcomes in the context of cognitive or behavioral therapy. Administration in connection with cognitive or behavioral therapy can be continuous or intermittent. Administration need not be simultaneous with therapy and can be before, during, and/or after therapy. For example, cognitive or behavioral therapy can be provided within 1, 2, 3, 4, 5, 6, 7 days before or after administration of the compound. As a further example, cognitive or behavioral therapy can be provided within 1, 2, 3, or 4 weeks before or after administration of the compound. As another example, cognitive or behavioral therapy can be provided before or after administration within a period of time of 1, 2, 3, 4, 5, 6, 7, 8, 9, or 10 half-lives of the administered compound.

b. Modes of Administration

Methods of treatment may include any number of modes of administering a disclosed composition. Modes of administration may include tablets, pills, dragees, hard and soft gel capsules, granules, pellets, aqueous, lipid, oily or other solutions, emulsions such as oil-in-water emulsions, liposomes, aqueous or oily suspensions, syrups, elixirs, solid emulsions, solid dispersions or dispersible powders. For the preparation of pharmaceutical compositions for oral administration, the agent may be admixed with commonly known and used adjuvants and excipients such as for example, gum arabic, talcum, starch, sugars (such as, e.g., mannitose, methyl cellulose, lactose), gelatin, surface-active agents, magnesium stearate, aqueous or non-aqueous solvents, paraffin derivatives, cross-linking agents, dispersants, emulsifiers, lubricants, conserving agents, flavoring agents (e.g., ethereal oils), solubility enhancers (e.g., benzyl benzoate or benzyl alcohol) or bioavailability enhancers (e.g. Gelucire™). In the pharmaceutical composition, the agent may also be dispersed in a microparticle, e.g. a nanoparticulate composition.

For parenteral administration, the agent can be dissolved or suspended in a physiologically acceptable diluent, such as, e.g., water, buffer, oils with or without solubilizers, surface-active agents, dispersants or emulsifiers. As oils for example and without limitation, olive oil, peanut oil, cottonseed oil, soybean oil, castor oil and sesame oil may be used. More generally spoken, for parenteral administration, the agent can be in the form of an aqueous, lipid, oily or other kind of solution or suspension or even administered in the form of liposomes or nano-suspensions.

The term "parenterally," as used herein, refers to modes of administration which include intravenous, intramuscular, intraperitoneal, intrasternal, subcutaneous and intraarticular injection and infusion.

c. Combination Therapies

In one aspect, the disclosed compounds can be used in combination with one or more other drugs in the treatment, prevention, control, amelioration, or reduction of risk of diseases or conditions for which disclosed compounds or the other drugs can have utility, where the combination of the drugs together are safer or more effective than either drug alone. Such other drug(s) can be administered, by a route and in an amount commonly used therefor, contemporaneously or sequentially with a compound of the present disclosure. When a compound of the present disclosure is used contemporaneously with one or more other drugs, a pharmaceutical composition in unit dosage form containing such other drugs and a disclosed compound is preferred. However, the combination therapy can also include therapies in which a disclosed compound and one or more other drugs are administered on different overlapping schedules. It is also contemplated that when used in combination with one or more other active ingredients, the disclosed compounds and the other active ingredients can be used in lower doses than when each is used singly.

Accordingly, the pharmaceutical compositions include those that contain one or more other active ingredients, in addition to a compound of the present disclosure.

The above combinations include combinations of a disclosed compound not only with one other active compound, but also with two or more other active compounds. Likewise, disclosed compounds can be used in combination with other drugs that are used in the prevention, treatment, control, amelioration, or reduction of risk of the diseases or conditions for which disclosed compounds are useful. Such other drugs can be administered, by a route and in an amount commonly used therefor, contemporaneously or sequentially with a compound of the present disclosure. When a compound of the present disclosure is used contemporaneously with one or more other drugs, a pharmaceutical composition containing such other drugs in addition to a disclosed compound is preferred. Accordingly, the pharmaceutical compositions include those that also contain one or more other active ingredients, in addition to a compound of the present disclosure.

The weight ratio of a disclosed compound to the second active ingredient can be varied and will depend upon the effective dose of each ingredient. Generally, an effective dose of each will be used. Thus, for example, when a compound of the present disclosure is combined with another agent, the weight ratio of a disclosed compound to the other agent will generally range from about 1000:1 to about 1:1000, preferably about 200:1 to about 1:200. Combinations of a compound of the present disclosure and other active ingredients will generally also be within the aforementioned range, but in each case, an effective dose of each active ingredient should be used.

In such combinations disclosed compounds and other active agents can be administered separately or in conjunction. In addition, the administration of one element can be prior to, concurrent to, or subsequent to the administration of other agent(s).

Accordingly, the disclosed compounds can be used alone or in combination with other agents which are known to be beneficial in the subject indications or other drugs that affect receptors or enzymes that either increase the efficacy, safety, convenience, or reduce unwanted side effects or toxicity of the disclosed compounds. The subject compound and the other agent can be coadministered, either in concomitant therapy or in a fixed combination.

In an embodiment, the disclosed compounds can be employed in combination with anti-Alzheimer's agents, beta-secretase inhibitors, gamma-secretase inhibitors, HMG-CoA reductase inhibitors, NSAID's including ibuprofen, vitamin E, and anti-amyloid antibodies. In another embodiment, the subject compound can be employed in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, alprazolam, amisulpride, amitriptyline, amobarbital, amoxapine, aripiprazole, bentazepam, benzoctamine, brotizolam, bupropion, buspirone, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lithium, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, roletamide, secobarbital, sertraline, suproclone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, Zolpidem, and salts thereof, and combinations thereof, and the like, or the subject compound can be administered in conjunction with the use of physical methods such as with light therapy or electrical stimulation.

In an embodiment, the disclosed compounds can be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexol) hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist can be in the form of a pharmaceutically acceptable salt, for example, alentemol hydrobromide, bromocriptine mesylate, fenoldopam mesylate, naxagolide hydrochloride and pergolide mesylate. Lisuride and pramipexol are commonly used in a non-salt form.

In an embodiment, the disclosed compounds can be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound can be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound can be employed in combination with acetophenazine, alentemol, aripiprazole, amisulpride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, trihexyphenidyl, thioridazine, thiothixene, trifluoperazine or ziprasidone.

In an embodiment, the disclosed compounds can be employed in combination with an anti-depressant or anti-anxiety agent, including norepinephrine reuptake inhibitors (including tertiary amine tricyclics and secondary amine tricyclics), selective serotonin reuptake inhibitors (SSRIs), monoamine oxidase inhibitors (MAOIs), reversible inhibitors of monoamine oxidase (RIMAs), serotonin and noradrenaline reuptake inhibitors (SNRIs), corticotropin releasing factor (CRF) antagonists, α-adrenoreceptor antagonists, neurokinin-1 receptor antagonists, atypical anti-depressants, benzodiazepines, 5-HT1A agonists or antagonists, especially 5-HT1A partial agonists, and corticotropin releasing factor (CRF) antagonists. Specific agents include: amitriptyline, clomipramine, doxepin, imipramine and trimipramine; amoxapine, desipramine, maprotiline, nortriptyline and protriptyline; fluoxetine, fluvoxamine, paroxetine and sertraline; isocarboxazid, phenelzine, tranylcypromine and selegiline; moclobemide: venlafaxine; duloxetine; aprepitant; bupropion, lithium, nefazodone, trazodone and viloxazine; alprazolam, chlordiazepoxide, clonazepam, chlorazepate, diazepam, halazepam, lorazepam, oxazepam and prazepam; buspirone, flesinoxan, gepirone and ipsapirone, and pharmaceutically acceptable salts. thereof.

The compounds and processes of the invention will be better understood by reference to the following examples, which are intended as an illustration of and not a limitation upon the scope of the invention.

5. Kits

In one aspect, the disclosure provides kits comprising at least one disclosed compound or a pharmaceutically acceptable salt thereof, and one or more of:
(a) at least one agent known to increase mAChR $M_1$ activity;
(b) at least one agent known to decrease mAChR $M_1$ activity;
(c) at least one agent known to treat a disorder associated with cholinergic activity;
(d) instructions for treating a disorder associated with cholinergic activity;
(e) instructions for treating a disorder associated with $M_1$ receptor activity; or
(f) instructions for administering the compound in connection with cognitive or behavioral therapy.

In some embodiments, the at least one disclosed compound and the at least one agent are co-formulated. In some embodiments, the at least one disclosed compound and the at least one agent are co-packaged. The kits can also comprise compounds and/or products co-packaged, co-formulated, and/or co-delivered with other components. For example, a drug manufacturer, a drug reseller, a physician, a compounding shop, or a pharmacist can provide a kit comprising a disclosed compound and/or product and another component for delivery to a patient.

That the disclosed kits can be employed in connection with disclosed methods of use.

The kits may further comprise information, instructions, or both that use of the kit will provide treatment for medical conditions in mammals (particularly humans). The information and instructions may be in the form of words, pictures, or both, and the like. In addition or in the alternative, the kit may include the compound, a composition, or both; and information, instructions, or both, regarding methods of application of compound, or of composition, preferably with the benefit of treating or preventing medical conditions in mammals (e.g., humans).

The compounds and processes of the invention will be better understood by reference to the following examples, which are intended as an illustration of and not a limitation upon the scope of the invention.

6. Chemical Synthesis

Compounds of formula (I) may be prepared by synthetic processes or by metabolic processes. Preparation of the compounds by metabolic processes includes those occurring in the human or animal body (in vivo) or processes occurring in vitro.

Compounds of formula (I) may be synthesized as shown in General Schemes I and II and Schemes 1-10, as further set forth in the Examples.

The compounds and intermediates may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry," 5th edition (1989), by Furniss, Hannaford, Smith, and Tatchell, pub. Longman Scientific & Technical, Essex CM20 2JE, England.

A disclosed compound may have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Reaction conditions and reaction times for each individual step can vary depending on the particular reactants employed and substituents present in the reactants used. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature. Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in PGM Wuts and TW Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

When an optically active form of a disclosed compound is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as described are illustrative and are not to be read as limiting the scope of the invention as it is defined in the appended claims. All alternatives, modifications, and equivalents of the synthetic methods and specific examples are included within the scope of the claims.

All NMR spectra were recorded on a 400 MHz AMX Bruker NMR spectrometer. $^1$H chemical shifts are reported in δ values in ppm downfield with the deuterated solvent as the internal standard. Data are reported as follows: chemical shift, multiplicity (s=singlet, bs=broad singlet, d=doublet, t=triplet, q=quartet, dd=doublet of doublets, m=multiplet, ABq=AB quartet), coupling constant, integration. Reversed-phase LCMS analysis was performed using an Agilent 1200 system comprised of a binary pump with degasser, high-performance autosampler, thermostatted column compartment, C18 column, diode-array detector (DAD) and an Agilent 6150 MSD with the following parameters. The gradient conditions were 5% to 95% acetonitrile with the aqueous phase 0.1% TFA in water over 1.4 minutes. Samples were separated on a Waters Acquity UPLC BEH C18 column (1.7 μm, 1.0×50 mm) at 0.5 mL/min, with column and solvent temperatures maintained at 55° C. The DAD was set to scan from 190 to 300 nm, and the signals used were 220 nm and 254 nm (both with a band width of 4 nm). The MS detector was configured with an electrospray ionization source, and the low-resolution mass spectra were acquired by scanning from 140 to 700 AMU with a step size of 0.2 AMU at 0.13 cycles/second, and peak width of 0.008 minutes. The drying gas flow was set to 13 liters per minute at 300° C. and the nebulizer pressure was set to 30 psi. The capillary needle voltage was set at 3000 V, and the fragmentor voltage was set at 100V. Data acquisition was performed with Agilent Chemstation and Analytical Studio Reviewer software.

The following abbreviations are used herein:
conc. concentrated
Cpd compound
DCC N,N'-dicyclohexylcarbodiimide
DCM dichloromethane
DIPEA/DIEA diisopropylethylamine
DMF N,N-dimethylformamide
DMSO dimethyl sulfoxide
EDC 1-Ethyl-3-(3-dimethylaminopropyl)carbodiimide
ES-MS electrospray mass spectrometry
EtOAc ethyl acetate
eq equivalents
h or hr hour
HATU 1-[Bis(dimethylamino)methylene]-1H-1,2,3-triazolo[4,5-b]pyridinium 3oxide hexafluorophosphate
HBTU N,N,N',N'-Tetramethyl-O-(1H-benzotriazol-1-yl)uronium hexafluorophosphate
HPLC high performance liquid chromatograph
IPA isopropyl alcohol
KOAc potassium acetate
LCMS liquid chromatography-mass spectrometry
Me methyl
MeOH methanol
mCPBA meta-chloroperoxybenzoic acid
min minutes
Pd(dppf)Cl$_2$ (1,1'-Bis(diphenylphosphino)ferrocene)palladium(II) dichloride
Pd$_2$(dba)$_3$ Tris(dibenzylideneacetone)dipalladium(O)
Pd(OAc)$_2$ palladium(II) acetate
Pd(PPh$_3$)$_4$ Tetrakis(triphenylphosphine)palladium(0)
Pd(PPh$_3$)$_2$Cl$_2$ Bis(triphenylphosphine)palladium(II) dichloride
PPh$_3$ triphenylphosphine
PyBOP (Benzotriazol-1-yloxy)tripyrrolidinophosphonium hexafluorophosphate
Ph phenyl
ppm parts per million
RP reverse phase
r.t./rt/RT room temperature
sat. saturated
TBTU 2-(1H-Benzotriazole-1-yl)-1,1,3,3-tetramethylaminium tetrafluoroborate
THF tetrahydrofuran
TFA trifluoroacetic acid
TMS-CN Trimethylsilyl cyanide

General Scheme I. C-Link Series

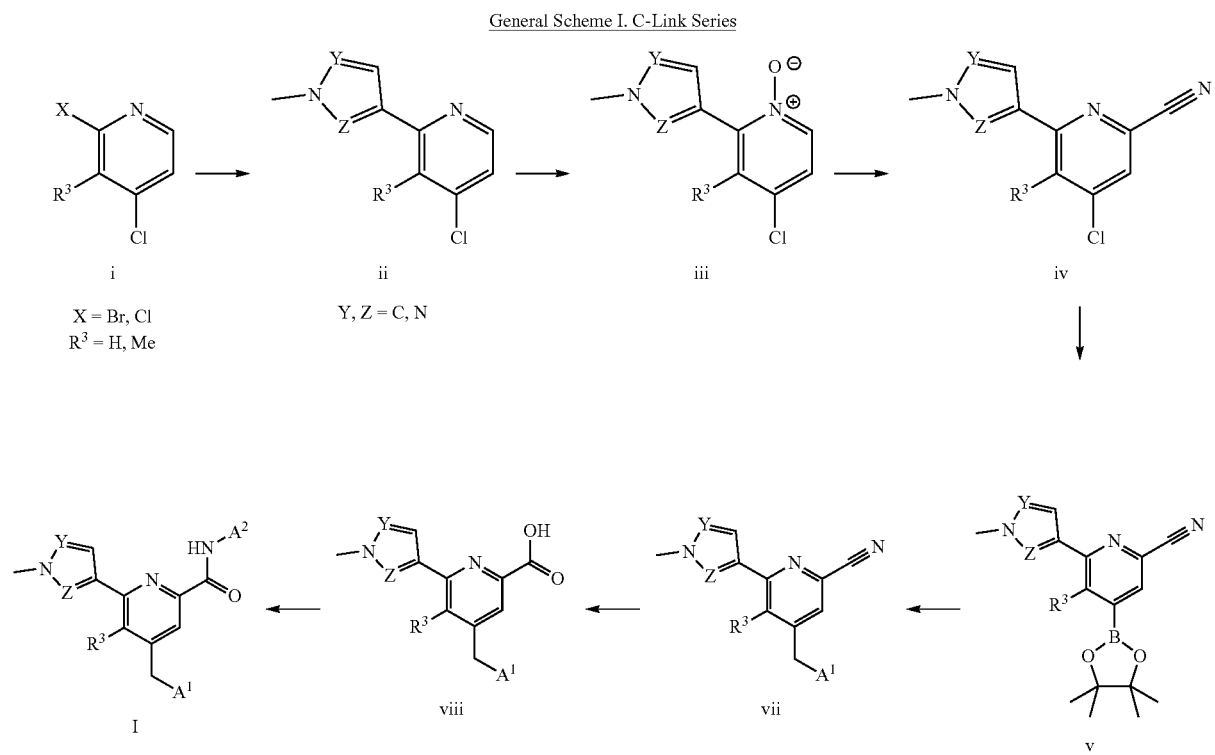

X = Br, Cl
R³ = H, Me

Y, Z = C, N

General Scheme I shows a method for preparing compounds of the invention wherein the ring A³ attaches to the central pyridine ring through a carbon atom of A³. Starting pyridines i may be reacted with suitable boronic acids or esters under Suzuki coupling conditions to provide intermediates ii. Typical Suzuki reaction conditions known to those skilled in the art include heating in an organic solvent in the presence of a catalytic Pd species, such as Pd(PPh₃)₄, Pd(dppf)Cl₂, Pd(PPh₃)₂Cl₂, Pd(OAc)₂, Pd₂(dba)₃ or other such Pd catalyst, and a base such as Na₂CO₃, Cs₂CO₃, K₂CO₃, Ba(OH)₂ or Et₃N. Intermediates ii may be oxidized with mCPBA to the pyridine N-oxides iii, which may be converted to intermediates iv by reaction with dimethylcarbamoyl chloride and trimethylsilyl cyanide. Intermediates iv may be converted to the boronic esters v by reaction with bis(pinacolato)diboron and a Pd catalyst (e.g., Pd(dppf)Cl₂) and a base (e.g., KOAc). Intermediates v may be converted to vii by another Suzuki reaction with a suitable benzyl halide using coupling conditions described herein or standard coupling conditions known to those skilled in the art. Reacting the intermediates vii with concentrated acid (e.g., HCl) at elevated conditions may hydrolyze the nitrile to the corresponding acids viii. Reaction of acids viii with an amine under standard amide bond forming conditions known in the art may be provide compounds of formula (I). Typical coupling conditions include a base (e.g., DIPEA) and a coupling reagent such as HATU, EDC, PyBOP, DCC, HBTU, or TBTU.

Example 1. 5-methyl-6-(1-methyl-1H-pyrazol-3-yl)-4-(4-(1-methyl-1H-pyrazol-3-yl)benzyl)-N-(tetrahydro-2H-pyran-4-yl)picolinamide (Compound 1)

Scheme 1. Synthesis of intermediate ii

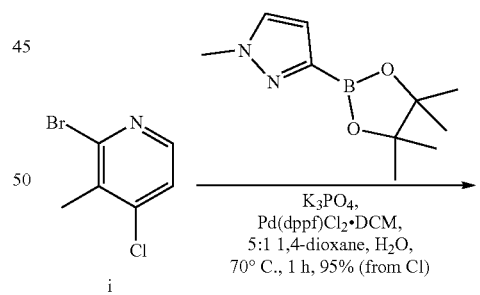

K₃PO₄,
Pd(dppf)Cl₂·DCM,
5:1 1,4-dioxane, H₂O,
70° C., 1 h, 95% (from Cl)

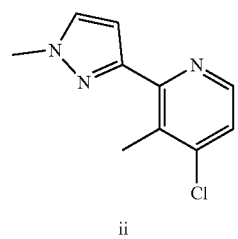

-continued

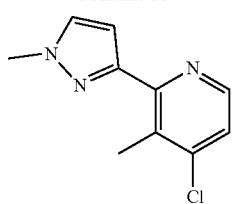

4-chloro-3-methyl-2-(1-methyl-1H-pyrazol-3-yl)pyridine (ii)

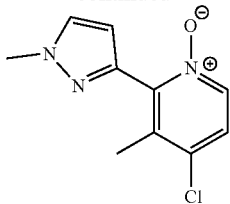

4-chloro-3-methyl-2-(1-methyl-1H-pyrazol-3-yl)pyridine 1-oxide (iii)

2,4-Dichloro-3-picoline (250 mg, 1.54 mmol, 1 eq), 1-methylpyrazole-3-boronic acid pinacol ester (385 mg, 1.85 mmol, 1.2 eq), potassium phosphate tribasic (997 mg, 4.63 mmol, 3 eq), and Pd(dppf)Cl$_2$·DCM (126 mg, 0.15 mmol, 0.1 eq) were charged to a vial which was sealed and evacuated under vacuum and purged with N$_2$. 5:1 1,4-dioxane/H$_2$O solution (10 mL total, degassed) was then added via syringe. The resulting solution was stirred at 70° C. for 1 h, after which time the reaction mixture was cooled to r.t. and filtered through a plug of Celite with EtOAc and DCM. Solvents were concentrated under reduced pressure, and the crude residue was purified by column chromatography (3-70% EtOAc in hexanes) to give the title compound as a slightly brown oil (304 mg, 95%). $^1$H NMR (400 MHz, CDCl$_3$) δ 8.39 (d, J=5.2 Hz, 1H), 7.43 (d, J=2.2 Hz, 1H), 7.26 (d, J=4.6 Hz, 1H), 6.72 (s, 1H), 3.99 (s, 3H), 2.64 (s, 3H). ES-MS [M+H]$^+$=208.4.

Scheme 2. Synthesis of intermediate iv

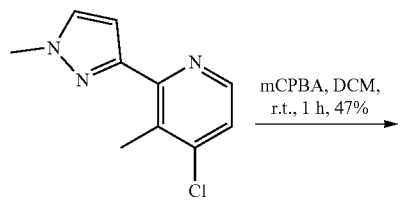

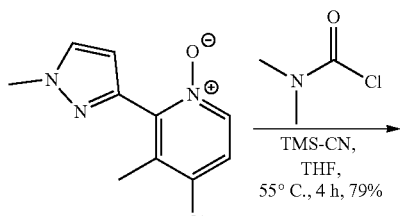

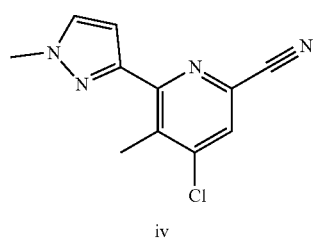

4-Chloro-3-methyl-2-(1-methyl-1H-pyrazol-3-yl)pyridine (300 mg, 1.45 mmol, 1 eq) was dissolved in DCM (7 mL) and mCPBA (648 mg, 2.89 mmol, 2 eq) was added in one portion. The resulting solution was stirred at r.t. for 1 h, after which time sat. NaHCO$_3$ solution was added. The reaction mixture was extracted with DCM and 3:1 chloroform/IPA solution. The combined organic extracts were filtered through a phase separator and concentrated, and the crude residue was purified by column chromatography (3-50% EtOAc in hexanes to 10% MeOH in DCM) to give the title compound as a white solid (153 mg, 47%). $^1$H NMR (400 MHz, CDCl$_3$) δ 8.19 (d, J=7.0 Hz, 1H), 7.51 (d, J=2.3 Hz, 1H), 7.26 (d, J=7.0 Hz, 1H), 6.68 (d, J=2.3 Hz, 1H), 3.98 (s, 3H), 2.32 (s, 3H). ES-MS [M+H]$^+$=224.3.

4-chloro-5-methyl-6-(1-methyl-1H-pyrazol-3-yl)picolinonitrile

4-Chloro-3-methyl-2-(1-methyl-1H-pyrazol-3-yl)pyridine 1-oxide (Intermediate iii, 149.1 mg, 0.67 mmol, 1 eq) was dissolved in THF (3 mL) and placed under an atmosphere of N$_2$. To the solution was added dimethylcarbamoyl chloride (0.12 mL, 1.33 mmol, 2 eq) dropwise. The resulting solution was stirred at r.t. for 10 min, after which time trimethylsilyl cyanide (0.33 mL, 2.67 mmol, 4 eq) was added dropwise. The resulting solution was heated to 55° C. and stirred for 4 h, after which time the reaction mixture was cooled to r.t. and diluted with DCM. 10% w/v K$_2$CO$_3$ solution was added, and the aqueous layer was extracted with DCM and 3:1 chloroform/IPA solution. The combined organic extracts were filtered through a phase separator and concentrated, and the crude residue was purified by column chromatography (3-70% EtOAc in hexanes) to give the title compound as a white solid (122 mg, 79%). $^1$H NMR (400 MHz, CDCl$_3$) δ 7.61 (s, 1H), 7.44 (d, J=2.3 Hz, 1H), 6.84 (d, J=2.3 Hz, 1H), 4.00 (s, 3H), 2.77 (s, 3H). ES-MS [M+H]$^+$=233.4.

Scheme 3. Synthesis of intermediate vii

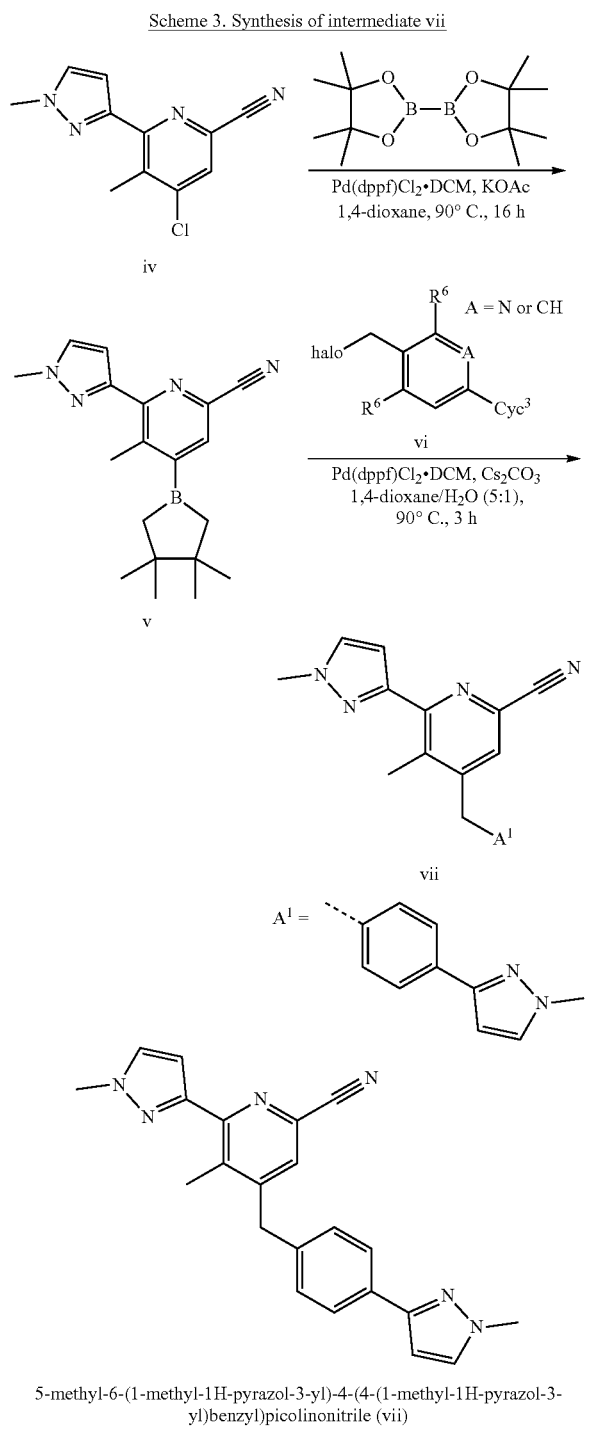

5-methyl-6-(1-methyl-1H-pyrazol-3-yl)-4-(4-(1-methyl-1H-pyrazol-3-yl)benzyl)picolinonitrile (vii)

4-Chloro-5-methyl-6-(1-methyl-1H-pyrazol-3-yl)picolinonitrile (119 mg, 0.52 mmol, 1 eq), bis(pinacolato)diboron (259 mg, 1.02 mmol, 2 eq), potassium acetate (200 mg, 2.04 mmol, 4 eq), and Pd(dppf)Cl$_2$.DCM (42 mg, 0.051 mmol, 0.1 eq) were charged to a vial which was sealed and evacuated under vacuum and purged with N$_2$. 1,4-dioxane (5 mL) was then added via syringe, and the resulting solution was stirred at 90° C. for 6 h, after which time an additional 1 eq bis(pinacolato)diboron, 1 eq potassium acetate, and 0.025 eq Pd(dppf)Cl$_2$.DCM were added. The resulting solution was stirred at 90° C. for 16 h, after which time the reaction mixture was cooled to r.t. and filtered through a plug of Celite with EtOAc and DCM. Solvents were concentrated under reduced pressure to give the pinacol ester intermediate (v) as a brown solid which was used directly without further purification (166 mg, 100%). ES-MS [M+H]$^+$=243.2 (mass of free boronic acid is observed). To a vial containing crude pinacol ester (166 mg, 0.52 mmol, 1 eq), 3-[4-(chloromethyl)phenyl]-1-methyl-pyrazole (169 mg, 0.82 mmol, 1.6 eq), cesium carbonate (502 mg, 1.53 mmol, 3 eq) and Pd(dppf)Cl$_2$.DCM (56 mg, 0.077 mmol, 0.15 eq) were added. The vial was sealed and evacuated under vacuum and purged with N$_2$. 5:1 1,4-dioxane/H$_2$O solution (4 mL total, degassed) was then added via syringe and the resulting solution was stirred at 90° C. for 3 h, after which time the reaction mixture was cooled to r.t. and filtered through a plug of Celite with EtOAc and DCM. Solvents were concentrated under reduced pressure, and crude residue was purified by column chromatography (5-100% EtOAc in hexanes) to give the title compound as a slightly yellow foamy solid (126 mg, 67%). $^1$H NMR (400 MHz, CDCl$_3$) δ 7.76 (d, J=8.1 Hz, 2H), 7.43 (s, 1H), 7.38 (d, J=1.8 Hz, 1H), 7.32 (s, 1H), 7.14 (d, J=8.0 Hz, 2H), 6.75 (s, 1H), 6.53 (d, J=1.8 Hz, 1H), 4.07 (s, 2H), 3.98 (s, 3H), 3.96 (s, 3H), 2.59 (s, 3H). ES-MS [M+H]$^+$=369.2.

Scheme 4. Synthesis of intermediate viii

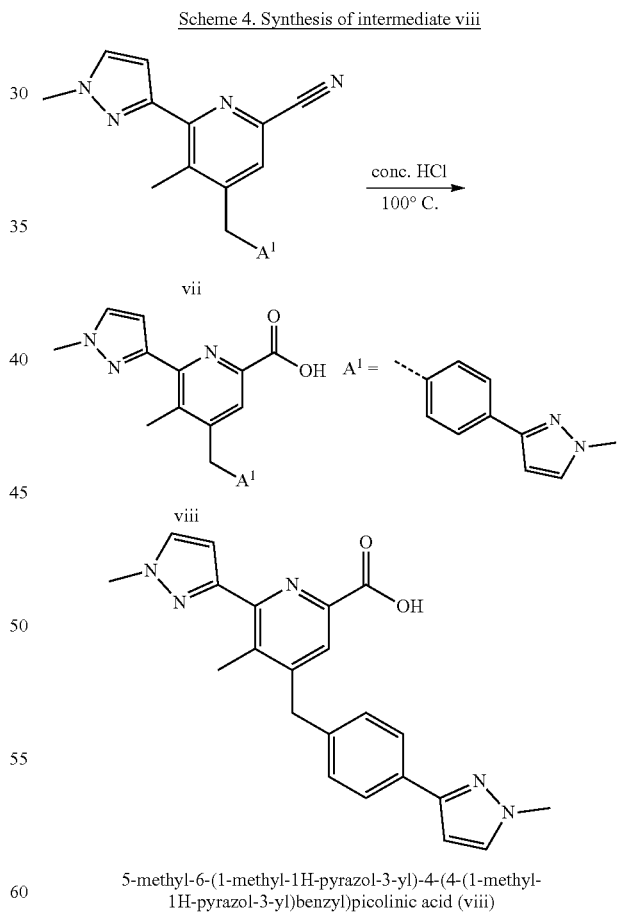

5-methyl-6-(1-methyl-1H-pyrazol-3-yl)-4-(4-(1-methyl-1H-pyrazol-3-yl)benzyl)picolinic acid (viii)

5-Methyl-6-(1-methyl-1H-pyrazol-3-yl)-4-(4-(1-methyl-1H-pyrazol-3-yl)benzyl)picolinonitrile (Intermediate vii, 122 mg, 0.33 mmol) was dissolved in conc. HCl solution (2 mL) and stirred at 100° C. for 2 h, after which time the reaction mixture was cooled to r.t. and concentrated under reduced pressure to give the carboxylic acid as a slightly yellow solid that was dried under vacuum and used without further purification (140 mg, 100%) as the HCl salt. ES-MS [M+H]⁺=388.5.

Scheme 5. Synthesis of the compound of formula (I)

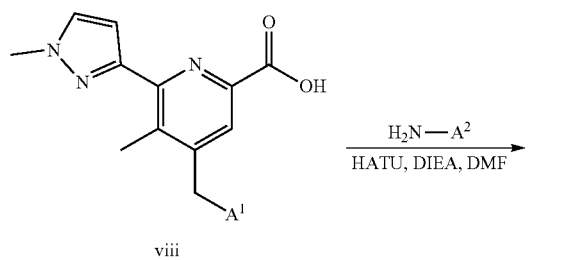

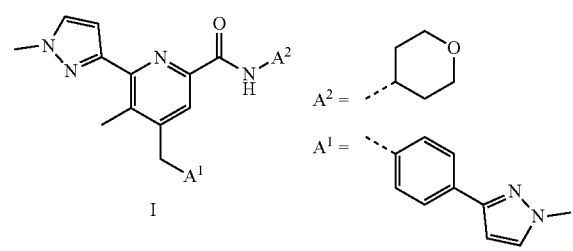

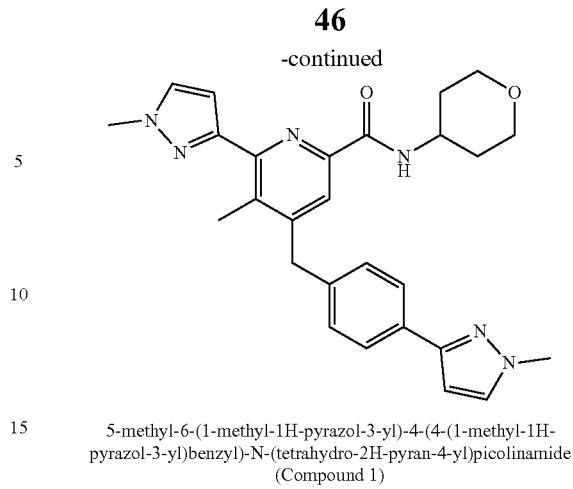

5-methyl-6-(1-methyl-1H-pyrazol-3-yl)-4-(4-(1-methyl-1H-pyrazol-3-yl)benzyl)-N-(tetrahydro-2H-pyran-4-yl)picolinamide
(Compound 1)

5-Methyl-6-(1-methyl-1H-pyrazol-3-yl)-4-(4-(1-methyl-1H-pyrazol-3-yl)benzyl)picolinic acid (14 mg, 0.033 mmol, 1 eq) was dissolved in DMF (1 mL), and DIPEA (0.029 mL, 0.17 mmol, 5 eq) was added, followed by 4-oxanamine (5 mg, 0.050 mmol, 1.5 eq) and HATU (25 mg, 0.066 mmol, 2 eq). The resulting solution was stirred at r.t. for 1 h, after which time the reaction mixture was purified directly by RP-HPLC. Fractions containing product were basified with sat. NaHCO₃, and extracted with 3:1 chloroform/IPA. Combined organic extracts were filtered through a phase separator and concentrated to give the title compound as a colorless oil (6.4 mg, 41%). ¹H NMR (400 MHz, CDCl₃) δ 8.05 (d, J=8.2 Hz, 1H), 8.01 (s, 1H), 7.69 (d, J=8.2 Hz, 2H), 7.44 (d, J=2.2 Hz, 1H), 7.35 (d, J=2.2 Hz, 1H), 7.14 (d, J=8.2 Hz, 2H), 6.65 (d, J=2.2 Hz, 1H), 6.49 (d, J=2.3 Hz, 1H), 4.24-4.11 (m, 1H), 4.12 (s, 2H), 4.02-3.97 (m, 2H), 3.99 (s, 3H), 3.94 (s, 3H), 3.55 (td, J=11.6, 2.0 Hz, 2H), 2.48 (s, 3H), 2.02-1.95 (m, 2H), 1.70-1.60 (m, 2H). ES-MS [M+H]⁺=471.4.

General Scheme II. N-Link Series

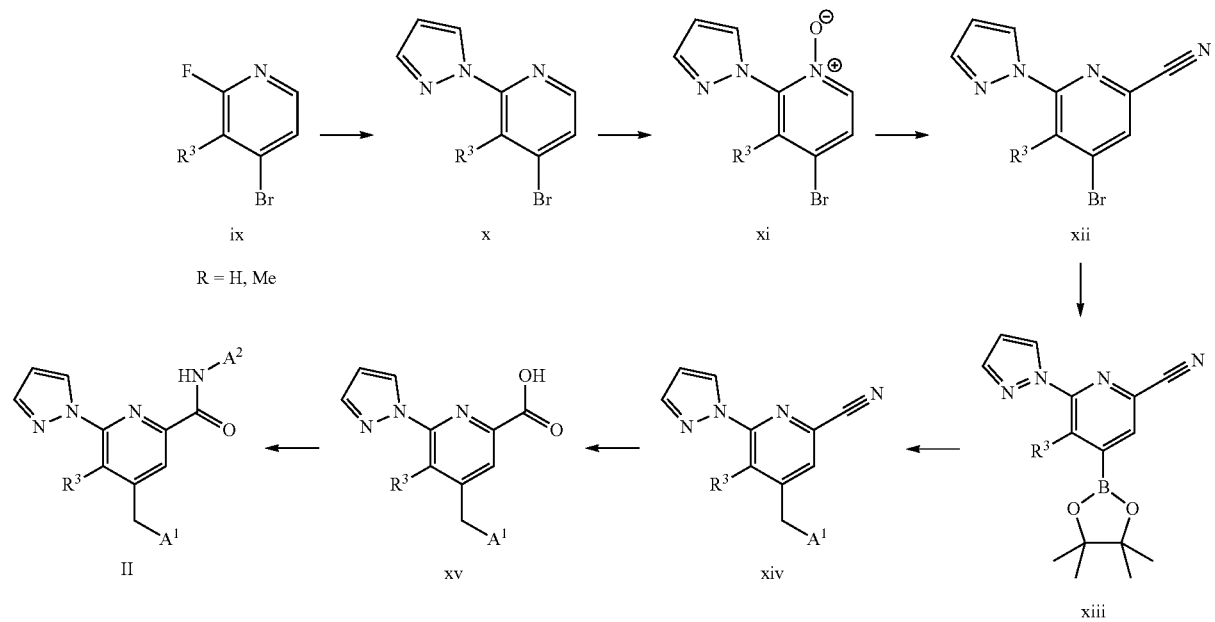

General Scheme II shows a method for preparing compounds of the invention wherein the ring $A^3$ attaches to the central pyridine ring through a nitrogen atom of $A^3$. Starting fluoropyridines ix may be reacted with suitable NH-containing heteroaryl reagents in the presence of base (e.g., $K_2CO_3$) through a SNAr reaction to provide x. Intermediates x may be oxidized with mCPBA to the pyridine N-oxides xi, which may be converted to intermediates xii by reaction with dimethylcarbamoyl chloride and trimethylsilyl cyanide. Intermediates xii may be converted to the boronic esters xiii by reaction with bis(pinacolato)diboron and a Pd catalyst (e.g., $Pd(dppf)Cl_2$) and a base (e.g., KOAc). Intermediates xiii may be converted to xiv by a Suzuki reaction with a suitable benzyl halide using coupling conditions described herein or standard coupling conditions known to those skilled in the art. Reacting the intermediates xiv with concentrated acid (e.g., HCl) at elevated conditions may hydrolyze the nitrile to the corresponding acids xv. Reaction of acids xv with an amine under standard amide bond forming conditions known in the art may be provide compounds of formula (II). Typical coupling conditions include a base (e.g., DIPEA) and a coupling reagent such as HATU, EDC, PyBOP, DCC, HBTU, or TBTU.

Example 2. N-((3R,4S)-3-hydroxytetrahydro-2H-pyran-4-yl)-5-methyl-4-(4-(1-methyl-1H-pyrazol-3-yl)benzyl)-6-(1H-pyrazol-1-yl)picolinamide (Compound 2)

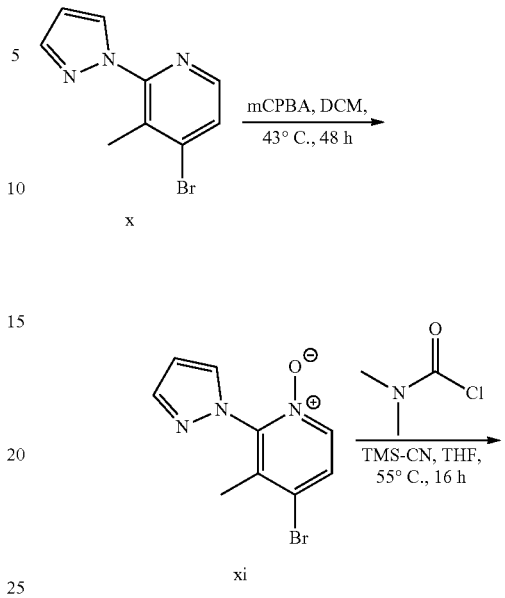

Scheme 7. Synthesis of intermediate xii 4-bromo-3-methyl-2-(1H-pyrazol-1-yl)pyridine 1-oxide (xi)

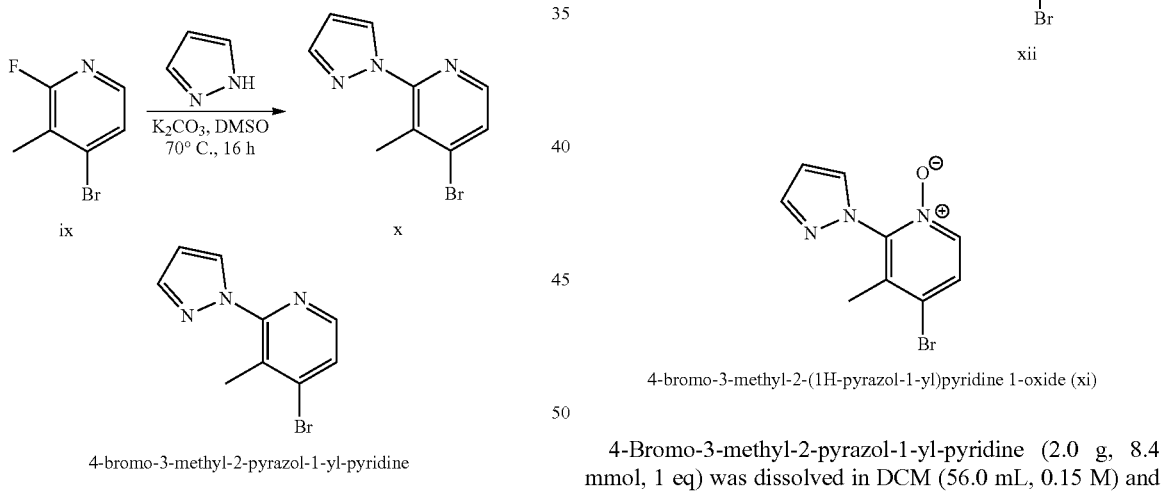

Scheme 6 - Synthesis of intermediate x 4-bromo-3-methyl-2-pyrazol-1-yl-pyridine

A mixture of 4-bromo-2-fluoro-3-picoline (1.90 g, 10 mmol, 1.0 eq), pyrazole (1.36 g, 20 mmol, 2.0 eq) and potassium carbonate (2.80 g, 20 mmol, 2.0 eq) in DMSO (20 mL, 0.5 M) was stirred at 70° C. After 16 h, the reaction mixture was added to brine and extracted with EtOAc (3×). The combined extracts were washed with brine, dried ($MgSO_4$), filtered and concentrated. The crude material was purified using chromatography on silica gel (0-50% EtOAc/hexanes) to provide the title compound as a white crystalline solid (2.23 g, 94%). $^1$H NMR (400 MHz, $CDCl_3$) δ 8.12 (d, J=5.1 Hz, 1H), 8.09 (d, J=2.2 Hz, 1H), 7.75 (d, J=1.3 Hz, 1H), 7.51 (d, J=5.2 Hz, 1H), 6.45 (dd, J=2.3, 1.9 Hz, 1H), 2.56 (s, 3H). ES-MS [M+H]$^+$=238.3.

4-Bromo-3-methyl-2-pyrazol-1-yl-pyridine (2.0 g, 8.4 mmol, 1 eq) was dissolved in DCM (56.0 mL, 0.15 M) and m-CPBA (3.76 mg, 16.8 mmol, 2 eq) was added in one portion. The resulting solution was stirred at 43° C. After 16 h, another portion of m-CPBA (3.76 mg, 16.8 mmol, 2 eq) was added. The mixture was allowed to stir at 43° C. for 16 h after which time sat. $NaHCO_3$ solution was added. The reaction mixture was extracted with DCM and 3:1 chloroform/IPA solution. Combined organic extracts were dried over $Na_2SO_4$, filtered and concentrated. The crude residue was purified by column chromatography (0-40% EtOAc in hexanes to 40-80% EtOAc/DCM then 50% MeOH/$NH_4$OH/DCM 10:1:89 mixture) to give the title compound as an off white powder (1.65 g, 78%). $^1$H NMR (400 MHz, $CDCl_3$) δ 8.08 (d, J=7.0 Hz, 1H), 7.84 (bs, 2H), 7.54 (d, J=7.0 Hz, 1H), 6.56 (bs, 1H), 2.21 (s, 3H). ES-MS [M+H]$^+$=254.3.

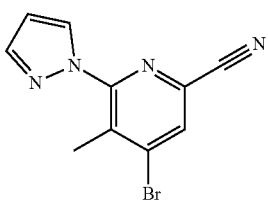

4-bromo-5-methyl-6-
(1H-pyrazol-1-yl)picolinonitrile
(xii)

4-Bromo-3-methyl-2-(1H-pyrazol-1-yl)pyridine 1-oxide (Intermediate xi, 1.65 g, 6.5 mmol, 1 eq) was dissolved in THF (43.4 mL, 0.15 M) and placed under an atmosphere of $N_2$. To the solution was added dimethylcarbamoyl chloride (1.80 mL, 19.54 mmol, 3 eq) dropwise. The resulting solution was stirred at r.t. for 10 min, after which time trimethylsilyl cyanide (2.44 mL, 19.54 mmol, 3 eq) was added dropwise. The resulting solution was heated to 65° C. After 16 h, the reaction mixture was cooled to r.t. and diluted with DCM. 10% w/v $K_2CO_3$ solution was added, and the aqueous layer was extracted with EtOAc (3×). Combined organic extracts were dried over $MgSO_4$, filtered and concentrated. The crude material was purified by column chromatography (0-30% EtOAc in hexanes) to give the title compound as solid (820 mg, 48%). Impurities present. The mixture was carried forwards as is. ES-MS [M+H]$^+$=265.2.

Scheme 8. Synthesis of intermediate xiii

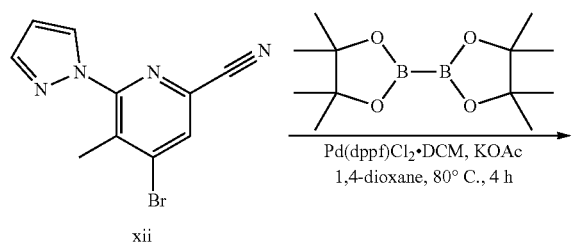

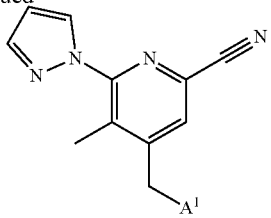

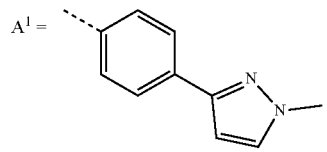

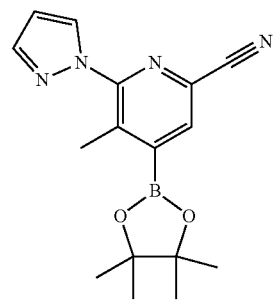

5-methyl-6-(1H-pyrazol-1-yl)-4-(4,4,5,5-
tetramethyl-1,3,2-dioxaborolan-2-yl)
picolinonitrile
(xiii)

4-Bromo-5-methyl-6-(1H-pyrazol-1-yl)picolinonitrile (820 mg, 3.12 mmol, 1 eq), bis(pinacolato)diboron (1.19 g, 4.68 mmol, 1.5 eq), potassium acetate (917 mg, 9.35 mmol, 3 eq), and Pd(dppf)Cl$_2$.DCM (191 mg, 0.233 mmol, 0.075 eq) were charged into a vial which was sealed and evacuated under vacuum and purged with $N_2$. 1,4-dioxane (15.5 mL, 0.2 M) was then added via syringe, and the resulting solution was stirred at 80° C. After 4 h, the reaction mixture was cooled to r.t. and filtered through a plug of Celite with EtOAc and DCM. Solvents were concentrated under reduced pressure to give the crude material as a brown solid. Purification using column chromatography on silica gel (0-50% EtOAc/hexanes) to give the pinacol ester intermediate (xiii) as an off white solid (750 mg, 78%). ES-MS [M+H]$^+$=229.4 (mass of free boronic acid is observed).

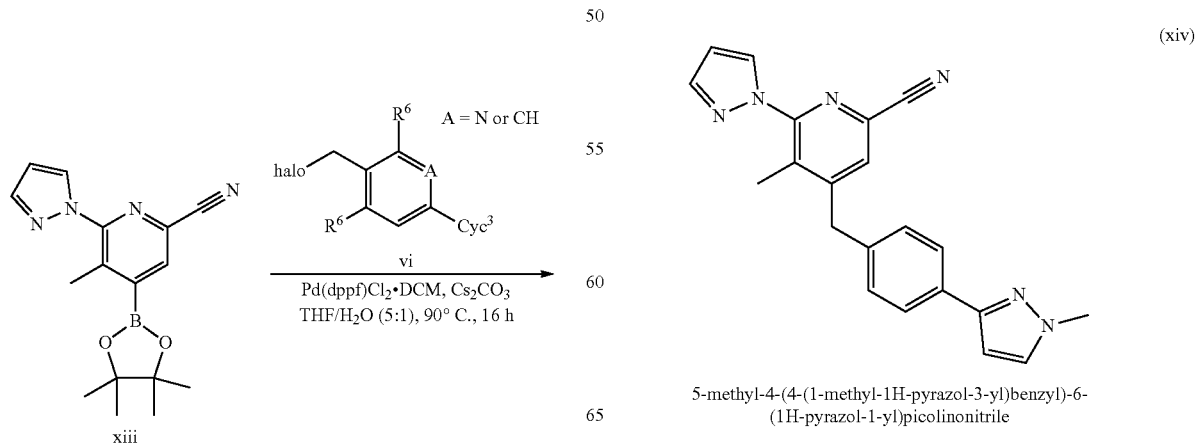

5-methyl-4-(4-(1-methyl-1H-pyrazol-3-yl)benzyl)-6-
(1H-pyrazol-1-yl)picolinonitrile To a vial containing pinacol ester (200 mg, 0.645 mmol, 1 eq), 3-[4-(chloromethyl)phenyl]-1-methyl-pyrazole (200 mg, 0.97 mmol, 1.5 eq), cesium carbonate (315 mg, 0.97 mmol, 1.5 eq) and Pd(dppf)Cl$_2$·DCM (71 mg, 0.097 mmol, 0.15 eq) were added. The vial was sealed and evacuated under vacuum and purged with N$_2$. THF/H$_2$O solution (5:1, 5.2 mL total, degassed) was then added via syringe and the resulting solution was stirred at 90° C. for 16 h, after which time the reaction mixture was cooled to r.t. and filtered through a plug of Celite with EtOAc and DCM. Solvents were concentrated under reduced pressure, and crude residue was purified by reverse phase HPLC then by normal phase column chromatography (0-70% EtOAc in hexanes to 70-80% EtOAc/DCM) to give the title compound as an off white powder (72 mg, 32%). $^1$H NMR (400 MHz, CDCl$_3$) δ 8.18 (d, J=2.5 Hz, 1H), 7.78 (d, J=8.2 Hz, 2H), 7.76 (d, J=1.3 Hz, 1H), 7.39 (d, J=2.2 Hz, 1H), 7.36 (s, 1H), 7.15 (d, J=8.2 Hz, 2H), 6.53 (d, J=2.3 Hz, 1H), 6.47 (dd, J=2.4, 1.9 Hz, 1H), 4.11 (s, 2H), 3.96 (s, 3H), 2.54 (s, 3H). ES-MS [M+H]$^+$=355.4.

Scheme 9. Synthesis of intermediate xv

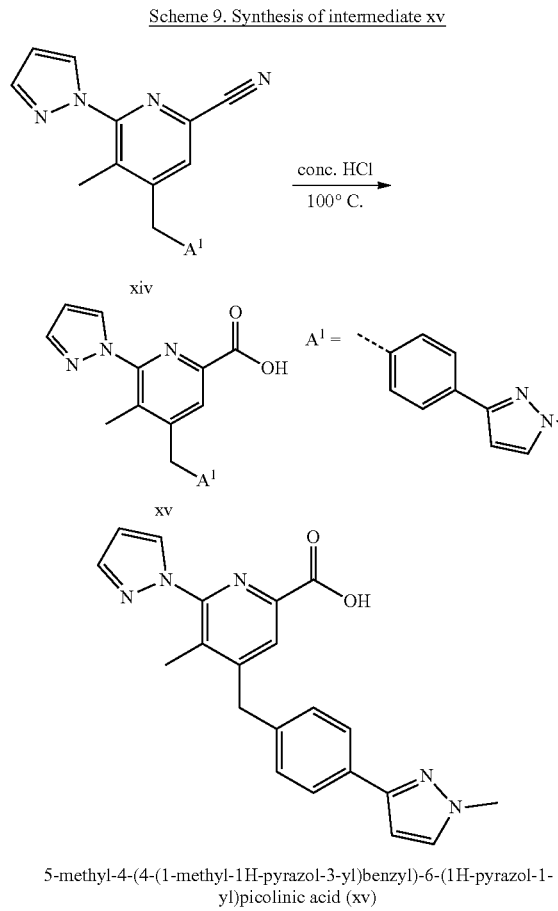

5-methyl-4-(4-(1-methyl-1H-pyrazol-3-yl)benzyl)-6-(1H-pyrazol-1-yl)picolinic acid (xv)

5-Methyl-4-(4-(1-methyl-1H-pyrazol-3-yl)benzyl)-6-(1H-pyrazol-1-yl)picolinonitrile (72 mg, 0.20 mmol, 1.0 eq) was suspended in conc. HCl solution (2 mL) and stirred at 100° C. for 2 h, after which time the reaction mixture was cooled to r.t. and concentrated under reduced pressure to give the carboxylic acid as a slightly yellow solid was dried under vacuum and used without further purification (75.9 mg, quantitative yield) as the HCl salt. $^1$H NMR (400 MHz, DMSO-d$_6$) δ 8.29 (dd, J=2.4, 0.5 Hz, 1H), 7.89 (s, 1H), 7.79 (dd, J=2.4, 0.5 Hz, 1H), 7.75 (d, J=8.2 Hz, 2H), 7.73 (d, J=2.2 Hz, 1H), 7.26 (d, J=8.2 Hz, 2H), 6.66 (d, J=2.3 Hz, 1H), 6.55 (dd, J=2.4, 1.9 Hz, 1H), 4.22 (s, 2H), 3.88 (s, 3H), 2.31 (s, 3H). (COOH proton not observed). ES-MS [M+H]$^+$=374.5.

Scheme 10. Synthesis of the compound formula (II)

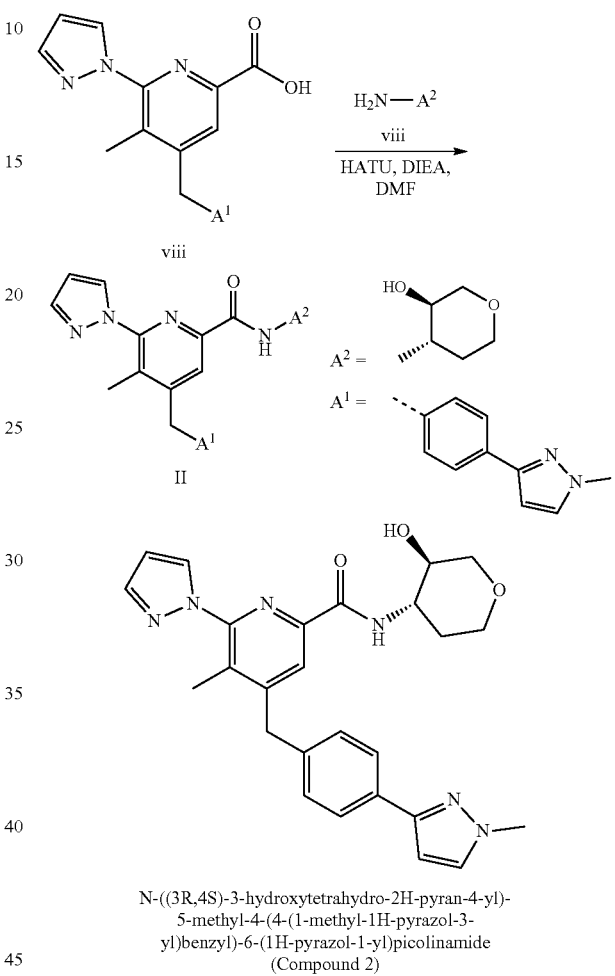

N-((3R,4S)-3-hydroxytetrahydro-2H-pyran-4-yl)-5-methyl-4-(4-(1-methyl-1H-pyrazol-3-yl)benzyl)-6-(1H-pyrazol-1-yl)picolinamide
(Compound 2)

5-Methyl-4-(4-(1-methyl-1H-pyrazol-3-yl)benzyl)-6-(1H-pyrazol-1-yl)picolinic acid (8.0 mg, 0.02 mmol, 1 eq) was dissolved in DMF (1 mL), and DIPEA (0.024 mL, 0.12 mmol, 6 eq) was added, followed by (3R,4S)-4-aminotetrahydropyran-3-ol (as a (2R)-2-acetamido-3-phenyl-propanoic acid salt, 12.7 mg, 0.039 mmol, 2.0 eq) and HATU (25 mg, 0.066 mmol, 2 eq). The resulting solution was stirred at r.t. for 20 min, after which time the reaction mixture was purified directly by RP-HPLC. The desired fractions were concentrated to provide the title compound as an off white solid (3.9 mg, 42%). $^1$H NMR (400 MHz, CDCl$_3$) δ 8.07 (s, 1H), 7.96 (d, J=2.4 Hz, 1H), 7.88 (d, J=6.6 Hz, 1H), 7.77 (d, J=1.3 Hz, 1H), 7.72 (d, J=8.3 Hz, 2H), 7.36 (d, J=2.2 Hz, 1H), 7.15 (d, J=8.2 Hz, 2H), 6.50-6.49 (m, 2H), 4.16-4.15 (m, 3H, benzyl CH$_2$ and OH), 4.07 (dd, J=11.0, 5.0 Hz, 1H), 3.98-3.90 (m, 5H), 3.65-3.58 (m, 1H), 3.45 (ddd, J=11.9, 2.2, 2.2, 1H), 3.21 (dd, J=11.3, 10.0, 1H), 2.33 (s, 3H), 2.02-1.98 (m, 1H), 1.79-1.67 (m, 1H). ES-MS [M+H]$^+$=473.0.

Example 3. Additional Compounds

The compounds presented in Table 1 may be prepared in an analogous manner to those described in General Schemes I or II, Examples 1-2 and/or Schemes 1-10 using appropriate starting materials. Exemplary starting materials that may be used in the boronic acid coupling step of the foregoing procedures include, but are not limited to, 1-(4-(chloromethyl)phenyl)-1H-pyrazole (CAS #143426-52-2; ChemBridge Corporation), 5-(bromomethyl)-2-methylpyridine Hydrobromide (CAS #718608-10-7; Combi-Blocks, Inc.), 4-(4-(CHLOROMETHYL)PHENYL)-2-METHYLOXAZOLE (CAS #1859084-44-8 AstaTech, Inc.), 5-(chloromethyl)-2-(1-methyl-H-pyrazol-4-yl)pyridine, (CAS #1392081-39-8; ACS Med. Chem. Lett. 2018, 9, 917-922) and 5-(chloromethyl)-2-(1-methyl-H-pyrazol-3-yl)pyridine, (CAS #2247999-38-6; WO 2018235838).

TABLE 1

| Cpd. No. | Name | Structure | ES-MS [M + 1]+ |
|---|---|---|---|
| 3 | N-((1S,2S)-2-hydroxycyclohexyl)-6-(1-methyl-1H-pyrazol-3-yl)-4-((6-(1-methyl-1H-pyrazol-4-yl)pyridin-3-yl)methyl)picolinamide | 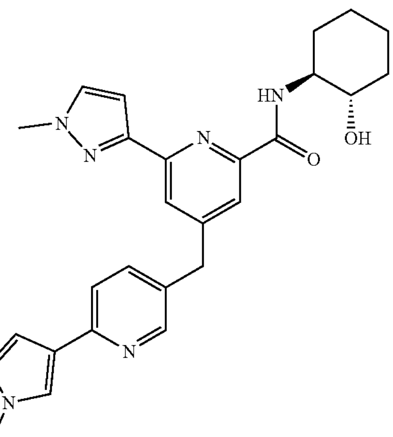 | 472.4 |
| 4 | 6-(1-methyl-1H-pyrazol-3-yl)-4-((6-(1-methyl-1H-pyrazol-4-yl)pyridin-3-yl)methyl)-N-(tetrahydro-2H-pyran-4-yl)picolinamide | 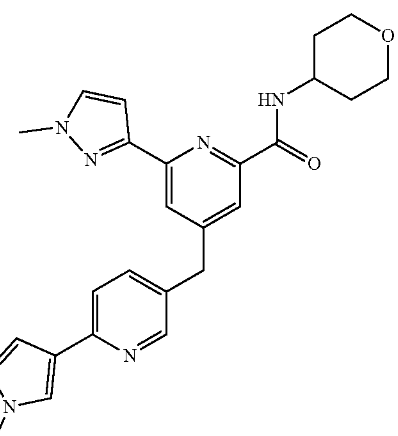 | 458.4 |
| 5 | 6-(1-methyl-1H-pyrazol-3-yl)-4-((6-(1-methyl-1H-pyrazol-4-yl)pyridin-3-yl)methyl)-N-(2-oxaspiro[3.3]heptan-6-yl)picolinamide | 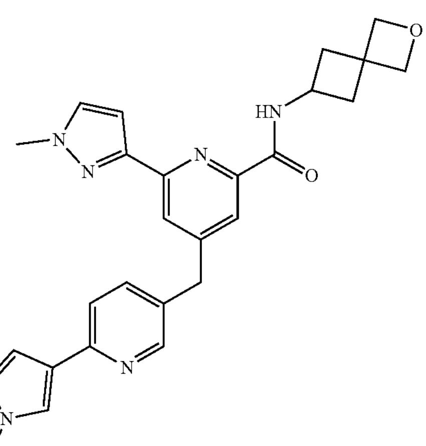 | 470.4 |

TABLE 1-continued

| Cpd. No. | Name | Structure | ES-MS [M + 1]+ |
|---|---|---|---|
| 6 | N-((1S,2S)-2-hydroxycyclopentyl)-6-(1-methyl-1H-pyrazol-3-yl)-4-((6-(1-methyl-1H-pyrazol-4-yl)pyridin-3-yl)methyl)picolinamide | 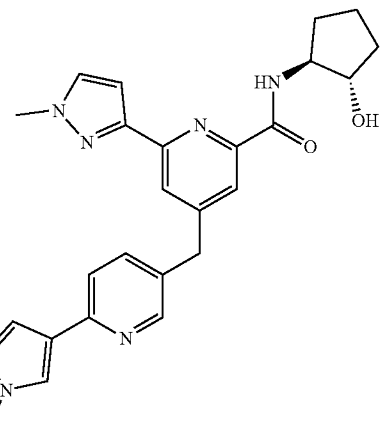 | 458.4 |
| 7 | (S)-6-(1-methyl-1H-pyrazol-3-yl)-4-((6-(1-methyl-1H-pyrazol-4-yl)pyridin-3-yl)methyl)-N-((tetrahydrofuran-2-yl)methyl)picolinamide | 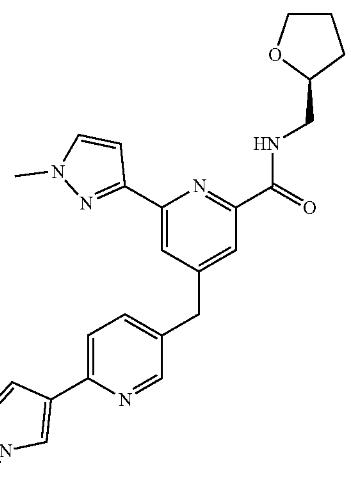 | 458.4 |
| 8 | N-(3,3-dimethyltetrahydro-2H-pyran-4-yl)-6-(1-methyl-1H-pyrazol-3-yl)-4-((6-(1-methyl-1H-pyrazol-4-yl)pyridin-3-yl)methyl)picolinamide | 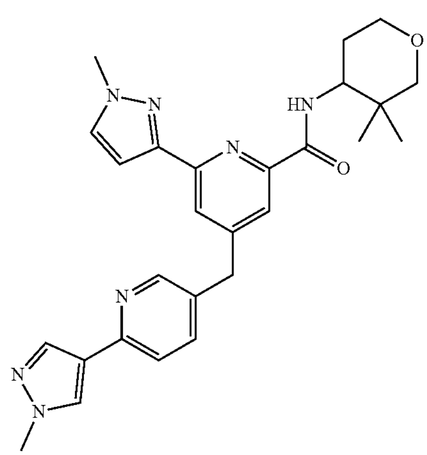 [SMILES: Cn1cc(-c2ccc(Cc3cc(C(=O)NC4CCOCC4(C)C)nc(-c4ccn(C)n4)c3)cn2)cn1] | 486.4 |

TABLE 1-continued

| Cpd. No. | Name | Structure | ES-MS [M + 1]+ |
|---|---|---|---|
| 9 | N-((3R,4S)-3-hydroxytetrahydro-2H-pyran-4-yl)-5-methyl-6-(1-methyl-1H-pyrazol-3-yl)-4-(4-(1-methyl-1H-pyrazol-3-yl)benzyl)picolinamide | 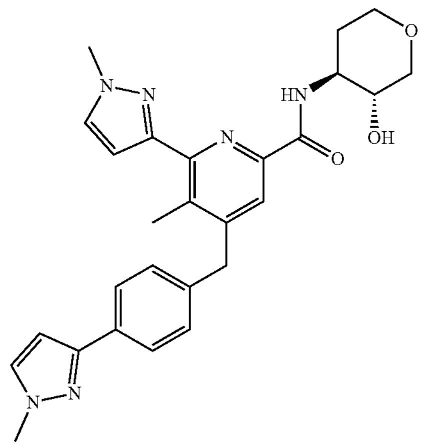 [SMILES: Cc1c(Cc2ccc(-c3ccn(C)n3)cc2)cc(C(=O)N[C@H]2CCOC[C@@H]2O)nc1-c1ccn(C)n1] | 487.4 |
| 10 | N-((1S,2S)-2-hydroxycyclohexyl)-5-methyl-6-(1-methyl-1H-pyrazol-3-yl)-4-(4-(1-methyl-1H-pyrazol-3-yl)benzyl)picolinamide | 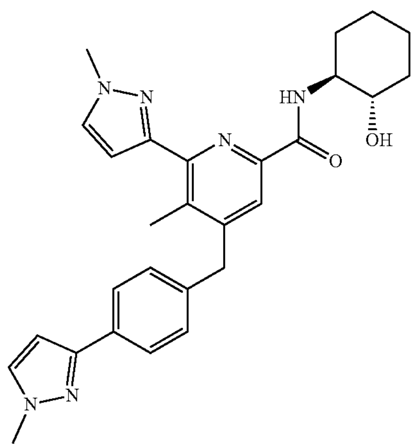 [SMILES: Cc1c(Cc2ccc(-c3ccn(C)n3)cc2)cc(C(=O)N[C@H]2CCCC[C@@H]2O)nc1-c1ccn(C)n1] | 485.5 |
| 11 | 5-methyl-6-(1-methyl-1H-pyrazol-3-yl)-4-(4-(1-methyl-1H-pyrazol-3-yl)benzyl)-N-(2-oxaspiro[3.3]heptan-6-yl)picolinamide | 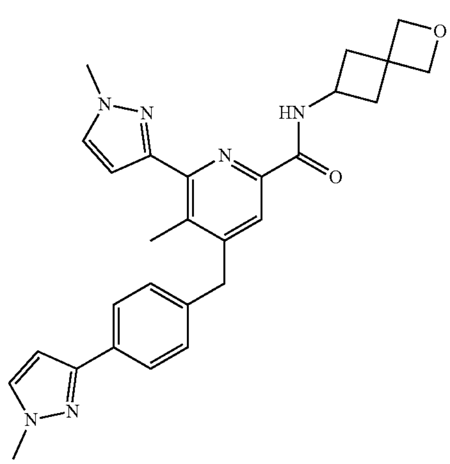 [SMILES: Cc1c(Cc2ccc(-c3ccn(C)n3)cc2)cc(C(=O)NC2CC3(COC3)C2)nc1-c1ccn(C)n1] | 483.5 |

TABLE 1-continued

| Cpd. No. | Name | Structure | ES-MS [M + 1]+ |
|---|---|---|---|
| 12 | N-((1S,2S)-2-hydroxycyclopentyl)-5-methyl-6-(1-methyl-1H-pyrazol-3-yl)-4-(4-(1-methyl-1H-pyrazol-3-yl)benzyl)picolinamide | 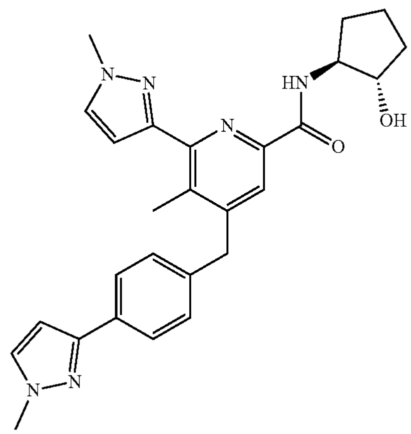 [SMILES: Cc1c(Cc2ccc(-c3ccn(C)n3)cc2)cc(C(=O)N[C@H]2CCC[C@@H]2O)nc1-c1ccn(C)n1] | 471.4 |
| 13 | N-((1S,2S)-2-hydroxycyclobutyl)-5-methyl-6-(1-methyl-1H-pyrazol-3-yl)-4-(4-(1-methyl-1H-pyrazol-3-yl)benzyl)picolinamide | 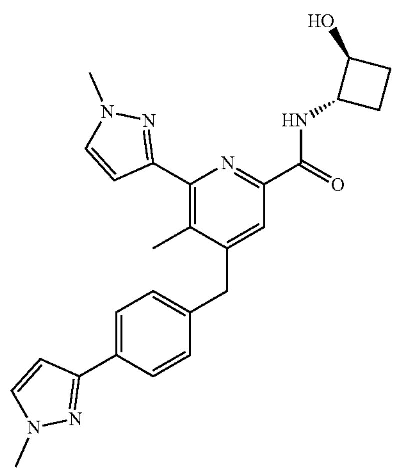 [SMILES: Cc1c(Cc2ccc(-c3ccn(C)n3)cc2)cc(C(=O)N[C@H]2CC[C@@H]2O)nc1-c1ccn(C)n1] | 457.4 |
| 14 | 5-methyl-6-(1-methyl-1H-pyrazol-3-yl)-4-(4-(1-methyl-1H-pyrazol-3-yl)benzyl)-N-((tetrahydro-2H-pyran-4-yl)methyl)picolinamide | 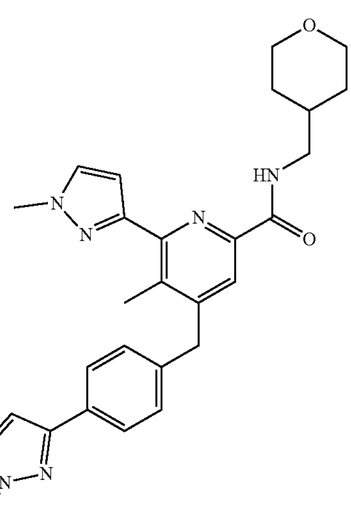 | 485.4 |

TABLE 1-continued

| Cpd. No. | Name | Structure | ES-MS [M + 1]+ |
|---|---|---|---|
| 15 | (S)-5-methyl-6-(1-methyl-1H-pyrazol-3-yl)-4-(4-(1-methyl-1H-pyrazol-3-yl)benzyl)-N-((tetrahydrofuran-2-yl)methyl)picolinamide | 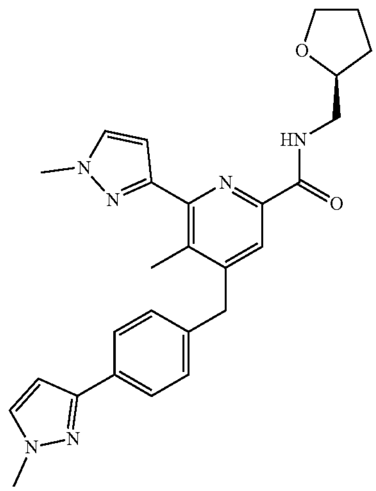 [SMILES: Cc1c(Cc2ccc(-c3ccn(C)n3)cc2)cc(C(=O)NC[C@@H]2CCCO2)nc1-c1ccn(C)n1] | 471.4 |
| 16 | (R)-5-methyl-6-(1-methyl-1H-pyrazol-3-yl)-4-(4-(1-methyl-1H-pyrazol-3-yl)benzyl)-N-((tetrahydrofuran-2-yl)methyl)picolinamide | 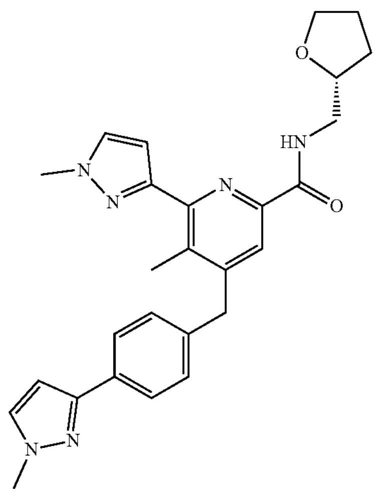 [SMILES: Cc1c(Cc2ccc(-c3ccn(C)n3)cc2)cc(C(=O)NC[C@H]2CCCO2)nc1-c1ccn(C)n1] | 471.4 |
| 17 | N-(3,3-dimethyltetrahydro-2H-pyran-4-yl)-5-methyl-6-(1-methyl-1H-pyrazol-3-yl)-4-(4-(1-methyl-1H-pyrazol-3-yl)benzyl)picolinamide | 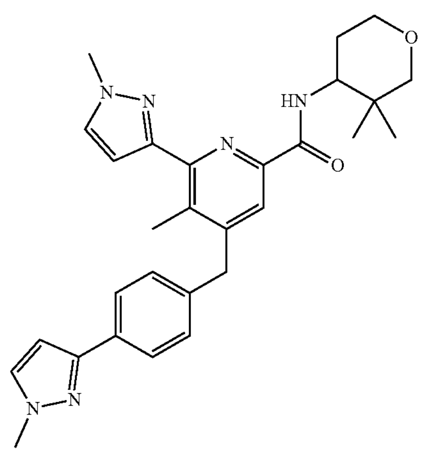 [SMILES: Cc1c(Cc2ccc(-c3ccn(C)n3)cc2)cc(C(=O)NC2CCOCC2(C)C)nc1-c1ccn(C)n1] | 499.4 |

TABLE 1-continued

| Cpd. No. | Name | Structure | ES-MS [M + 1]+ |
|---|---|---|---|
| 18 | N-((3R,4S)-3-hydroxytetrahydro-2H-pyran-4-yl)-4-((6-(1-methyl-1H-pyrazol-4-yl)pyridin-3-yl)methyl)-6-(1H-pyrazol-1-yl)picolinamide | 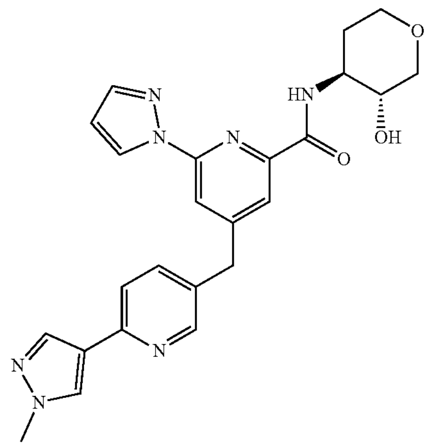 [SMILES: Cn1cc(-c2ccc(Cc3cc(C(=O)N[C@H]4CCOC[C@@H]4O)nc(-n4cccn4)c3)cn2)cn1] | 460.4 |
| 19 | N-((3R,4S)-3-hydroxytetrahydro-2H-pyran-4-yl)-4-(4-(2-methyloxazol-4-yl)benzyl)-6-(1H-pyrazol-1-yl)picolinamide | 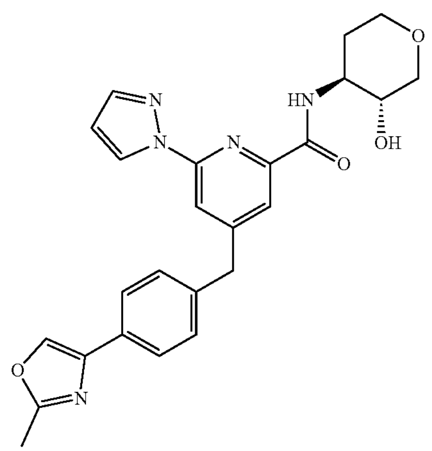 [SMILES: Cc1nc(-c2ccc(Cc3cc(C(=O)N[C@H]4CCOC[C@@H]4O)nc(-n4cccn4)c3)cc2)co1] | 460.4 |
| 20 | N-((1S,2S)-2-hydroxycyclohexyl)-4-((6-(1-methyl-1H-pyrazol-4-yl)pyridin-3-yl)methyl)-6-(1H-pyrazol-1-yl)picolinamide | 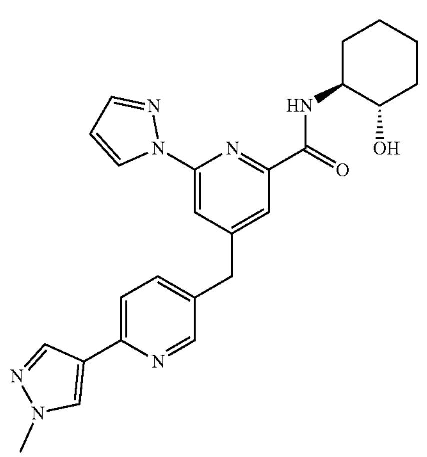 [SMILES: Cn1cc(-c2ccc(Cc3cc(C(=O)N[C@H]4CCCC[C@@H]4O)nc(-n4cccn4)c3)cn2)cn1] | 458.2 |

TABLE 1-continued

| Cpd. No. | Name | Structure | ES-MS [M + 1]+ |
|---|---|---|---|
| 21 | 4-((6-(1-methyl-1H-pyrazol-4-yl)pyridin-3-yl)methyl)-6-(1H-pyrazol-1-yl)-N-(2-oxaspiro[3.3]heptan-6-yl)picolinamide | 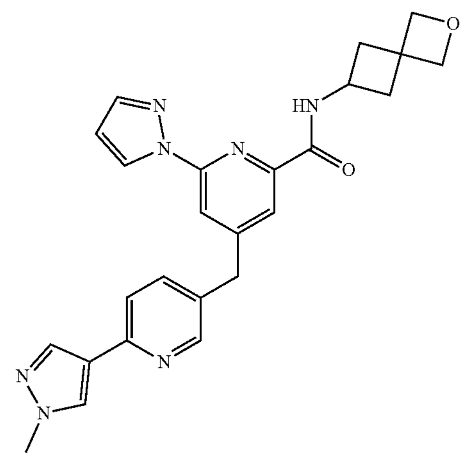 | 456 |
| 22 | N-((1S,2S)-2-hydroxycyclohexyl)-4-(4-(2-methyloxazol-4-yl)benzyl)-6-(1H-pyrazol-1-yl)picolinamide | 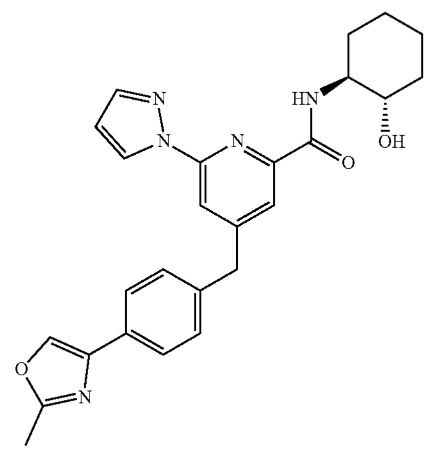 [SMILES: Cc1nc(-c2ccc(Cc3cc(C(=O)N[C@H]4CCCC[C@@H]4O)nc(-n4cccn4)c3)cc2)co1] | 458.2 |
| 23 | 4-(4-(2-methyloxazol-4-yl)benzyl)-6-(1H-pyrazol-1-yl)-N-(2-oxaspiro[3.3]heptan-6-yl)picolinamide | 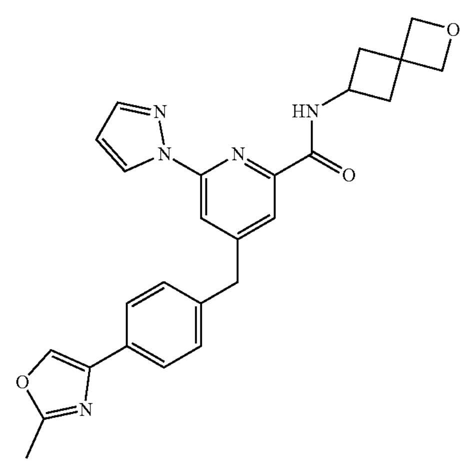 [SMILES: Cc1nc(-c2ccc(Cc3cc(C(=O)NC4CC5(COC5)C4)nc(-n4cccn4)c3)cc2)co1] | 456 |

TABLE 1-continued

| Cpd. No. | Name | Structure | ES-MS [M + 1]+ |
|---|---|---|---|
| 24 | N-((1S,2S)-2-hydroxycyclopentyl)-4-(4-(2-methyloxazol-4-yl)benzyl)-6-(1H-pyrazol-1-yl)picolinamide | 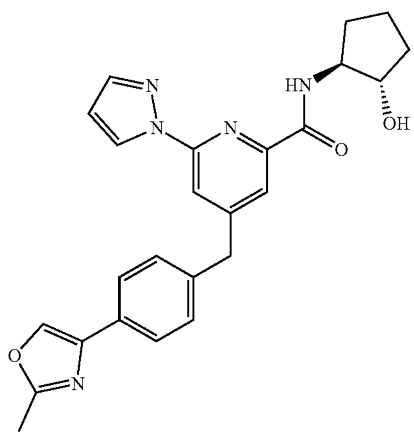 [SMILES: Cc1nc(-c2ccc(Cc3cc(C(=O)N[C@H]4CCC[C@@H]4O)nc(-n4cccn4)c3)cc2)co1] | 444 |
| 25 | N-((1S,2S)-2-hydroxycyclobutyl)-4-(4-(2-methyloxazol-4-yl)benzyl)-6-(1H-pyrazol-1-yl)picolinamide | 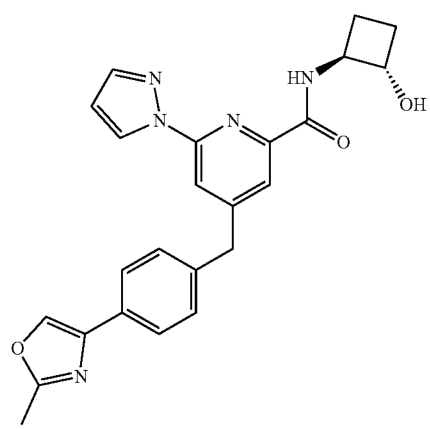 [SMILES: Cc1nc(-c2ccc(Cc3cc(C(=O)N[C@H]4CC[C@@H]4O)nc(-n4cccn4)c3)cc2)co1] | 430 |
| 26 | 4-((6-(1-methyl-1H-pyrazol-4-yl)pyridin-3-yl)methyl)-6-(1H-pyrazol-1-yl)-N-(tetrahydro-2H-pyran-4-yl)picolinamide | 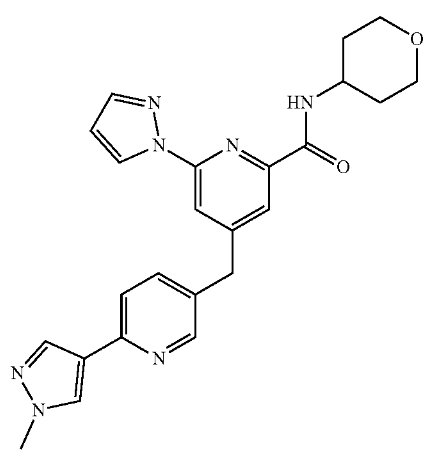 [SMILES: Cn1cc(-c2ccc(Cc3cc(C(=O)NC4CCOCC4)nc(-n4cccn4)c3)cn2)cn1] | 444 |

TABLE 1-continued

| Cpd. No. | Name | Structure | ES-MS [M + 1]+ |
|---|---|---|---|
| 27 | 4-(4-(2-methyloxazol-4-yl)benzyl)-6-(1H-pyrazol-1-yl)-N-(tetrahydro-2H-pyran-4-yl)picolinamide | 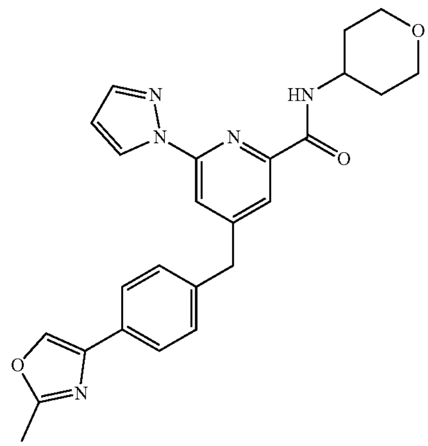 [SMILES: Cc1nc(-c2ccc(Cc3cc(C(=O)NC4CCOCC4)nc(-n4cccn4)c3)cc2)co1] | 444 |
| 28 | N-((3R,4S)-3-hydroxytetrahydro-2H-pyran-4-yl)-4-(4-(1-methyl-1H-pyrazol-3-yl)benzyl)-6-(1H-pyrazol-1-yl)picolinamide | 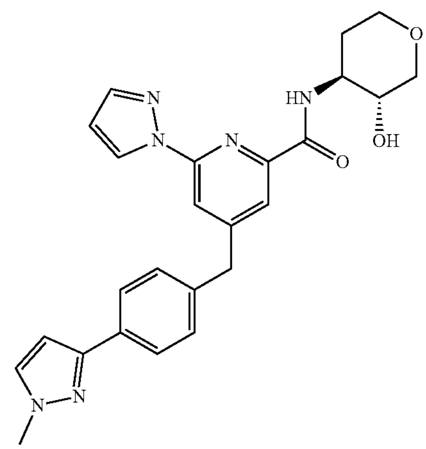 [SMILES: Cn1ccc(-c2ccc(Cc3cc(C(=O)N[C@H]4CCOC[C@@H]4O)nc(-n4cccn4)c3)cc2)n1] | 459.4 |
| 29 | N-((1S,2S)-2-hydroxycyclohexyl)-4-(4-(1-methyl-1H-pyrazol-3-yl)benzyl)-6-(1H-pyrazol-1-yl)picolinamide | 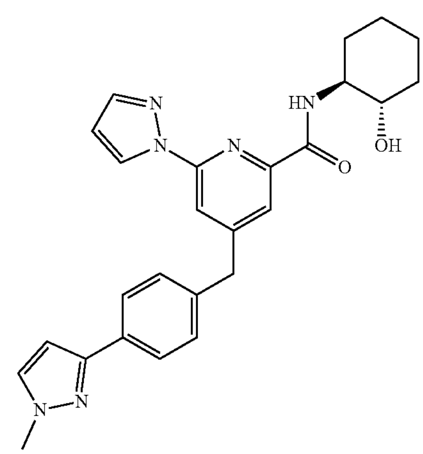 [SMILES: Cn1ccc(-c2ccc(Cc3cc(C(=O)N[C@H]4CCCC[C@@H]4O)nc(-n4cccn4)c3)cc2)n1] | 457.4 |

TABLE 1-continued

| Cpd. No. | Name | Structure | ES-MS [M + 1]+ |
|---|---|---|---|
| 30 | 4-(4-(1-methyl-1H-pyrazol-3-yl)benzyl)-6-(1H-pyrazol-1-yl)-N-(tetrahydro-2H-pyran-4-yl)picolinamide | 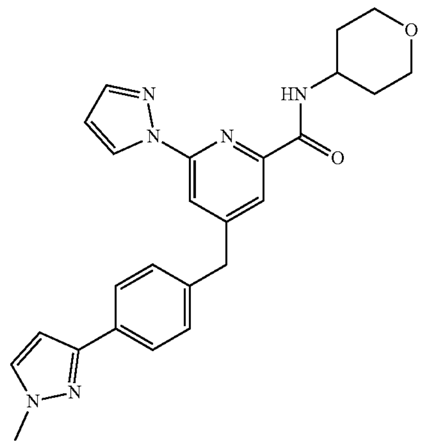 [SMILES: Cn1ccc(-c2ccc(Cc3cc(C(=O)NC4CCOCC4)nc(-n4cccn4)c3)cc2)n1] | 443.4 |
| 31 | 4-(4-(1-methyl-1H-pyrazol-3-yl)benzyl)-6-(1H-pyrazol-1-yl)-N-(2-oxaspiro[3.3]heptan-6-yl)picolinamide | 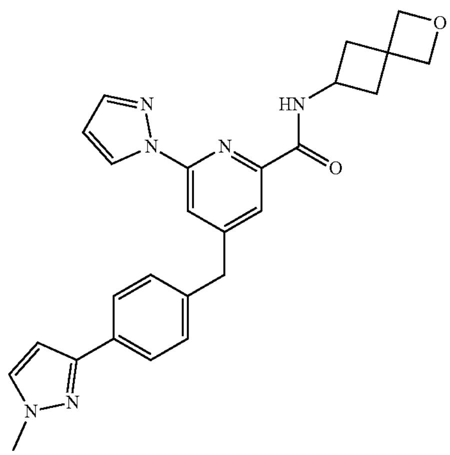 [SMILES: Cn1ccc(-c2ccc(Cc3cc(C(=O)NC4CC5(COC5)C4)nc(-n4cccn4)c3)cc2)n1] | 455.4 |
| 32 | N-((1S,2S)-2-hydroxycyclobutyl)-4-(4-(1-methyl-1H-pyrazol-3-yl)benzyl)-6-(1H-pyrazol-1-yl)picolinamide | 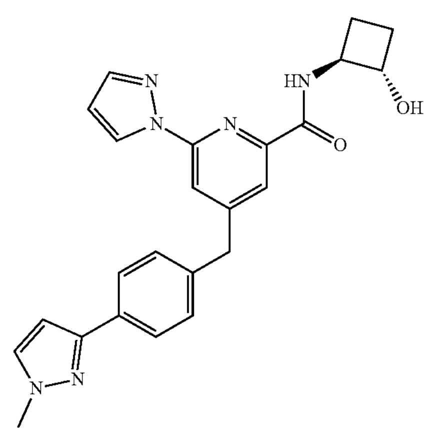 [SMILES: Cn1ccc(-c2ccc(Cc3cc(C(=O)N[C@H]4CC[C@@H]4O)nc(-n4cccn4)c3)cc2)n1] | 429.2 |

TABLE 1-continued

| Cpd. No. | Name | Structure | ES-MS [M + 1]+ |
|---|---|---|---|
| 33 | N-((1S,2S)-2-hydroxycyclopentyl)-4-(4-(1-methyl-1H-pyrazol-3-yl)benzyl)-6-(1H-pyrazol-1-yl)picolinamide | 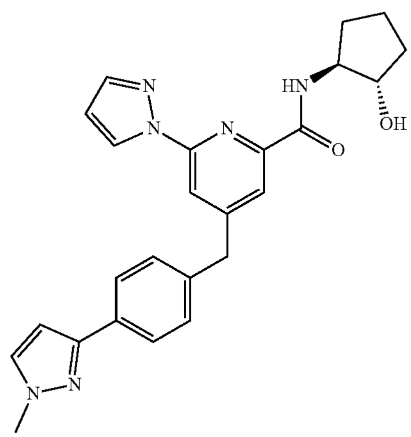 [SMILES: Cn1ccc(-c2ccc(Cc3cc(C(=O)N[C@H]4CCC[C@@H]4O)nc(-n4cccn4)c3)cc2)n1] | 443.4 |
| 34 | N-((1S,2S)-2-hydroxycyclohexyl)-6-(1-methyl-1H-pyrazol-3-yl)-4-(4-(1-methyl-1H-pyrazol-3-yl)benzyl)picolinamide | 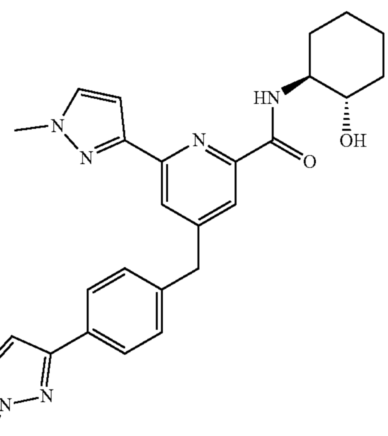 | 474.4 |
| 35 | 6-(1-methyl-1H-pyrazol-3-yl)-4-(4-(1-methyl-1H-pyrazol-3-yl)benzyl)-N-(tetrahydro-2H-pyran-4-yl)picolinamide | 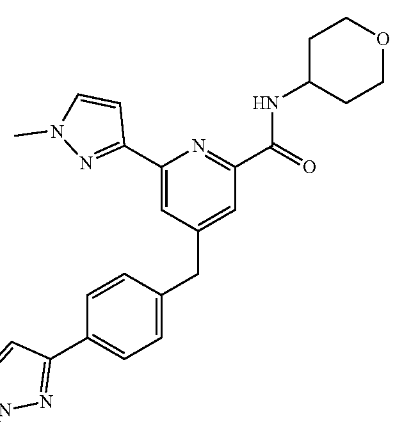 | 457.4 |

TABLE 1-continued

| Cpd. No. | Name | Structure | ES-MS [M + 1]+ |
|---|---|---|---|
| 36 | 6-(1-methyl-1H-pyrazol-3-yl)-4-(4-(1-methyl-1H-pyrazol-3-yl)benzyl)-N-(2-oxaspiro[3.3]heptan-6-yl)picolinamide | 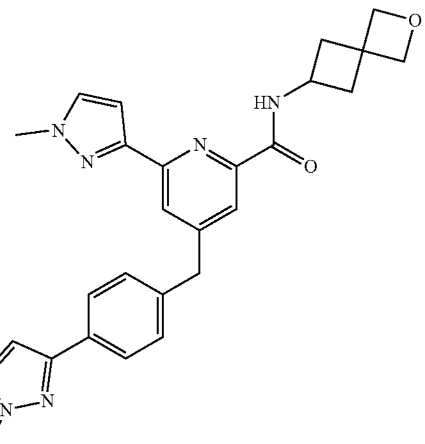 | 469.4 |
| 37 | N-((3R,4S)-3-hydroxytetrahydro-2H-pyran-4-yl)-6-(1-methyl-1H-pyrazol-3-yl)-4-(4-(1-methyl-1H-pyrazol-3-yl)benzyl)picolinamide | 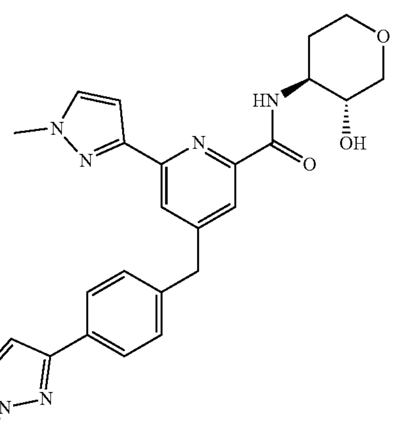 | 473.5 |
| 38 | N-((1S,2S)-2-hydroxycyclopentyl)-6-(1-methyl-1H-pyrazol-3-yl)-4-(4-(1-methyl-1H-pyrazol-3-yl)benzyl)picolinamide | 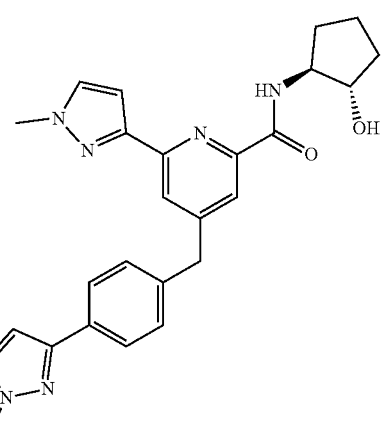 | 457.4 |

TABLE 1-continued

| Cpd. No. | Name | Structure | ES-MS [M + 1]+ |
|---|---|---|---|
| 39 | N-((3R,4S)-3-hydroxytetrahydro-2H-pyran-4-yl)-4-(4-(1-methyl-1H-pyrazol-3-yl)benzyl)-6-(1-methyl-1H-pyrazol-4-yl)picolinamide | 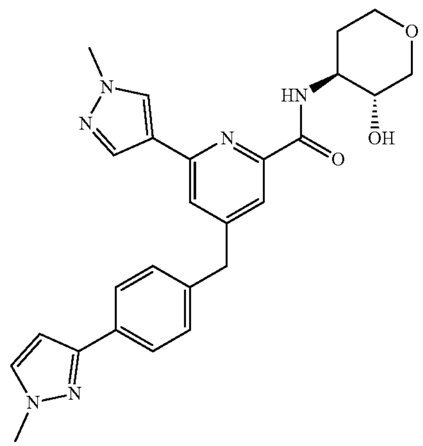 [SMILES: Cn1cc(-c2cc(Cc3ccc(-c4ccn(C)n4)cc3)cc(C(=O)N[C@H]3CCOC[C@@H]3O)n2)cn1] | 473.4 |
| 40 | N-((1S,2S)-2-hydroxycyclohexyl)-4-(4-(1-methyl-1H-pyrazol-3-yl)benzyl)-6-(1-methyl-1H-pyrazol-4-yl)picolinamide | 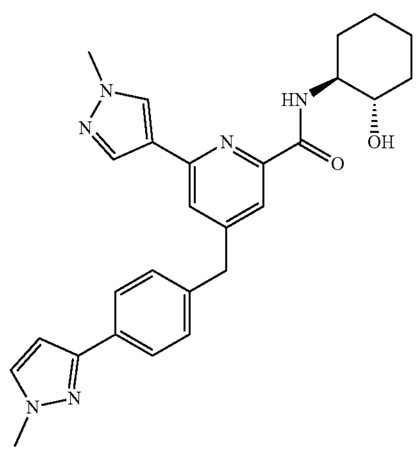 [SMILES: Cn1cc(-c2cc(Cc3ccc(-c4ccn(C)n4)cc3)cc(C(=O)N[C@H]3CCCC[C@@H]3O)n2)cn1] | 471.3 |
| 41 | N-((1S,2S)-2-hydroxycyclohexyl)-5-methyl-4-(4-(1-methyl-1H-pyrazol-3-yl)benzyl)-6-(1H-pyrazol-1-yl)picolinamide | 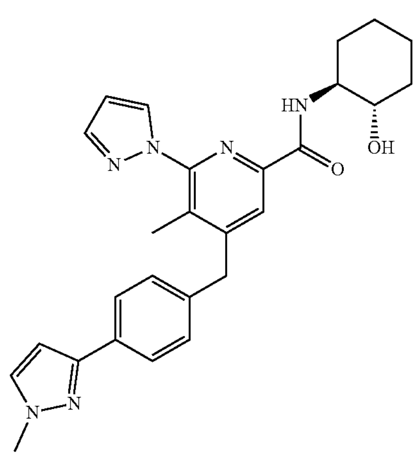 [SMILES: Cc1c(Cc2ccc(-c3ccn(C)n3)cc2)cc(C(=O)N[C@H]2CCCC[C@@H]2O)nc1-n1cccn1] | 471.2 |

TABLE 1-continued

| Cpd. No. | Name | Structure | ES-MS [M + 1]+ |
|---|---|---|---|
| 42 | 5-methyl-4-(4-(1-methyl-1H-pyrazol-3-yl)benzyl)-6-(1H-pyrazol-1-yl)-N-(tetrahydro-2H-pyran-4-yl)picolinamide | 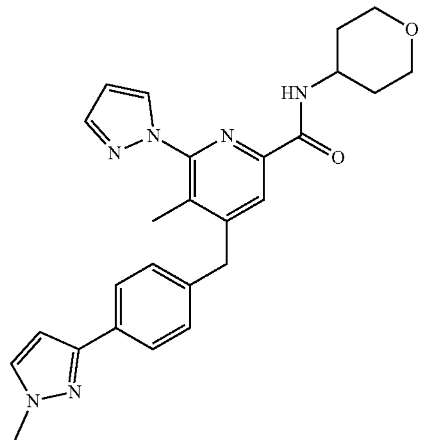 [SMILES: Cc1c(Cc2ccc(-c3ccn(C)n3)cc2)cc(C(=O)NC2CCOCC2)nc1-n1cccn1] | 457.4 |
| 43 | N-((1S,2S)-2-hydroxycyclopentyl)-5-methyl-4-(4-(1-methyl-1H-pyrazol-3-yl)benzyl)-6-(1H-pyrazol-1-yl)picolinamide | 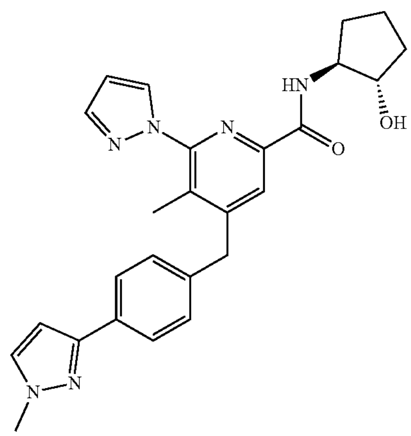 [SMILES: Cc1c(Cc2ccc(-c3ccn(C)n3)cc2)cc(C(=O)N[C@H]2CCC[C@@H]2O)nc1-n1cccn1] | 457.2 |
| 44 | N-((3R,4S)-3-hydroxytetrahydro-2H-pyran-4-yl)-5-methyl-4-((6-(1-methyl-1H-pyrazol-3-yl)pyridin-3-yl)methyl)-6-(1H-pyrazol-1-yl)picolinamide | 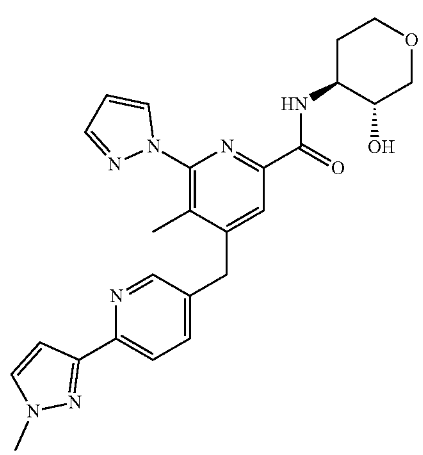 [SMILES: Cc1c(Cc2ccc(-c3ccn(C)n3)nc2)cc(C(=O)N[C@H]2CCOC[C@@H]2O)nc1-n1cccn1] | 474.4 |

TABLE 1-continued

| Cpd. No. | Name | Structure | ES-MS [M + 1]+ |
|---|---|---|---|
| 45 | N-((3R,4S)-3-hydroxytetrahydro-2H-pyran-4-yl)-5-methyl-4-(4-(2-methyloxazol-4-yl)benzyl)-6-(1H-pyrazol-1-yl)picolinamide | 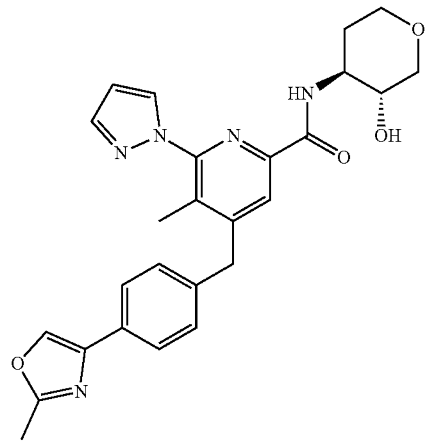 [SMILES: Cc1nc(-c2ccc(Cc3cc(C(=O)N[C@H]4CCOC[C@@H]4O)nc(-n4cccn4)c3C)cc2)co1] | 474 |
| 46 | N-((1S,2S)-2-hydroxycyclohexyl)-5-methyl-4-((6-(1-methyl-1H-pyrazol-3-yl)pyridin-3-yl)methyl)-6-(1H-pyrazol-1-yl)picolinamide | 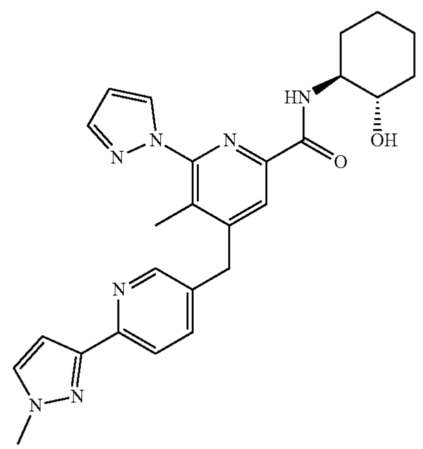 [SMILES: Cc1c(Cc2ccc(-c3ccn(C)n3)nc2)cc(C(=O)N[C@H]2CCCC[C@@H]2O)nc1-n1cccn1] | 472.2 |
| 47 | N-((1S,2S)-2-hydroxycyclohexyl)-5-methyl-4-((6-(1-methyl-1H-pyrazol-4-yl)pyridin-3-yl)methyl)-6-(1H-pyrazol-1-yl)picolinamide | 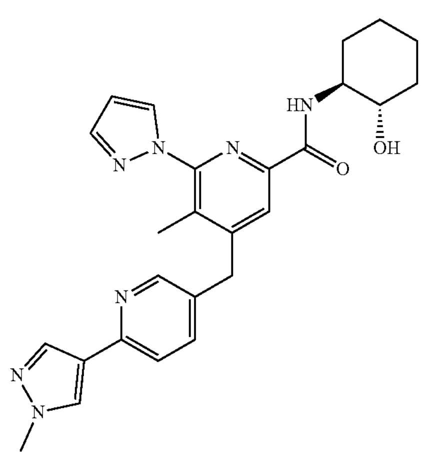 | 472.2 |

TABLE 1-continued

| Cpd. No. | Name | Structure | ES-MS [M + 1]+ |
|---|---|---|---|
| 48 | N-((1S,2S)-2-hydroxycyclohexyl)-5-methyl-4-(4-(2-methyloxazol-4-yl)benzyl)-6-(1H-pyrazol-1-yl)picolinamide | 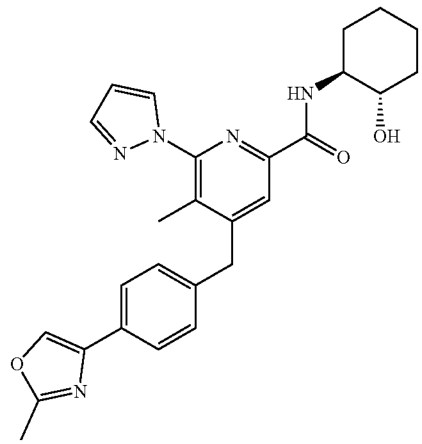 [SMILES: Cc1nc(-c2ccc(Cc3cc(C(=O)N[C@H]4CCCC[C@@H]4O)nc(-n4cccn4)c3C)cc2)co1] | 472.2 |
| 49 | 5-methyl-4-((6-(1-methyl-1H-pyrazol-3-yl)pyridin-3-yl)methyl)-6-(1H-pyrazol-1-yl)-N-(tetrahydro-2H-pyran-4-yl)picolinamide | 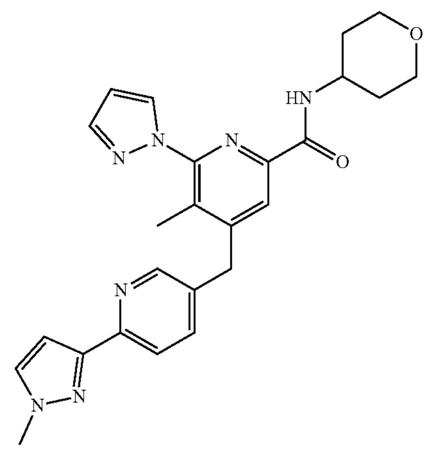 [SMILES: Cc1c(Cc2ccc(-c3ccn(C)n3)nc2)cc(C(=O)NC2CCOCC2)nc1-n1cccn1] | 458.2 |
| 50 | 5-methyl-4-((6-(1-methyl-1H-pyrazol-4-yl)pyridin-3-yl)methyl)-6-(1H-pyrazol-1-yl)-N-(tetrahydro-2H-pyran-4-yl)picolinamide | 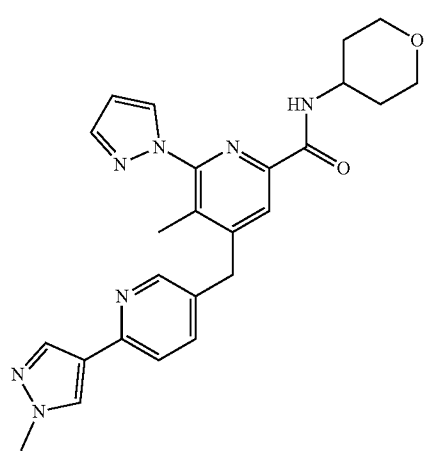 | 458.2 |

TABLE 1-continued
| Cpd. No. | Name | Structure | ES-MS [M + 1]+ |
|---|---|---|---|
| 51 | 5-methyl-4-(4-(2-methyloxazol-4-yl)benzyl)-6-(1H-pyrazol-1-yl)-N-(tetrahydro-2H-pyran-4-yl)picolinamide | 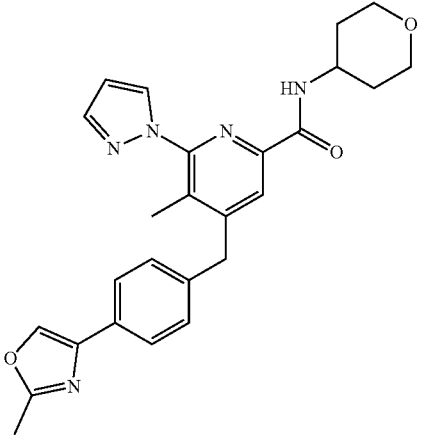 [SMILES: Cc1nc(-c2ccc(Cc3cc(C(=O)NC4CCOCC4)nc(-n4cccn4)c3C)cc2)co1] | 458.2 |
| 52 | N-((1S,2S)-2-hydroxycyclopentyl)-5-methyl-4-((6-(1-methyl-1H-pyrazol-3-yl)pyridin-3-yl)methyl)-6-(1H-pyrazol-1-yl)picolinamide | 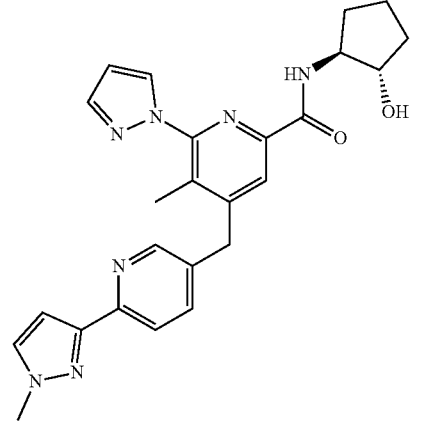 [SMILES: Cc1c(Cc2ccc(-c3ccn(C)n3)nc2)cc(C(=O)N[C@H]2CCC[C@@H]2O)nc1-n1cccn1] | 458.2 |
| 53 | N-((1S,2S)-2-hydroxycyclopentyl)-5-methyl-4-((6-(1-methyl-1H-pyrazol-4-yl)pyridin-3-yl)methyl)-6-(1H-pyrazol-1-yl)picolinamide | 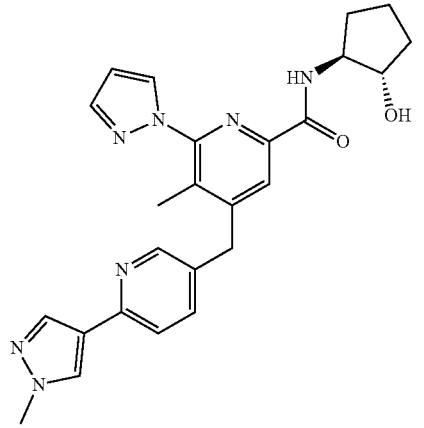 | 458 |

TABLE 1-continued

| Cpd. No. | Name | Structure | ES-MS [M + 1]+ |
|---|---|---|---|
| 54 | N-((1S,2S)-2-hydroxycyclopentyl)-5-methyl-4-(4-(2-methyloxazol-4-yl)benzyl)-6-(1H-pyrazol-1-yl)picolinamide | 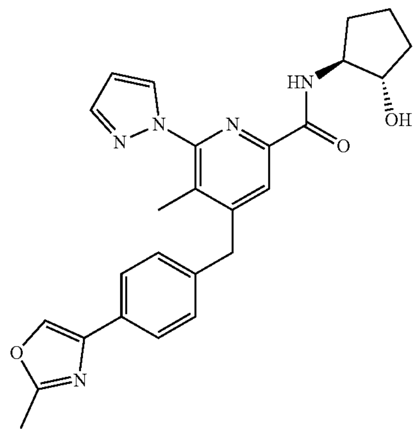 [SMILES: Cc1nc(-c2ccc(Cc3cc(C(=O)N[C@H]4CCC[C@@H]4O)nc(-n4cccn4)c3C)cc2)co1] | 458.2 |
| 55 | 4-(4-(1H-pyrazol-1-yl)benzyl)-N-((3R,4S)-3-hydroxytetrahydro-2H-pyran-4-yl)-5-methyl-6-(1-methyl-1H-pyrazol-3-yl)picolinamide | 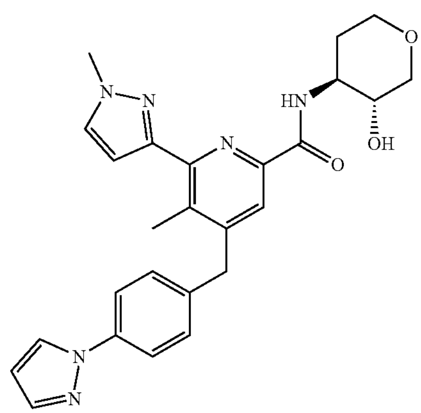 [SMILES: Cc1c(Cc2ccc(-n3cccn3)cc2)cc(C(=O)N[C@H]2CCOC[C@@H]2O)nc1-c1ccn(C)n1] | 473.4 |
| 56 | 4-(4-(1H-pyrazol-1-yl)benzyl)-N-((1S,2S)-2-hydroxycyclohexyl)-5-methyl-6-(1-methyl-1H-pyrazol-3-yl)picolinamide | 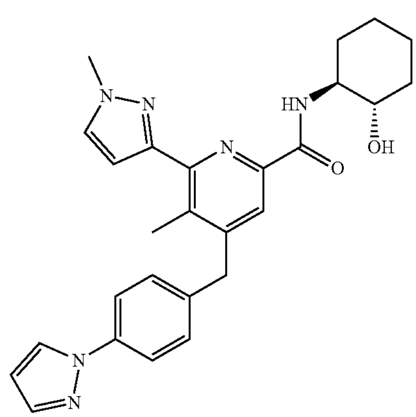 [SMILES: Cc1c(Cc2ccc(-n3cccn3)cc2)cc(C(=O)N[C@H]2CCCC[C@@H]2O)nc1-c1ccn(C)n1] | 471.4 |

TABLE 1-continued

| Cpd. No. | Name | Structure | ES-MS [M + 1]+ |
|---|---|---|---|
| 57 | 4-(4-(1H-pyrazol-1-yl)benzyl)-5-methyl-6-(1-methyl-1H-pyrazol-3-yl)-N-(tetrahydro-2H-pyran-4-yl)picolinamide | 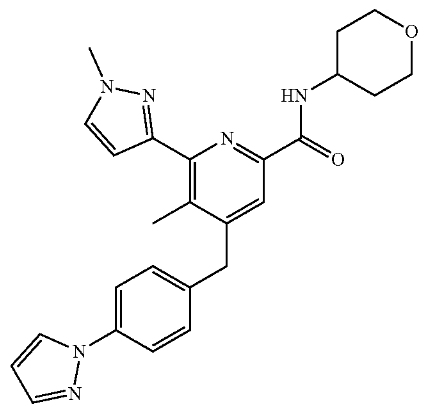 [SMILES: Cc1c(Cc2ccc(-n3cccn3)cc2)cc(C(=O)NC2CCOCC2)nc1-c1ccn(C)n1] | 457.4 |
| 58 | 4-(4-(1H-pyrazol-1-yl)benzyl)-5-methyl-6-(1-methyl-1H-pyrazol-3-yl)-N-(2-oxaspiro[3.3]heptan-6-yl)picolinamide | 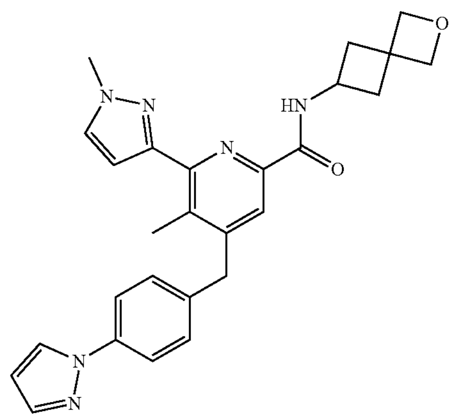 [SMILES: Cc1c(Cc2ccc(-n3cccn3)cc2)cc(C(=O)NC2CC3(COC3)C2)nc1-c1ccn(C)n1] | 469.4 |
| 59 | 4-(4-(1H-pyrazol-1-yl)benzyl)-N-((1S,2S)-2-hydroxycyclopentyl)-5-methyl-6-(1-methyl-1H-pyrazol-3-yl)picolinamide | 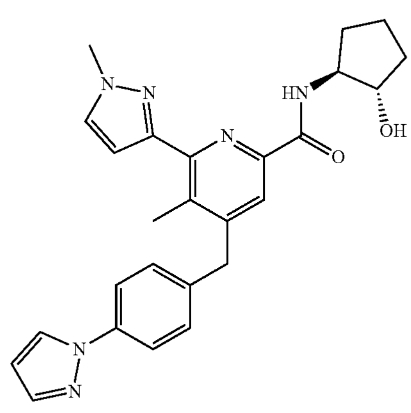 [SMILES: Cc1c(Cc2ccc(-n3cccn3)cc2)cc(C(=O)N[C@H]2CCC[C@@H]2O)nc1-c1ccn(C)n1] | 457.4 |

TABLE 1-continued

| Cpd. No. | Name | Structure | ES-MS [M + 1]+ |
|---|---|---|---|
| 60 | 4-(4-(1H-pyrazol-1-yl)benzyl)-N-((1S,2S)-2-hydroxycyclobutyl)-5-methyl-6-(1-methyl-1H-pyrazol-3-yl)picolinamide | 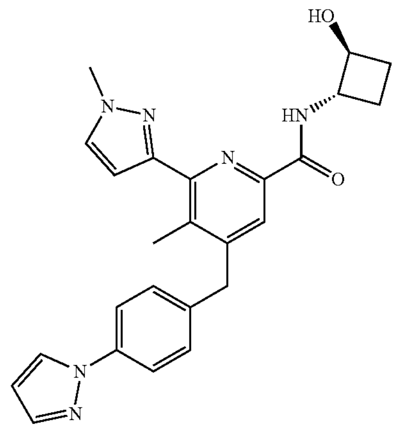 [SMILES: Cc1c(Cc2ccc(-n3cccn3)cc2)cc(C(=O)N[C@H]2CC[C@@H]2O)nc1-c1ccn(C)n1] | 443.4 |
| 61 | 4-(4-(1H-pyrazol-1-yl)benzyl)-5-methyl-6-(1-methyl-1H-pyrazol-3-yl)-N-((tetrahydro-2H-pyran-4-yl)methyl)picolinamide | 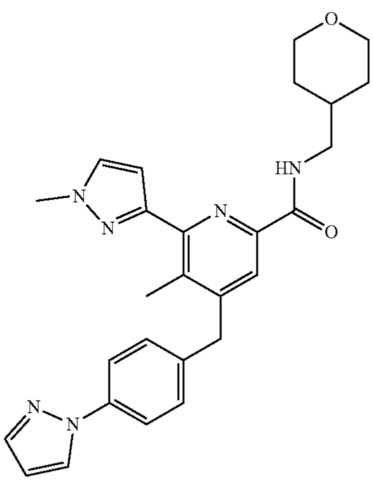 [SMILES: Cc1c(Cc2ccc(-n3cccn3)cc2)cc(C(=O)NCC2CCOCC2)nc1-c1ccn(C)n1] | 471.4 |
| 62 | (S)-4-(4-(1H-pyrazol-1-yl)benzyl)-5-methyl-6-(1-methyl-1H-pyrazol-3-yl)-N-((tetrahydrofuran-2-yl)methyl)picolinamide | 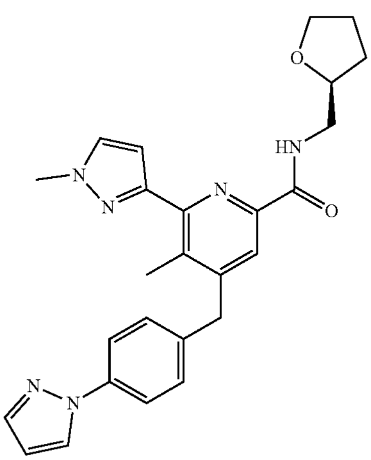 [SMILES: Cc1c(Cc2ccc(-n3cccn3)cc2)cc(C(=O)NC[C@@H]2CCCO2)nc1-c1ccn(C)n1] | 457.4 |

TABLE 1-continued

| Cpd. No. | Name | Structure | ES-MS [M + 1]+ |
|---|---|---|---|
| 63 | (R)-4-(4-(1H-pyrazol-1-yl)benzyl)-5-methyl-6-(1-methyl-1H-pyrazol-3-yl)-N-((tetrahydrofuran-2-yl)methyl)picolinamide | 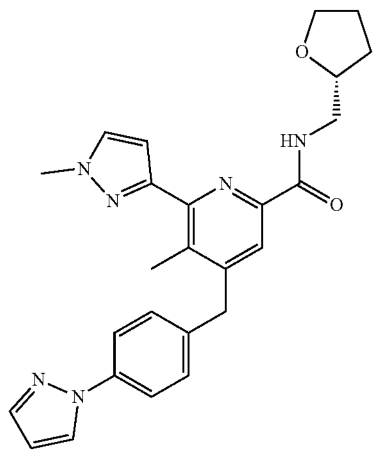 [SMILES: Cc1c(Cc2ccc(-n3cccn3)cc2)cc(C(=O)NC[C@H]2CCCO2)nc1-c1ccn(C)n1] | 457.4 |
| 64 | 4-(4-(1H-pyrazol-1-yl)benzyl)-N-(3,3-dimethyltetrahydro-2H-pyran-4-yl)-5-methyl-6-(1-methyl-1H-pyrazol-3-yl)picolinamide | 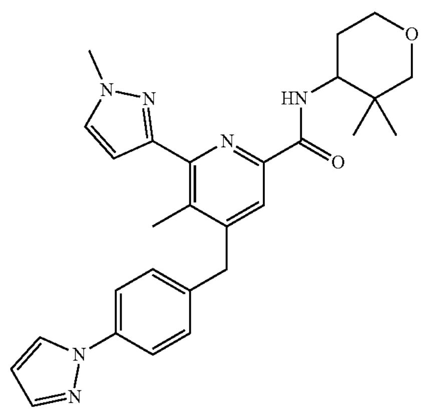 [SMILES: Cc1c(Cc2ccc(-n3cccn3)cc2)cc(C(=O)NC2CCOCC2(C)C)nc1-c1ccn(C)n1] | 485.4 |
| 65 | N-((3R,4S)-3-hydroxytetrahydro-2H-pyran-4-yl)-5-methyl-6-(1-methyl-1H-pyrazol-3-yl)-4-((6-methylpyridin-3-yl)methyl)picolinamide | 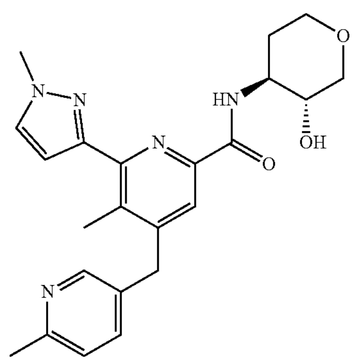 [SMILES: Cc1ccc(Cc2cc(C(=O)N[C@H]3CCOC[C@@H]3O)nc(-c3ccn(C)n3)c2C)cn1] | 422.4 |
| 66 | N-((1S,2S)-2-hydroxycyclohexyl)-5-methyl-6-(1-methyl-1H-pyrazol-3-yl)-4-((6-methylpyridin-3-yl)methyl)picolinamide | 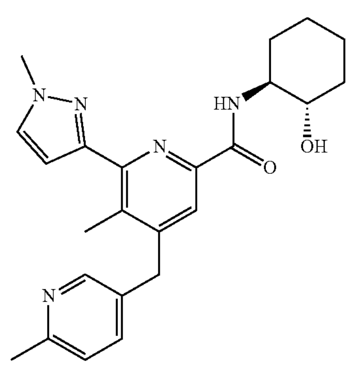 [SMILES: Cc1ccc(Cc2cc(C(=O)N[C@H]3CCCC[C@@H]3O)nc(-c3ccn(C)n3)c2C)cn1] | 420.4 |

TABLE 1-continued

| Cpd. No. | Name | Structure | ES-MS [M + 1]+ |
|---|---|---|---|
| 67 | N-((1S,2S)-2-hydroxycyclopentyl)-5-methyl-6-(1-methyl-1H-pyrazol-3-yl)-4-((6-methylpyridin-3-yl)methyl)picolinamide | 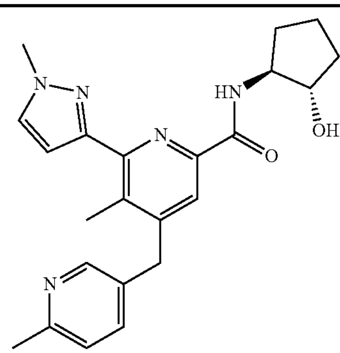 | 406.4 |

Example 4. Biological Activity a. Cell Lines Expressing Muscarinic Acetylcholine Receptors Chinese hamster ovary (CHO-K1) cells stably expressing rat (r)$M_1$ were purchased from the American Type Culture Collection and cultured according to their indicated protocol. CHO cells stably expressing human (h)$M_2$, h$M_3$, and h$M_5$ were described previously (Levey, et al., 1991); h$M_1$ and h$M_4$ cDNAs were purchased from Missouri S&T cDNA Resource; r$M_4$ cDNA was provided by T. I. Bonner (National Institutes of Health, Bethesda, Md.). r$M_2$ and r$M_3$ were cloned from a rat brain cDNA library and sequence verified. h$M_1$, r$M_2$, r$M_3$, h$M_4$, and r$M_4$ cDNAs were used to stably transfect CHO-K1 cells purchased from the American Type Culture Collection using Lipofectamine2000. To make stable r$M_2$, h$M_2$, r$M_3$, h$M_4$, and r$M_4$ cell lines for use in calcium mobilization assays, these cells also were stably transfected with a chimeric G-protein ($G_{qi5}$) (provided by B. R. Conklin, University of California, San Francisco) using Lipofectamine 2000. r$M_1$, h$M_1$, r$M_3$, h$M_3$, r$M_5$, and h$M_5$ cells were grown in Ham's F-12 medium containing 10% heat-inactivated fetal bovine serum (FBS), 20 mM HEPES, and 50 µg/mL G418 sulfate. r$M_2$-$G_{qi5}$, h$M_2$-$G_{qi5}$, and h$M_4$-$G_{qi5}$ cells were grown in the same medium also containing 500 µg/mL Hygromycin B. Stable r$M_4$-$G_{qi5}$ cells were grown in DMEM containing 10% heat-inactivated FBS, 20 mM HEPES, 400 µg/mL G418 sulfate, and 500 µg/mL Hygromycin B.

b. Cell-Based Functional Assay of Muscarinic Acetylcholine Receptor Activity

For high throughput measurement of agonist-evoked increases in intracellular calcium, CHO-K1 cells stably expressing muscarinic receptors were plated in growth medium lacking G418 and hygromycin at 15,000 cells/20 µL/well in Greiner 384-well black-walled, tissue culture (TC)-treated, clear-bottom plates (VWR). Cells were incubated overnight at 37° C. and 5% $CO_2$. The next day, cells were washed using an ELX 405 (BioTek) with four washes (80 µL) of assay buffer then aspirated to 20 µL. Next, 20 µL of 16 µM Fluo-4/acetoxymethyl ester (Invitrogen, Carlsbad, Calif.) prepared as a 2.3 mM stock in DMSO and mixed in a 1:1 ratio with 10% (w/v) Pluronic F-127 and diluted in assay buffer was added to the wells and the cell plates were incubated for 50 min at 37° C. and 5% $CO_2$. Dye was removed by washing with the ELX 405 (four 80 µL washes of assay buffer) then aspirated to 20 µL. Compound master plates were formatted in an 11 point CRC format (1:3 dilutions) in 100% DMSO with a starting concentration of 10 mM using the BRAVO liquid handler (Agilent). Test compound CRCs were then transferred to daughter plates (240 nL) using the Echo acoustic plate reformatter (Labcyte, Sunnyvale, Calif.) and then diluted into assay buffer (40 µL) to a 2× stock using a Thermo Fisher Combi (Thermo Fisher Scientific, Waltham, Mass.).

Calcium flux was measured using the Functional Drug Screening System (FDSS) 6000 (Hamamatsu Corporation, Tokyo, Japan) as an increase in the fluorescent static ratio. Compounds were applied to cells (20 µL, 2×) using the automated system of the FDSS 6000 at 4 s into the 300 s protocol and the data were collected at 1 Hz. At 144 s into the 300 s protocol, 10 µL of an $EC_{20}$ concentration of the muscarinic receptor agonist acetylcholine was added (5×), followed by the addition of 12 µL an $EC_{80}$ concentration of acetylcholine at the 230 s time point (5×). Agonist activity was analyzed as a concentration-dependent increase in calcium mobilization upon compound addition. $E_{max}$ values for agonist activity are expressed relative to the maximum for acetylcholine. Positive allosteric modulator activity was analyzed as a concentration-dependent increase in the $EC_{20}$ acetylcholine response. Antagonist activity was analyzed as a concentration-dependent decrease in the $EC_{80}$ acetylcholine response. Concentration-response curves were generated using a four-parameter logistical equation in XLfit curve fitting software (IDBS, Bridgewater, N.J.) for Excel (Microsoft, Redmond, Wash.) or Prism (GraphPad Software, Inc., San Diego, Calif.).

The above described assay was also operated in a second mode where an appropriate fixed concentration of the present compounds were added to the cells after establishment of a fluorescence baseline for about 3 seconds, and the response in cells was measured. 140 s later the appropriate concentration of agonist was added and readings taken for an additional 106 s. Data were reduced as described above and the $EC_{50}$ values for the agonist in the presence of test compound were determined by nonlinear curve fitting. A decrease in the $EC_{50}$ value of the agonist with increasing concentrations of the present compounds (a leftward shift of the agonist concentration-response curve) is an indication of the degree of muscarinic positive allosteric modulation at a given concentration of the present compound. An increase in the $EC_{50}$ value of the agonist with increasing concentrations of the present compounds (a rightward shift of the agonist concentration response curve) is an indication of the degree of muscarinic antagonism at a given concentration of the present compound. The second mode also indicates whether the present compounds also affect the maximum response of the muscarinic receptor to agonists.

c. Results and Discussion of Biological Activity Data

Activity ($EC_{50}$ and $E_{max}$) was determined in the mAChR $M_1$ cell-based functional assay as described above and the data are shown in Table 2. The compound numbers correspond to the compound numbers used in Table 1. The data in Table 2 demonstrate that the disclosed compounds are positive allosteric modulators of human mAChR $M_1$ and show high PAM activity for the human mAChR $M_1$ receptor(s).

TABLE 2

Biological Activity Data

| Cpd. No. | PAM Activity | | Agonist Activity | |
|---|---|---|---|---|
| | Human $M_1$ $EC_{50}$ (µM) | $E_{max}$ (%) | Human $M_1$ $EC_{50}$ (µM) | $E_{max}$ (%) |
| 1 | 8.72 | 85 | >10 | <5 |
| 2 | 0.317 | 78 | 7.15 | 25 |
| 3 | 4.00 | 90 | >10 | <5 |
| 4 | 10.0 | 53 | >10 | <5 |
| 5 | 10.0 | 52 | >10 | <5 |
| 6 | 10.0 | 67 | >10 | <5 |
| 7 | 10.0 | 38 | >10 | <5 |
| 8 | 8.01 | 75 | >10 | <5 |
| 9 | 0.542 | 86 | 9.81 | 18 |
| 10 | 0.910 | 86 | 10 | 13 |
| 11 | 4.72 | 88 | >10 | <5 |
| 12 | 1.97 | 86 | >10 | 6 |
| 13 | 7.99 | 80 | >10 | <5 |
| 14 | 10.0 | 74 | >10 | <5 |
| 15 | 4.61 | 82 | >10 | <5 |
| 16 | 10.0 | 62 | >10 | <5 |
| 17 | 2.26 | 86 | >10 | <5 |
| 18 | 1.02 | 85 | 10 | 13 |
| 19 | 1.97 | 88 | >10 | <5 |
| 20 | 2.25 | 61 | >10 | <5 |
| 21 | 10.0 | 40 | >10 | <5 |
| 22 | 0.634 | 86 | 10 | 11 |
| 23 | 6.25 | 69 | >10 | <5 |
| 24 | 4.91 | 78 | >10 | <5 |
| 25 | 10.0 | 40 | >10 | <5 |
| 26 | 10.0 | 47 | >10 | 5 |
| 27 | 10.0 | 62 | >10 | 6 |
| 28 | 1.07 | 78 | >10 | 7 |
| 29 | 2.10 | 73 | >10 | <5 |
| 30 | 10.0 | 65 | >10 | <5 |
| 31 | 10.0 | 56 | >10 | <5 |
| 32 | 10.0 | 46 | >10 | <5 |
| 33 | 5.51 | 69 | >10 | <5 |
| 34 | 2.02 | 63 | >10 | <5 |
| 35 | 10.0 | 46 | >10 | <5 |
| 36 | 3.71 | 38 | >10 | <5 |
| 37 | 1.56 | 76 | >10 | <5 |
| 38 | 2.72 | 39 | >10 | <5 |
| 39 | 2.85 | 57 | >10 | <5 |
| 40 | 9.44 | 57 | >10 | <5 |
| 41 | 0.307 | 79 | 7.78 | 26 |
| 42 | 10.0 | 83 | >10 | <5 |
| 43 | 1.3 | 85 | 10 | 14 |
| 44 | 1.09 | 83 | 10 | 23 |
| 45 | 0.863 | 47 | >10 | 8 |
| 46 | 0.881 | 85 | 10 | 28 |
| 47 | 0.675 | 85 | 9.08 | 29 |
| 48 | 0.832 | 59 | 8.59 | 10 |
| 49 | 10.0 | 63 | >10 | <5 |
| 50 | 10.0 | 65 | >10 | <5 |
| 51 | 10.0 | 69 | >10 | <5 |
| 52 | 5.03 | 84 | >10 | 9 |
| 53 | 3.96 | 75 | >10 | 5 |
| 54 | 3.87 | 52 | >10 | <5 |
| 55 | 0.324 | 77 | 6.70 | 22 |
| 56 | 0.906 | 81 | >10 | <5 |
| 57 | 5.70 | 81 | >10 | <5 |
| 58 | 6.00 | 83 | >10 | <5 |
| 59 | 1.98 | 85 | >10 | <5 |
| 60 | 10.0 | 79 | >10 | <5 |
| 61 | 10.0 | 64 | >10 | <5 |
| 62 | 4.63 | 77 | >10 | <5 |
| 63 | 10.0 | 57 | >10 | <5 |
| 64 | 2.89 | 91 | >10 | <5 |
| 65 | 10.0 | 71 | >10 | <5 |
| 66 | 10.0 | 66 | >10 | <5 |
| 67 | 10.0 | 38 | >10 | <5 |

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

For reasons of completeness, various aspects of the invention are set out in the following numbered clauses:

Clause 1. A compound of formula (I),

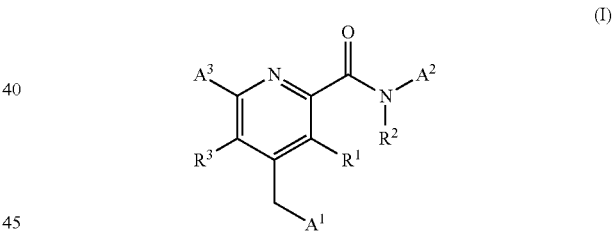

(I)

or a pharmaceutically acceptable salt thereof, wherein
$A^1$ is $Cyc^1$ or -$Cyc^2$-$Cyc^3$;
$Cyc^1$ is a 6- to 12-membered aryl or 5- to 12-membered heteroaryl;
$Cyc^2$ is a 6- to 12-membered aryl, 5- to 12-membered heteroaryl, or 4- to 12-membered heterocycle;
$Cyc^3$ is a 6- to 12-membered aryl or 5- to 12-membered heteroaryl;
wherein $Cyc^1$, $Cyc^2$, and $Cyc^3$ are each independently optionally substituted with 1-5 substituents independently selected from the group consisting of halogen, $C_{1-4}$alkyl, $C_{1-4}$haloalkyl, —$OC_{1-4}$alkyl, —$OC_{1-4}$haloalkyl, OH, oxo, cyano, $C_{3-6}$cycloalkyl, and —$C_{1-3}$alkylene-$C_{3-6}$cycloalkyl, wherein each cycloalkyl is optionally substituted with 1-4 substituents independently selected from halogen and $C_{1-4}$alkyl;
$A^2$ is $C_{1-6}$alkyl, $C_{1-6}$haloalkyl, or -$L^1$-$G^1$, wherein the $C_{1-6}$alkyl and $C_{1-6}$haloalkyl are optionally substituted with 1-2 substituents independently selected from cyano, oxo, OH, —$OC_{1-4}$alkyl, and $C_{3-6}$cycloalkyl;

$L^1$ is a bond, $C_{2-6}$alkenylene, or $C_{1-6}$alkylene, wherein the $C_{2-6}$alkenylene and $C_{1-6}$alkylene are optionally substituted with 1-4 substituents independently selected from the group consisting of halogen, cyano, OH, oxo, and —$OC_{1-4}$alkyl;

$G^1$ is $C_{3-12}$cycloalkyl or 4- to 12-membered heterocycle, wherein G1 is optionally substituted with 1-4 substituents independently selected from the group consisting of $C_{1-4}$alkyl, $C_{1-4}$haloalkyl, OH, —$OC_{1-4}$alkyl, cyano, oxo, and $C_{3-6}$cycloalkyl;

$A^3$ is a 5-membered heteroaryl containing 1-3 heteroatoms independently selected from O, N, and S, the heteroaryl being optionally substituted with 1-4 substituents independently selected from the group consisting of halogen, $C_{1-4}$alkyl, $C_{1-4}$haloalkyl, —$OC_{1-4}$alkyl, —$OC_{1-4}$haloalkyl, cyano, $C_{3-6}$cycloalkyl, and —$C_{1-3}$alkylene-$C_{3-6}$cycloalkyl, wherein each cycloalkyl is optionally substituted with 1-4 substituents independently selected from halogen and $C_{1-4}$alkyl;

$R^1$ and $R^3$ are independently hydrogen, halogen, cyano, $C_{1-4}$alkyl, $C_{1-4}$haloalkyl, —$OC_{1-4}$alkyl, or —$C_{1-3}$alkylene-$OC_{1-4}$alkyl; and $R^2$ is hydrogen, $C_{1-6}$alkyl, or $C_{1-6}$haloalkyl.

Clause 2. The compound of clause 1, or a pharmaceutically acceptable salt thereof, wherein $A^3$ is a 5-membered heteroaryl containing two nitrogen atoms and optionally substituted as defined in claim 1.

Clause 3. The compound of clause 2, or a pharmaceutically acceptable salt thereof, wherein $A^3$ is pyrazolyl optionally substituted as defined in claim 1.

Clause 4. The compound of clause 3, or a pharmaceutically acceptable salt thereof, wherein $A^3$ is pyrazol-1-yl, pyrazol-3-yl, or pyrazol-4-yl, each optionally substituted as defined in claim 1.

Clause 5. The compound of any of clauses 1-4, or a pharmaceutically acceptable salt thereof, wherein $A^3$ is optionally substituted with $C_{1-4}$alkyl.

Clause 6. The compound of clause 1, or a pharmaceutically acceptable salt thereof, wherein $A^3$ is

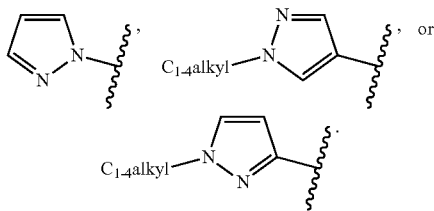

Clause 7. The compound of any of clauses 1-6, or a pharmaceutically acceptable salt thereof, wherein $A^1$ is -$Cyc^2$-$Cyc^3$, wherein $Cyc^2$ and $Cyc^3$ are each independently optionally substituted as defined in claim 1.

Clause 8. The compound of any of clauses 1-7, or a pharmaceutically acceptable salt thereof, wherein $Cyc^2$ is a 6- to 12-membered aryl, wherein $Cyc^2$ is optionally substituted as defined in clause 1.

Clause 9. The compound of clause 8, or a pharmaceutically acceptable salt thereof, wherein $Cyc^2$ is phenyl, wherein $Cyc^2$ is optionally substituted as defined in clause 1.

Clause 10. The compound of any of clauses 1-7, or a pharmaceutically acceptable salt thereof, wherein $Cyc^2$ is a 5- to 12-membered heteroaryl, wherein $Cyc^2$ is optionally substituted as defined in clause 1.

Clause 11. The compound of clause 10, or a pharmaceutically acceptable salt thereof, wherein $Cyc^2$ is pyridinyl, wherein $Cyc^2$ is optionally substituted as defined in clause 1.

Clause 12. The compound of any of clauses 1-7, or a pharmaceutically acceptable salt thereof, wherein $Cyc^2$ is

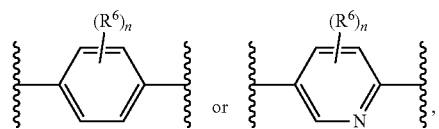

wherein -$Cyc^2$-$Cyc^3$ is

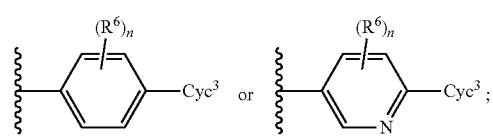

$R^6$, at each occurrence, is independently selected from the group consisting of halogen, $C_{1-4}$alkyl, $C_{1-4}$haloalkyl, —$OC_{1-4}$alkyl, —$OC_{1-4}$haloalkyl, OH, cyano, $C_{3-6}$cycloalkyl, and —$C_{1-3}$alkylene-$C_{3-6}$cycloalkyl; and n is 0, 1, 2, 3, or 4.

Clause 13. The compound of clause 12, or a pharmaceutically acceptable salt thereof, wherein n is 0.

Clause 14. The compound of any of clauses 1-13, or a pharmaceutically acceptable salt thereof, wherein $Cyc^3$ is a 5- to 12-membered heteroaryl, optionally substituted as defined in clause 1.

Clause 15. The compound of any of clauses 1-14, or a pharmaceutically acceptable salt thereof, wherein $Cyc^3$ is a 5- to 6-membered monocyclic heteroaryl, optionally substituted as defined in clause 1.

Clause 16. The compound of any of clauses 1-15, or a pharmaceutically acceptable salt thereof, wherein $Cyc^3$ is a 5-membered monocyclic heteroaryl containing two heteroatoms independently selected from O and N, optionally substituted as defined in clause 1.

Clause 17. The compound of any of clauses 1-16, or a pharmaceutically acceptable salt thereof, wherein $Cyc^3$ is pyrazolyl or oxazolyl and $Cyc^3$ is optionally substituted as defined in clause 1.

Clause 18. The compound of any of clauses 1-17, or a pharmaceutically acceptable salt thereof, wherein $Cyc^3$ is optionally substituted with $C_{1-4}$alkyl.

Clause 19. The compound of any of clauses 1-18, or a pharmaceutically acceptable salt thereof, wherein $Cyc^3$ is

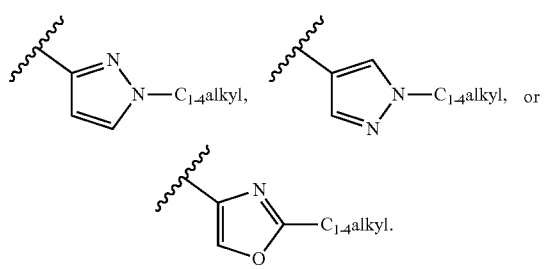

Clause 20. The compound of any of clauses 1-18, or a pharmaceutically acceptable salt thereof, wherein Cyc³ is

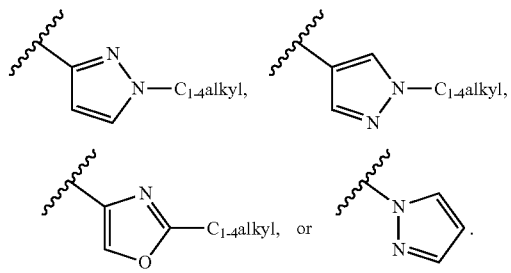

Clause 21. The compound of any of clauses 1-6, or a pharmaceutically acceptable salt thereof, wherein A¹ is Cyc¹.

Clause 22. The compound of clause 21, or a pharmaceutically acceptable salt thereof, wherein Cyc¹ is N

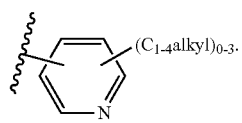

Clause 23. The compound of claim 22, or a pharmaceutically acceptable salt thereof, wherein Cyc¹ is N

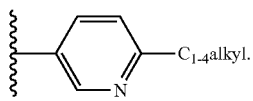

Clause 24. The compound of any of clauses 1-23, or a pharmaceutically acceptable salt thereof, wherein A² is -L¹-G¹ and G¹ is optionally substituted as defined in clause 1.

Clause 25. The compound of any of clauses 1-24, or a pharmaceutically acceptable salt thereof, wherein G¹ is a $C_{3-12}$cycloalkyl or a 4- to 12-membered heterocycle containing one oxygen atom, wherein G¹ is optionally substituted as defined in clause 1.

Clause 26. The compound of any of clauses 1-25, or a pharmaceutically acceptable salt thereof, wherein G¹ is a monocyclic $C_{3-8}$cycloalkyl, a monocyclic 4- to 8-membered heterocycle containing one oxygen atom, or a 7- to 12-membered spirocyclic heterocycle containing one oxygen atom, wherein G¹ is optionally substituted with 1-2 substituents selected from OH and $C_{1-4}$alkyl.

Clause 27. The compound of any of clauses 1-26, or a pharmaceutically acceptable salt thereof, wherein G¹ is

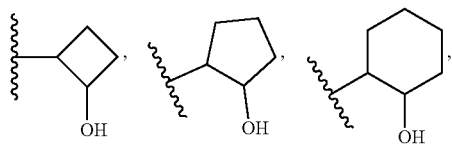

-continued

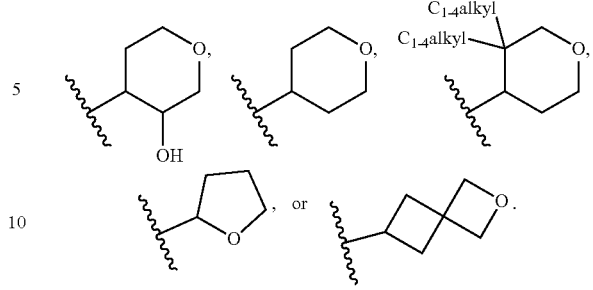

Clause 28. The compound of any of clauses 1-27, or a pharmaceutically acceptable salt thereof, wherein G¹ is

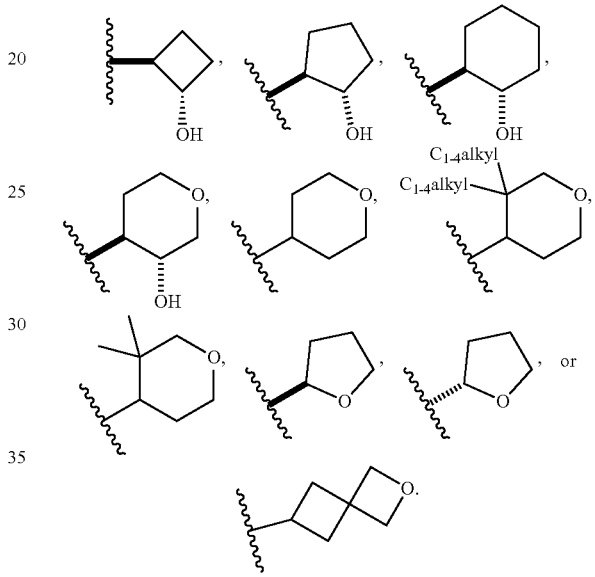

Clause 29. The compound of any of clauses 1-28, or a pharmaceutically acceptable salt thereof, wherein L¹ is a bond.

Clause 30. The compound of any of clause 1-28, or a pharmaceutically acceptable salt thereof, wherein L¹ is $CH_2$.

Clause 31. The compound of any of clauses 1-30, or a pharmaceutically acceptable salt thereof, wherein R¹ is hydrogen.

Clause 32. The compound of any of clauses 1-31, or a pharmaceutically acceptable salt thereof, wherein R² is hydrogen.

Clause 33. The compound of any of clauses 1-32, or a pharmaceutically acceptable salt thereof, wherein R³ is hydrogen or $C_{1-4}$alkyl.

Clause 34. The compound of clause 1, selected from the group consisting of
N-((3R,4S)-3-hydroxytetrahydro-2H-pyran-4-yl)-4-(4-(1-methyl-1H-pyrazol-3-yl)benzyl)-6-(1H-pyrazol-1-yl)picolinamide;
N-((1S,2S)-2-hydroxycyclohexyl)-4-(4-(1-methyl-1H-pyrazol-3-yl)benzyl)-6-(1H-pyrazol-1-yl)picolinamide;
4-(4-(1-methyl-1H-pyrazol-3-yl)benzyl)-6-(1H-pyrazol-1-yl)-N-(tetrahydro-2H-pyran-4-yl)picolinamide;
4-(4-(1-methyl-1H-pyrazol-3-yl)benzyl)-6-(1H-pyrazol-1-yl)-N-(2-oxaspiro[3.3]heptan-6-yl)picolinamide;
N-((1S,2S)-2-hydroxycyclobutyl)-4-(4-(1-methyl-1H-pyrazol-3-yl)benzyl)-6-(1H-pyrazol-1-yl)picolinamide;

N-((1S,2S)-2-hydroxycyclopentyl)-4-(4-(1-methyl-1H-pyrazol-3-yl)benzyl)-6-(1H-pyrazol-1-yl)picolinamide;

N-((1S,2S)-2-hydroxycyclohexyl)-6-(1-methyl-1H-pyrazol-3-yl)-4-(4-(1-methyl-1H-pyrazol-3-yl)benzyl)picolinamide;

6-(1-methyl-1H-pyrazol-3-yl)-4-(4-(1-methyl-H-pyrazol-3-yl)benzyl)-N-(tetrahydro-2H-pyran-4-yl)picolinamide;

6-(1-methyl-1H-pyrazol-3-yl)-4-(4-(1-methyl-H-pyrazol-3-yl)benzyl)-N-(2-oxaspiro[3.3]heptan-6-yl)picolinamide;

N-((3R,4S)-3-hydroxytetrahydro-2H-pyran-4-yl)-6-(1-methyl-1H-pyrazol-3-yl)-4-(4-(1-methyl-1H-pyrazol-3-yl)benzyl)picolinamide;

N-((1S,2S)-2-hydroxycyclopentyl)-6-(1-methyl-1H-pyrazol-3-yl)-4-(4-(1-methyl-1H-pyrazol-3-yl)benzyl)picolinamide;

N-((3R,4S)-3-hydroxytetrahydro-2H-pyran-4-yl)-4-(4-(1-methyl-H-pyrazol-3-yl)benzyl)-6-(1-methyl-1H-pyrazol-4-yl)picolinamide;

N-((1S,2S)-2-hydroxycyclohexyl)-4-(4-(1-methyl-1H-pyrazol-3-yl)benzyl)-6-(1-methyl-1H-pyrazol-4-yl)picolinamide;

N-((1S,2S)-2-hydroxycyclohexyl)-6-(1-methyl-1H-pyrazol-3-yl)-4-((6-(1-methyl-H-pyrazol-4-yl)pyridin-3-yl)methyl)picolinamide;

6-(1-methyl-1H-pyrazol-3-yl)-4-((6-(1-methyl-H-pyrazol-4-yl)pyridin-3-yl)methyl)-N-(tetrahydro-2H-pyran-4-yl)picolinamide;

6-(1-methyl-1H-pyrazol-3-yl)-4-((6-(l-methyl-1H-pyrazol-4-yl)pyridin-3-yl)methyl)-N-(2-oxaspiro[3.3]heptan-6-yl)picolinamide;

N-((1S,2S)-2-hydroxycyclopentyl)-6-(1-methyl-1H-pyrazol-3-yl)-4-((6-(1-methyl-1H-pyrazol-4-yl)pyridin-3-yl)methyl)picolinamide;

(S)-6-(1-methyl-1H-pyrazol-3-yl)-4-((6-(1-methyl-1H-pyrazol-4-yl)pyridin-3-yl)methyl)-N-((tetrahydrofuran-2-yl)methyl)picolinamide;

N-(3,3-dimethyltetrahydro-2H-pyran-4-yl)-6-(1-methyl-1H-pyrazol-3-yl)-4-((6-(1-methyl-1H-pyrazol-4-yl)pyridin-3-yl)methyl)picolinamide;

N-((3R,4S)-3-hydroxytetrahydro-2H-pyran-4-yl)-5-methyl-6-(1-methyl-1H-pyrazol-3-yl)-4-(4-(1-methyl-1H-pyrazol-3-yl)benzyl)picolinamide;

N-((1S,2S)-2-hydroxycyclohexyl)-5-methyl-6-(1-methyl-1H-pyrazol-3-yl)-4-(4-(1-methyl-H-pyrazol-3-yl)benzyl)picolinamide;

5-methyl-6-(1-methyl-1H-pyrazol-3-yl)-4-(4-(1-methyl-1H-pyrazol-3-yl)benzyl)-N-(tetrahydro-2H-pyran-4-yl)picolinamide;

5-methyl-6-(1-methyl-1H-pyrazol-3-yl)-4-(4-(1-methyl-1H-pyrazol-3-yl)benzyl)-N-(2-oxaspiro[3.3]heptan-6-yl)picolinamide;

N-((1S,2S)-2-hydroxycyclopentyl)-5-methyl-6-(1-methyl-1H-pyrazol-3-yl)-4-(4-(1-methyl-H-pyrazol-3-yl)benzyl)picolinamide;

N-((1S,2S)-2-hydroxycyclobutyl)-5-methyl-6-(1-methyl-1H-pyrazol-3-yl)-4-(4-(1-methyl-H-pyrazol-3-yl)benzyl)picolinamide;

5-methyl-6-(1-methyl-1H-pyrazol-3-yl)-4-(4-(1-methyl-1H-pyrazol-3-yl)benzyl)-N-((tetrahydro-2H-pyran-4-yl)methyl)picolinamide;

(S)-5-methyl-6-(1-methyl-1H-pyrazol-3-yl)-4-(4-(1-methyl-1H-pyrazol-3-yl)benzyl)-N-((tetrahydrofuran-2-yl)methyl)picolinamide;

(R)-5-methyl-6-(1-methyl-1H-pyrazol-3-yl)-4-(4-(1-methyl-1H-pyrazol-3-yl)benzyl)-N-((tetrahydrofuran-2-yl)methyl)picolinamide;

N-(3,3-dimethyltetrahydro-2H-pyran-4-yl)-5-methyl-6-(1-methyl-1H-pyrazol-3-yl)-4-(4-(1-methyl-1H-pyrazol-3-yl)benzyl)picolinamide;

N-((3R,4S)-3-hydroxytetrahydro-2H-pyran-4-yl)-4-((6-(1-methyl-1H-pyrazol-4-yl)pyridin-3-yl)methyl)-6-(1H-pyrazol-1-yl)picolinamide;

N-((3R,4S)-3-hydroxytetrahydro-2H-pyran-4-yl)-4-(4-(2-methyloxazol-4-yl)benzyl)-6-(1H-pyrazol-1-yl)picolinamide;

N-((1S,2S)-2-hydroxycyclohexyl)-4-((6-(1-methyl-1H-pyrazol-4-yl)pyridin-3-yl)methyl)-6-(1H-pyrazol-1-yl)picolinamide;

4-((6-(1-methyl-1H-pyrazol-4-yl)pyridin-3-yl)methyl)-6-(1H-pyrazol-1-yl)-N-(2-oxaspiro[3.3]heptan-6-yl)picolinamide;

N-((1S,2S)-2-hydroxycyclohexyl)-4-(4-(2-methyloxazol-4-yl)benzyl)-6-(1H-pyrazol-1-yl)picolinamide;

4-(4-(2-methyloxazol-4-yl)benzyl)-6-(1H-pyrazol-1-yl)-N-(2-oxaspiro[3.3]heptan-6-yl)picolinamide;

N-((1S,2S)-2-hydroxycyclopentyl)-4-(4-(2-methyloxazol-4-yl)benzyl)-6-(1H-pyrazol-1-yl)picolinamide;

N-((1S,2S)-2-hydroxycyclobutyl)-4-(4-(2-methyloxazol-4-yl)benzyl)-6-(1H-pyrazol-1-yl)picolinamide;

4-((6-(1-methyl-1H-pyrazol-4-yl)pyridin-3-yl)methyl)-6-(1H-pyrazol-1-yl)-N-(tetrahydro-2H-pyran-4-yl)picolinamide;

4-(4-(2-methyloxazol-4-yl)benzyl)-6-(1H-pyrazol-1-yl)-N-(tetrahydro-2H-pyran-4-yl)picolinamide; and N-((3R,4S)-3-hydroxytetrahydro-2H-pyran-4-yl)-5-methyl-4-(4-(1-methyl-1H-pyrazol-3-yl)benzyl)-6-(1H-pyrazol-1-yl)picolinamide;

N-((1S,2S)-2-hydroxycyclohexyl)-5-methyl-4-(4-(1-methyl-1H-pyrazol-3-yl)benzyl)-6-(1H-pyrazol-1-yl)picolinamide;

5-methyl-4-(4-(1-methyl-1H-pyrazol-3-yl)benzyl)-6-(1H-pyrazol-1-yl)-N-(tetrahydro-2H-pyran-4-yl)picolinamide;

N-((1S,2S)-2-hydroxycyclopentyl)-5-methyl-4-(4-(1-methyl-1H-pyrazol-3-yl)benzyl)-6-(1H-pyrazol-1-yl)picolinamide;

N-((3R,4S)-3-hydroxytetrahydro-2H-pyran-4-yl)-5-methyl-4-((6-(1-methyl-1H-pyrazol-3-yl)pyridin-3-yl)methyl)-6-(1H-pyrazol-1-yl)picolinamide;

N-((3R,4S)-3-hydroxytetrahydro-2H-pyran-4-yl)-5-methyl-4-(4-(2-methyloxazol-4-yl)benzyl)-6-(1H-pyrazol-1-yl)picolinamide;

N-((1S,2S)-2-hydroxycyclohexyl)-5-methyl-4-((6-(1-methyl-1H-pyrazol-3-yl)pyridin-3-yl)methyl)-6-(1H-pyrazol-1-yl)picolinamide;

N-((1S,2S)-2-hydroxycyclohexyl)-5-methyl-4-((6-(1-methyl-1H-pyrazol-4-yl)pyridin-3-yl)methyl)-6-(1H-pyrazol-1-yl)picolinamide;

N-((1S,2S)-2-hydroxycyclohexyl)-5-methyl-4-(4-(2-methyloxazol-4-yl)benzyl)-6-(1H-pyrazol-1-yl)picolinamide;

5-methyl-4-((6-(1-methyl-1H-pyrazol-3-yl)pyridin-3-yl)methyl)-6-(1H-pyrazol-1-yl)-N-(tetrahydro-2H-pyran-4-yl)picolinamide;

5-methyl-4-((6-(1-methyl-1H-pyrazol-4-yl)pyridin-3-yl)methyl)-6-(1H-pyrazol-1-yl)-N-(tetrahydro-2H-pyran-4-yl)picolinamide;

5-methyl-4-(4-(2-methyloxazol-4-yl)benzyl)-6-(1H-pyrazol-1-yl)-N-(tetrahydro-2H-pyran-4-yl)picolinamide;

N-((1S,2S)-2-hydroxycyclopentyl)-5-methyl-4-((6-(1-methyl-1H-pyrazol-3-yl)pyridin-3-yl)methyl)-6-(1H-pyrazol-1-yl)picolinamide;

N-((1S,2S)-2-hydroxycyclopentyl)-5-methyl-4-((6-(1-methyl-1H-pyrazol-4-yl)pyridin-3-yl)methyl)-6-(1H-pyrazol-1-yl)picolinamide;
N-((1S,2S)-2-hydroxycyclopentyl)-5-methyl-4-(4-(2-methyloxazol-4-yl)benzyl)-6-(1H-pyrazol-1-yl)picolinamide;
4-(4-(1H-pyrazol-1-yl)benzyl)-N-((3R,4S)-3-hydroxytetrahydro-2H-pyran-4-yl)-5-methyl-6-(1-methyl-1H-pyrazol-3-yl)picolinamide;
4-(4-(1H-pyrazol-1-yl)benzyl)-N-((1S,2S)-2-hydroxycyclohexyl)-5-methyl-6-(1-methyl-1H-pyrazol-3-yl)picolinamide;
4-(4-(1H-pyrazol-1-yl)benzyl)-5-methyl-6-(1-methyl-1H-pyrazol-3-yl)-N-(tetrahydro-2H-pyran-4-yl)picolinamide;
4-(4-(1H-pyrazol-1-yl)benzyl)-5-methyl-6-(1-methyl-1H-pyrazol-3-yl)-N-(2-oxaspiro[3.3]heptan-6-yl)picolinamide;
4-(4-(1H-pyrazol-1-yl)benzyl)-N-((1S,2S)-2-hydroxycyclopentyl)-5-methyl-6-(1-methyl-1H-pyrazol-3-yl)picolinamide;
4-(4-(1H-pyrazol-1-yl)benzyl)-N-((1S,2S)-2-hydroxycyclobutyl)-5-methyl-6-(1-methyl-1H-pyrazol-3-yl)picolinamide;
4-(4-(1H-pyrazol-1-yl)benzyl)-5-methyl-6-(1-methyl-1H-pyrazol-3-yl)-N-((tetrahydro-2H-pyran-4-yl)methyl)picolinamide;
(S)-4-(4-(1H-pyrazol-1-yl)benzyl)-5-methyl-6-(1-methyl-1H-pyrazol-3-yl)-N-((tetrahydrofuran-2-yl)methyl)picolinamide;
(R)-4-(4-(1H-pyrazol-1-yl)benzyl)-5-methyl-6-(1-methyl-1H-pyrazol-3-yl)-N-((tetrahydrofuran-2-yl)methyl)picolinamide;
4-(4-(1H-pyrazol-1-yl)benzyl)-N-(3,3-dimethyltetrahydro-2H-pyran-4-yl)-5-methyl-6-(1-methyl-1H-pyrazol-3-yl)picolinamide;
N-((3R,4S)-3-hydroxytetrahydro-2H-pyran-4-yl)-5-methyl-6-(1-methyl-1H-pyrazol-3-yl)-4-((6-methylpyridin-3-yl)methyl)picolinamide;
N-((1S,2S)-2-hydroxycyclohexyl)-5-methyl-6-(1-methyl-1H-pyrazol-3-yl)-4-((6-methylpyridin-3-yl)methyl)picolinamide; and
N-((1S,2S)-2-hydroxycyclopentyl)-5-methyl-6-(1-methyl-1H-pyrazol-3-yl)-4-((6-methylpyridin-3-yl)methyl)picolinamide; or
or a pharmaceutically acceptable salt thereof.

Clause 35. A compound of formula (I),

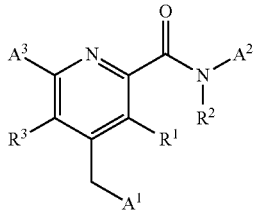

(I)

or a pharmaceutically acceptable salt thereof, wherein
$A^1$ is -Cyc$^2$-Cyc$^3$ or Cyc$^1$;
Cyc$^1$ is a 6-membered heteroaryl;
Cyc$^2$ is a 6-membered aromatic ring optionally containing one nitrogen atom;
Cyc$^3$ is a 5-membered heteroaryl;
wherein Cyc$^1$, Cyc$^2$, and Cyc$^3$ are each independently optionally substituted with 1-5 substituents independently selected from the group consisting of $C_{1-4}$alkyl, halogen, $C_{1-4}$haloalkyl, —O$C_{1-4}$alkyl, —O$C_{1-4}$haloalkyl, OH, oxo, cyano, $C_{3-6}$cycloalkyl, and —$C_{1-3}$alkylene-$C_{3-6}$cycloalkyl, wherein each cycloalkyl is optionally substituted with 1-4 substituents independently selected from halogen and $C_{1-4}$alkyl;
$A^2$ is

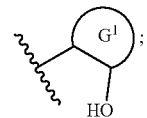

$G^1$ is a 4- to 6-membered saturated alicyclic ring optionally having one carbon ring atom replaced by oxygen;
$A^3$ is a pyrazolyl optionally substituted with $C_{1-4}$alkyl;
$R^1$ is hydrogen;
$R^2$ is hydrogen; and
$R^3$ is $C_{1-4}$alkyl or hydrogen.

Clause 36. The compound of clause 35, or a pharmaceutically acceptable salt thereof, wherein
$A^1$ is -Cyc$^2$-Cyc$^3$;
Cyc$^2$-Cyc$^3$ is

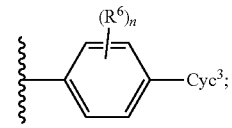

Cyc$^3$ is a pyrazolyl optionally substituted with $C_{1-4}$alkyl;
$R^6$, at each occurrence, is independently selected from the group consisting of halogen, $C_{1-4}$alkyl, $C_{1-4}$haloalkyl, and cyano; and
n is 0, 1, or 2.

Clause 37. The compound of claim 36, or a pharmaceutically acceptable salt thereof, wherein -Cyc$^2$-Cyc$^3$ is

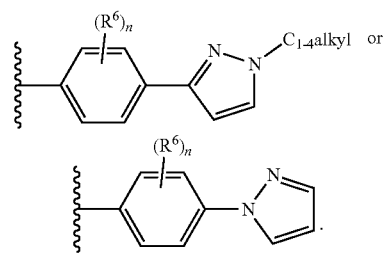

Clause 38. The compound of clause 37, or a pharmaceutically acceptable salt thereof, wherein -Cyc$^2$-Cyc$^3$ is

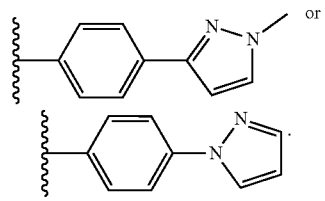

Clause 39. The compound of clause 35, or a pharmaceutically acceptable salt thereof, wherein
A¹ is -Cyc²-Cyc³;
Cyc²-Cyc³ is

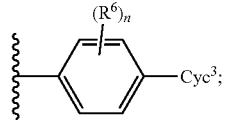

Cyc³ is oxazolyl optionally substituted with $C_{1-4}$alkyl;
R⁶, at each occurrence, is independently selected from the group consisting of halogen, $C_{1-4}$alkyl, $C_{1-4}$haloalkyl, and cyano; and
n is 0, 1, or 2.

Clause 40. The compound of clause 39, or a pharmaceutically acceptable salt thereof, wherein -Cyc²-Cyc³ is

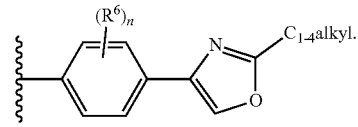

Clause 41. The compound of clause 40, or a pharmaceutically acceptable salt thereof, wherein -Cyc²-Cyc³ is

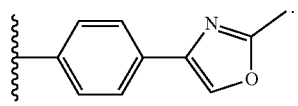

Clause 42. The compound of clause 35, or a pharmaceutically acceptable salt thereof, wherein
A¹ is -Cyc²-Cyc³;
Cyc²-Cyc³ is

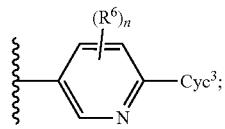

Cyc³ is a pyrazolyl optionally substituted with $C_{1-4}$alkyl;
R⁶, at each occurrence, is independently selected from the group consisting of halogen, $C_{1-4}$alkyl, $C_{1-4}$haloalkyl, and cyano; and
n is 0, 1, or 2.

Clause 43. The compound of clause 42, or a pharmaceutically acceptable salt thereof, wherein -Cyc²-Cyc³ is

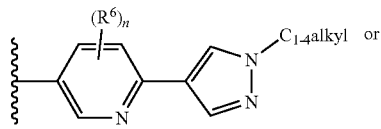

-continued

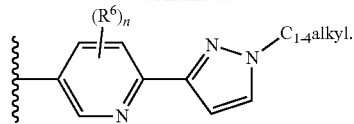

Clause 44. The compound of clause 43, or a pharmaceutically acceptable salt thereof, wherein -Cyc²-Cyc³ is N or N.

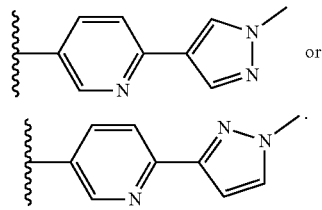

Clause 45. The compound of clause 35, or a pharmaceutically acceptable salt thereof, wherein
A¹ is Cyc¹; and
Cyc¹ is

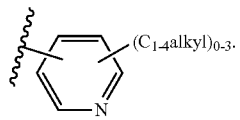

Clause 46. The compound of clause 45, or a pharmaceutically acceptable salt thereof, $C_{1-4}$alkyl wherein Cyc¹ is N

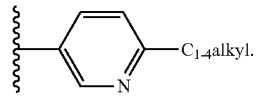

Clause 47. The compound of any of clauses 1-26, 29-33, or 35-46, or a pharmaceutically acceptable salt thereof, wherein
A² is

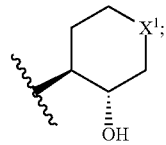

and
X¹ is O or CH₂.

Clause 48. The compound of clause 47, or a pharmaceutically acceptable salt thereof, wherein X¹ is O.

Clause 49. The compound of clause 47, or a pharmaceutically acceptable salt thereof, wherein X¹ is CH₂.

Clause 50. The compound of clause 48, or a pharmaceutically acceptable salt thereof, wherein A³ is

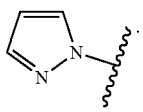

Clause 51. The compound of clause 49, or a pharmaceutically acceptable salt thereof, wherein $A^3$ is

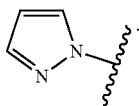

Clause 52. The compound of clause 48, or a pharmaceutically acceptable salt thereof, wherein $A^3$ is

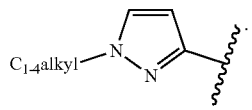

Clause 53. The compound of clause 49, or a pharmaceutically acceptable salt thereof, wherein $A^3$ is

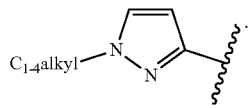

Clause 54. The compound of clause 48, or a pharmaceutically acceptable salt thereof, wherein $A^3$ is

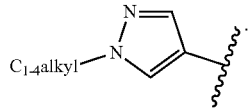

Clause 55. The compound of clause 49, or a pharmaceutically acceptable salt thereof, wherein $A^3$ is

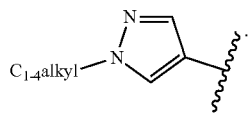

Clause 56. A pharmaceutical composition comprising the compound of any of clauses 1-55, or pharmaceutically acceptable salt thereof, and a pharmaceutically acceptable carrier.

Clause 57. A method for the treatment of a disorder associated with muscarinic acetylcholine receptor activity in a mammal, comprising administering to the mammal an effective amount of the compound of any of clauses 1-55, or a pharmaceutically acceptable salt thereof, or the pharmaceutical composition of clause 56.

Clause 58. The method of clause 57, wherein the mammal is human.

Clause 59. The method of clause 57 or 58, wherein the muscarinic acetylcholine receptor is mAChR M1.

Clause 60. The method of any of clauses 57-59, wherein the mammal has been diagnosed with a need for treatment of the disorder prior to the administering step.

Clause 61. The method of any of clauses 57-60, further comprising the step of identifying a mammal in need of treatment of the disorder.

Clause 62. The method of any of clauses 57-61, wherein the disorder is a neurological disorder or psychiatric disorder, or a combination thereof.

Clause 63. The method of any of clauses 57-61, wherein the disorder is psychosis, schizophrenia, conduct disorder, disruptive behavior disorder, bipolar disorder, psychotic episodes of anxiety, anxiety associated with psychosis, psychotic mood disorders, severe major depressive disorder, mood disorders associated with psychotic disorders, acute mania, depression associated with bipolar disorder, mood disorders associated with schizophrenia, behavioral manifestations of mental retardation, conduct disorder, autistic disorder, movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, or memory disorders, or a combination thereof.

Clause 64. The method of any of clauses 57-61, wherein the disorder is Alzheimer's disease, schizophrenia, a sleep disorder, a pain disorder, or a cognitive disorder, or a combination thereof.

Clause 65. The method of clause 64, wherein the pain disorder is neuropathic pain, central pain syndrome, post-surgical pain syndrome, bone and joint pain, repetitive motion pain, dental pain, cancer pain, myofascial pain, perioperative pain, chronic pain, dysmennorhea, inflammatory pain, headache, migraine headache, cluster headache, headache, primary hyperalgesia, secondary hyperalgesis, primary allodynia, secondary allodynia, or a combination thereof.

What is claimed is:

1. A compound of formula (I),

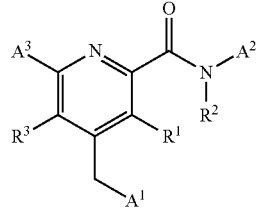

or a pharmaceutically acceptable salt thereof, wherein
$A^1$ is -$Cyc^2$-$Cyc^3$ or $Cyc^1$;
$Cyc^1$ is a 6-membered heteroaryl;
$Cyc^2$ is a 6-membered aromatic ring optionally containing one nitrogen atom;
$Cyc^3$ is a 5-membered heteroaryl;
wherein $Cyc^1$, $Cyc^2$, and $Cyc^3$ are each independently optionally substituted with 1-5 substituents independently selected from the group consisting of $C_{1-4}$alkyl, halogen, $C_{1-4}$haloalkyl, —$OC_{1-4}$alkyl, —$OC_{1-4}$haloalkyl, OH, oxo, cyano, $C_{3-6}$cycloalkyl, and —$C_{1-3}$alkylene-$C_{3-6}$cycloalkyl, wherein each cycloalkyl is optionally substituted with 1-4 substituents independently selected from halogen and $C_{1-4}$alkyl;
$A^2$ is -$L^1$-$G^1$;

$L^1$ is a bond or $CH_2$;

$G^1$ is a monocyclic $C_{3-8}$cycloalkyl, a monocyclic 4- to 8-membered heterocycle containing one oxygen atom, or a 7- to 12-membered spirocyclic heterocycle containing one oxygen atom, wherein $G^1$ is optionally substituted with 1-2 substituents selected from OH and $C_{1-4}$alkyl;

$A^3$ is a pyrazolyl optionally substituted with $C_{1-4}$alkyl;

$R^1$ is hydrogen;

$R^2$ is hydrogen; and $R^3$ is $C_{1-4}$alkyl or hydrogen.

2. The compound of claim 1, or a pharmaceutically acceptable salt thereof, wherein $A^1$ is -Cyc$^2$-Cyc$^3$;

-Cyc$^2$-Cyc$^3$ is

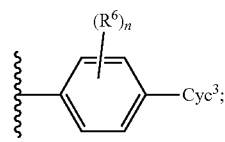

Cyc$^3$ is a pyrazolyl or oxazolyl, each optionally substituted with $C_{1-4}$alkyl;

$R^6$, at each occurrence, is independently selected from the group consisting of halogen, $C_{1-4}$alkyl, $C_{1-4}$haloalkyl, and cyano; and n is 0, 1, or 2.

3. The compound of claim 2, or a pharmaceutically acceptable salt thereof, wherein -Cyc$^2$-Cyc$^3$ is

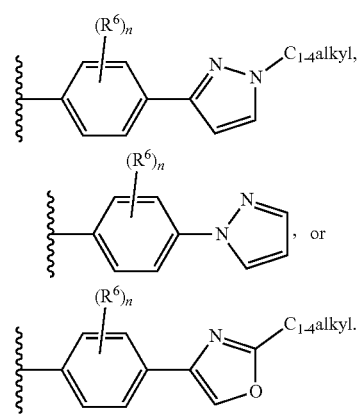

4. The compound of claim 3, or a pharmaceutically acceptable salt thereof, wherein -Cyc$^2$-Cyc$^3$ is

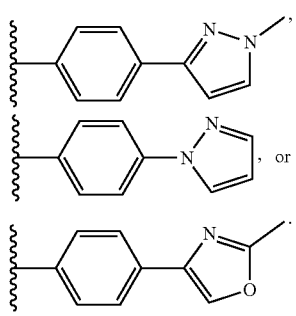

5. The compound of claim 1, or a pharmaceutically acceptable salt thereof, wherein $A^1$ is -Cyc$^2$-Cyc$^3$;

-Cyc$^2$-Cyc$^3$ is

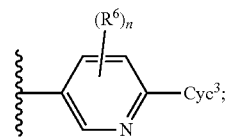

Cyc$^3$ is a pyrazolyl optionally substituted with $C_{1-4}$alkyl;

$R^6$, at each occurrence, is independently selected from the group consisting of halogen, $C_{1-4}$alkyl, $C_{1-4}$haloalkyl, and cyano; and n is 0, 1, or 2.

6. The compound of claim 5, or a pharmaceutically acceptable salt thereof, wherein -Cyc$^2$-Cyc$^3$ is

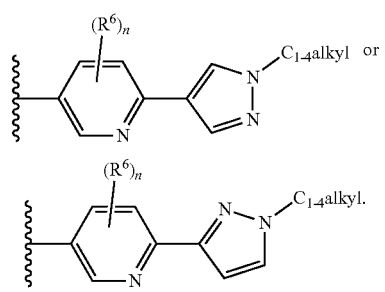

7. The compound of claim 6, or a pharmaceutically acceptable salt thereof, wherein -Cyc$^2$-Cyc$^3$ is

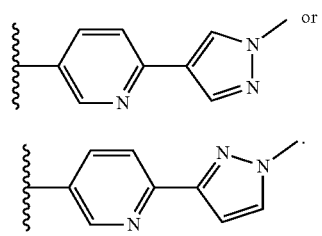

8. The compound of claim 1, or a pharmaceutically acceptable salt thereof, wherein $A^1$ is Cyc$^1$; and Cyc$^1$ is

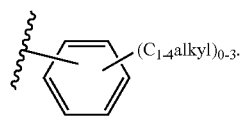

9. The compound of claim 8, or a pharmaceutically acceptable salt thereof, wherein Cyc$^1$ is

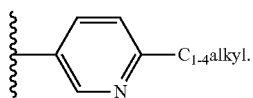

10. The compound of claim 1, or a pharmaceutically acceptable salt thereof, wherein A² is

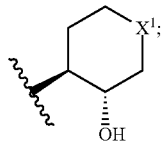

and
X¹ is O or CH₂.

11. The compound of claim 10, or a pharmaceutically acceptable salt thereof, wherein X¹ is O; and A³ is

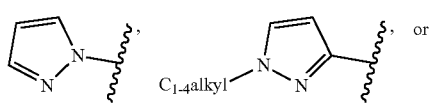

12. The compound of claim 10, or a pharmaceutically acceptable salt thereof, wherein X¹ is CH₂; and A³ is

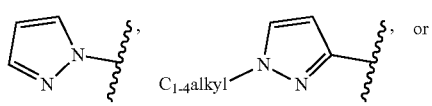

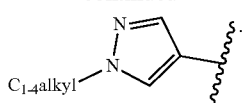

13. The compound of claim 1, or a pharmaceutically acceptable salt thereof, wherein G¹ is

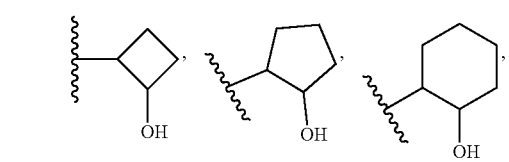

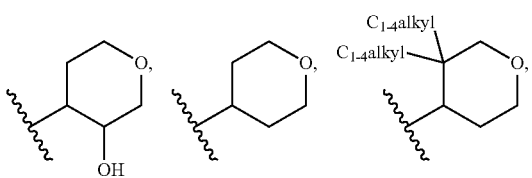

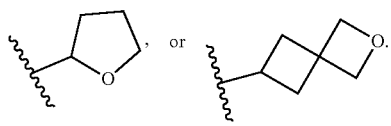

14. The compound of claim 13, or a pharmaceutically acceptable salt thereof, wherein L¹ is a bond.

15. The compound of claim 13, or a pharmaceutically acceptable salt thereof, wherein L¹ is CH₂.

16. The compound of claim 1 selected from the group consisting of

| | |
|---|---|
| 5-methyl-6-(1-methyl-1H-pyrazol-3-yl)-4-(4-(1-methyl-1H-pyrazol-3-yl)benzyl)-N-(tetrahydro-2H-pyran-4-yl)picolinamide | 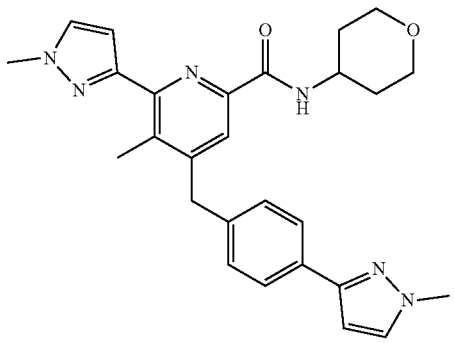 |

N-((3R,4S)-3-hydroxytetrahydro-2H-pyran-4-yl)-5-methyl-4-(4-(1-methyl-1H-pyrazol-3-yl)benzyl)-6-(1H-pyrazol-1-yl)picolinamide;
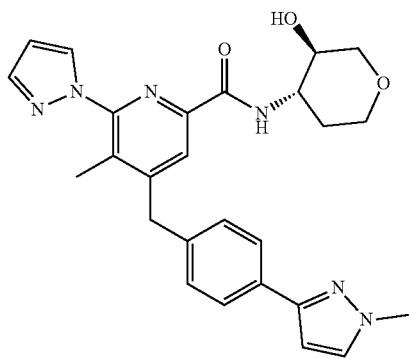 [SMILES: Cc1c(Cc2ccc(-c3ccn(C)n3)cc2)cc(C(=O)N[C@H]2CCOC[C@@H]2O)nc1-n1cccn1]
N-((1S,2S)-2-hydroxycyclohexyl)-6-(1-methyl-1H-pyrazol-3-yl)-4-((6-(1-methyl-1H-pyrazol-4-yl)pyridin-3-yl)methyl)picolinamide
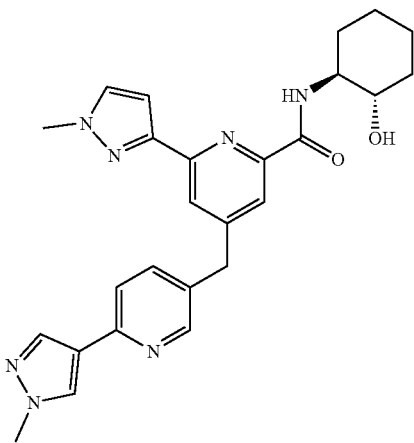 [SMILES: Cn1cc(-c2ccc(Cc3cc(C(=O)N[C@H]4CCCC[C@@H]4O)nc(-c4ccn(C)n4)c3)cn2)cn1]
6-(1-methyl-1H-pyrazol-3-yl)-4-((6-(1-methyl-1H-pyrazol-4-yl)pyridin-3-yl)methyl)-N-(tetrahydro-2H-pyran-4-yl)picolinamide
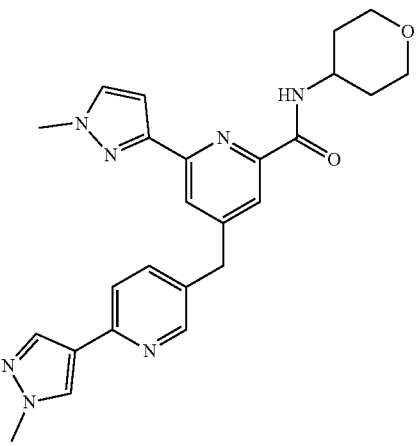 [SMILES: Cn1cc(-c2ccc(Cc3cc(C(=O)NC4CCOCC4)nc(-c4ccn(C)n4)c3)cn2)cn1]

6-(1-methyl-1H-pyrazol-3-yl)-4-((6-(1-methyl-1H-pyrazol-4-yl)pyridin-3-yl)methyl)-N-(2-oxaspiro[3.3]heptan-6-yl)picolinamide
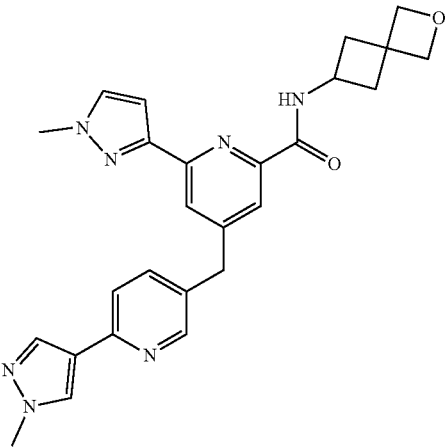 [SMILES: Cn1cc(-c2ccc(Cc3cc(C(=O)NC4CC5(COC5)C4)nc(-c4ccn(C)n4)c3)cn2)cn1]
N-((1S,2S)-2-hydroxycyclopentyl)-6-(1-methyl-1H-pyrazol-3-yl)-4-((6-(1-methyl-1H-pyrazol-4-yl)pyridin-3-yl)methyl)picolinamide
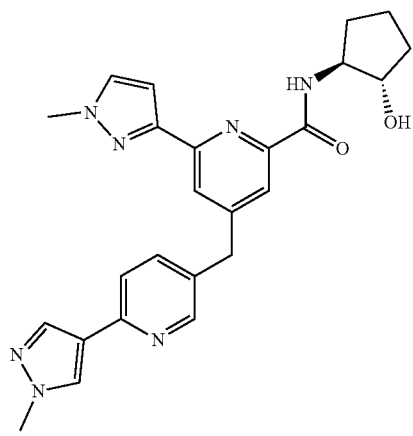 [SMILES: Cn1cc(-c2ccc(Cc3cc(C(=O)N[C@H]4CCC[C@@H]4O)nc(-c4ccn(C)n4)c3)cn2)cn1]
(S)-6-(1-methyl-1H-pyrazol-3-yl)-4-((6-(1-methyl-1H-pyrazol-4-yl)pyridin-3-yl)methyl)-N-((tetrahydrofuran-2-yl)methyl)picolinamide
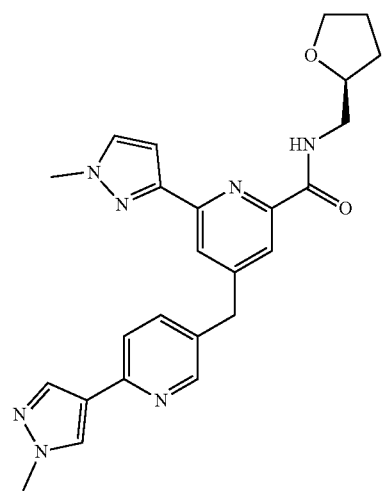 [SMILES: Cn1cc(-c2ccc(Cc3cc(C(=O)NC[C@@H]4CCCO4)nc(-c4ccn(C)n4)c3)cn2)cn1]

N-(3,3-dimethyltetrahydro-2H-pyran-4-yl)-6-(1-methyl-1H-pyrazol-3-yl)-4-((6-(1-methyl-1H-pyrazol-4-yl)pyridin-3-yl)methyl)picolinamide
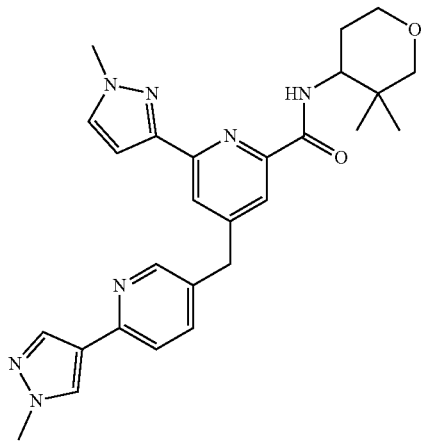 [SMILES: Cn1cc(-c2ccc(Cc3cc(C(=O)NC4CCOCC4(C)C)nc(-c4ccn(C)n4)c3)cn2)cn1]
N-((3R,4S)-3-hydroxytetrahydro-2H-pyran-4-yl)-5-methyl-6-(1-methyl-1H-pyrazol-3-yl)-4-(4-(1-methyl-1H-pyrazol-3-yl)benzyl)picolinamide
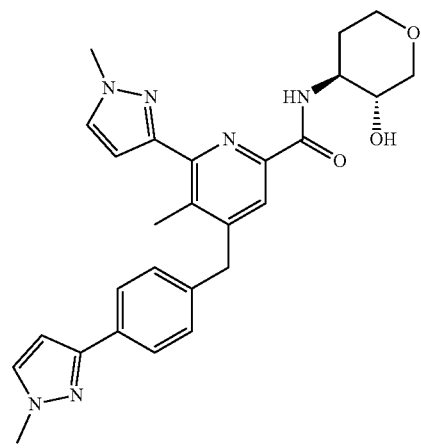 [SMILES: Cc1c(Cc2ccc(-c3ccn(C)n3)cc2)cc(C(=O)N[C@H]2CCOC[C@@H]2O)nc1-c1ccn(C)n1]
N-((1S,2S)-2-hydroxycyclohexyl)-5-methyl-6-(1-methyl-1H-pyrazol-3-yl)-4-(4-(1-methyl-1H-pyrazol-3-yl)benzyl)picolinamide
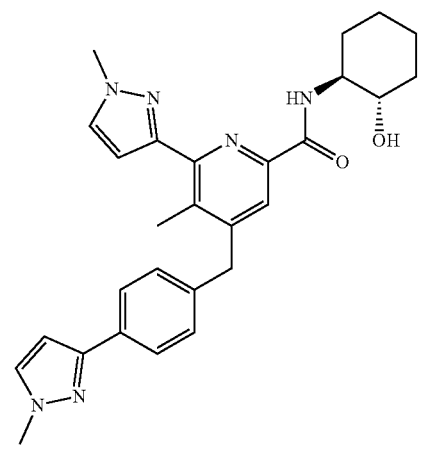 [SMILES: Cc1c(Cc2ccc(-c3ccn(C)n3)cc2)cc(C(=O)N[C@H]2CCCC[C@@H]2O)nc1-c1ccn(C)n1]

5-methyl-6-(1-methyl-1H-pyrazol-3-yl)-4-(4-(1-methyl-1H-pyrazol-3-yl)benzyl)-N-(2-oxaspiro[3.3]heptan-6-yl)picolinamide
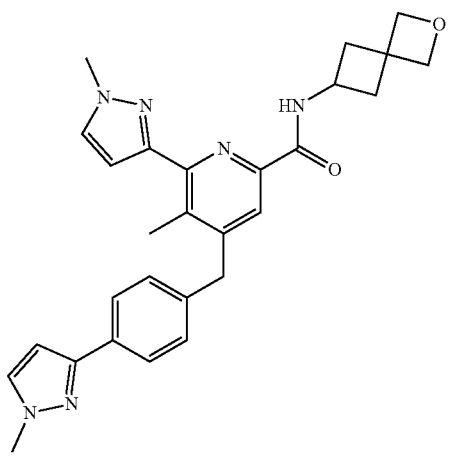 [SMILES: Cc1c(Cc2ccc(-c3ccn(C)n3)cc2)cc(C(=O)NC2CC3(COC3)C2)nc1-c1ccn(C)n1]
N-((1S,2S)-2-hydroxycyclopentyl)-5-methyl-6-(1-methyl-1H-pyrazol-3-yl)-4-(4-(1-methyl-1H-pyrazol-3-yl)benzyl)picolinamide
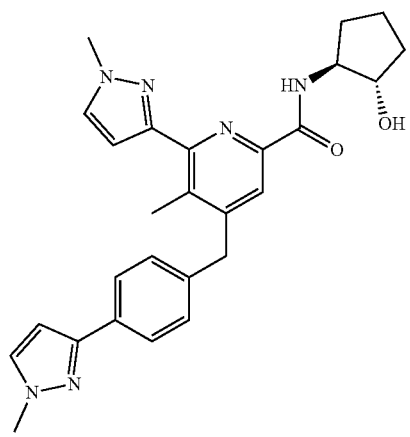 [SMILES: Cc1c(Cc2ccc(-c3ccn(C)n3)cc2)cc(C(=O)N[C@H]2CCC[C@@H]2O)nc1-c1ccn(C)n1]
N-((1S,2S)-2-hydroxycyclobutyl)-5-methyl-6-(1-methyl-1H-pyrazol-3-yl)-4-(4-(1-methyl-1H-pyrazol-3-yl)benzyl)picolinamide
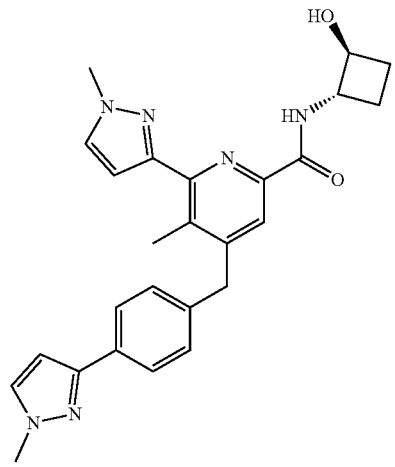 [SMILES: Cc1c(Cc2ccc(-c3ccn(C)n3)cc2)cc(C(=O)N[C@H]2CC[C@@H]2O)nc1-c1ccn(C)n1]

5-methyl-6-(1-methyl-1H-pyrazol-3-yl)-4-(4-(1-methyl-1H-pyrazol-3-yl)benzyl)-N-((tetrahydro-2H-pyran-4-yl)methyl)picolinamide
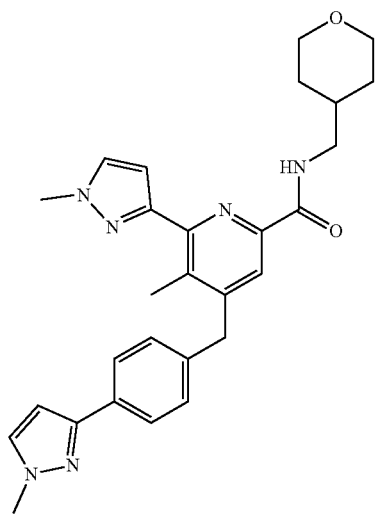 [SMILES: Cc1c(Cc2ccc(-c3ccn(C)n3)cc2)cc(C(=O)NCC2CCOCC2)nc1-c1ccn(C)n1]
(S)-5-methyl-6-(1-methyl-1H-pyrazol-3-yl)-4-(4-(1-methyl-1H-pyrazol-3-yl)benzyl)-N-((tetrahydrofuran-2-yl)methyl)picolinamide
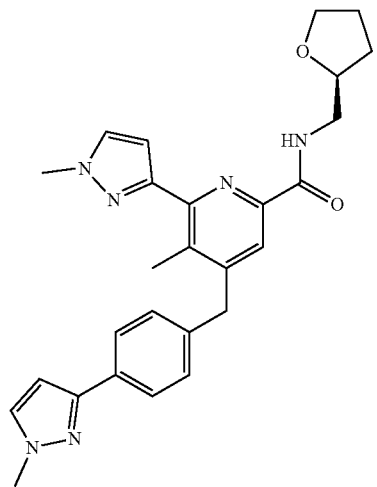 [SMILES: Cc1c(Cc2ccc(-c3ccn(C)n3)cc2)cc(C(=O)NC[C@@H]2CCCO2)nc1-c1ccn(C)n1]
(R)-5-methyl-6-(1-methyl-1H-pyrazol-3-yl)-4-(4-(1-methyl-1H-pyrazol-3-yl)benzyl)-N-((tetrahydrofuran-2-yl)methyl)picolinamide
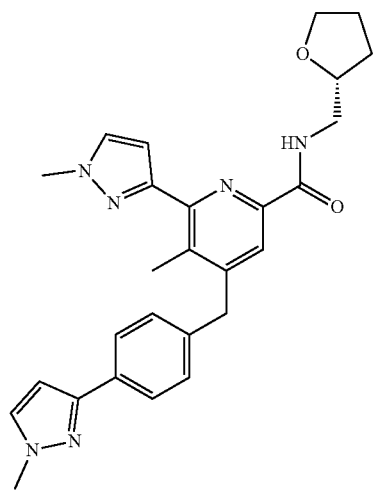 [SMILES: Cc1c(Cc2ccc(-c3ccn(C)n3)cc2)cc(C(=O)NC[C@H]2CCCO2)nc1-c1ccn(C)n1]

N-(3,3-dimethyltetrahydro-2H-pyran-4-yl)-5-methyl-6-(1-methyl-1H-pyrazol-3-yl)-4-(4-(1-methyl-1H-pyrazol-3-yl)benzyl)picolinamide
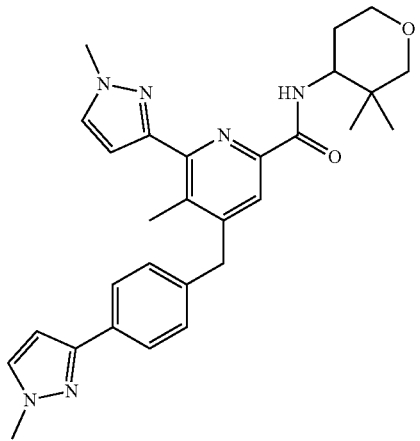 [SMILES: Cc1c(Cc2ccc(-c3ccn(C)n3)cc2)cc(C(=O)NC2CCOCC2(C)C)nc1-c1ccn(C)n1]
N-((3R,4S)-3-hydroxytetrahydro-2H-pyran-4-yl)-4-((6-(1-methyl-1H-pyrazol-4-yl)pyridin-3-yl)methyl)-6-(1H-pyrazol-1-yl)picolinamide
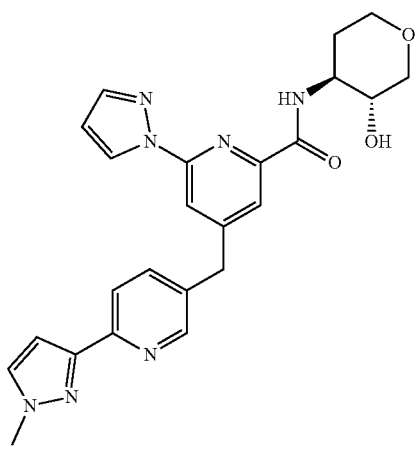 [SMILES: Cn1ccc(-c2ccc(Cc3cc(C(=O)N[C@H]4CCOC[C@@H]4O)nc(-n4cccn4)c3)cn2)n1]
N-((3R,4S)-3-hydroxytetrahydro-2H-pyran-4-yl)-4-(4-(2-methyloxazol-4-yl)benzyl)-6-(1H-pyrazol-1-yl)picolinamide
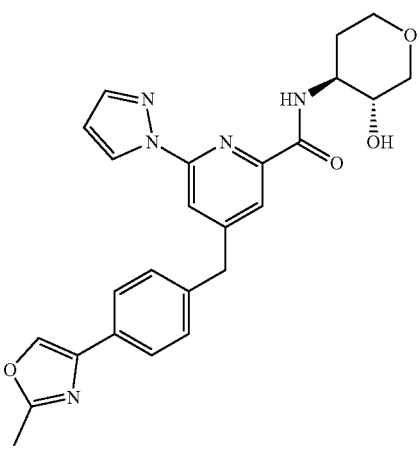 [SMILES: Cc1nc(-c2ccc(Cc3cc(C(=O)N[C@H]4CCOC[C@@H]4O)nc(-n4cccn4)c3)cc2)co1]

N-((1S,2S)-2-hydroxycyclohexyl)-4-((6-(1-methyl-1H-pyrazol-4-yl)pyridin-3-yl)methyl)-6-(1H-pyrazol-1-yl)picolinamide
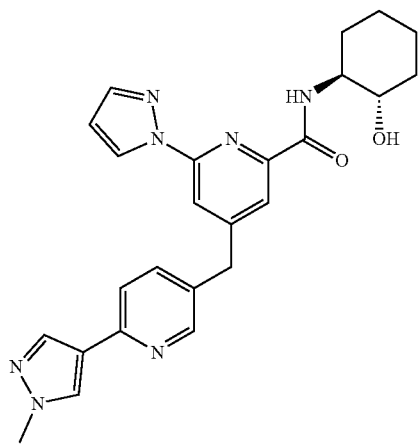 [SMILES: Cn1cc(-c2ccc(Cc3cc(C(=O)N[C@H]4CCCC[C@@H]4O)nc(-n4cccn4)c3)cn2)cn1]
4-((6-(1-methyl-1H-pyrazol-4-yl)pyridin-3-yl)methyl)-6-(1H-pyrazol-1-yl)-N-(2-oxaspiro[3.3]heptan-6-yl)picolinamide
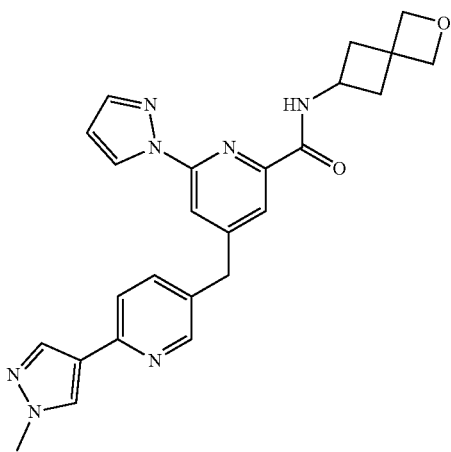
N-((1S,2S)-2-hydroxycyclohexyl)-4-(4-(2-methyloxazol-4-yl)benzyl)-6-(1H-pyrazol-1-yl)picolinamide
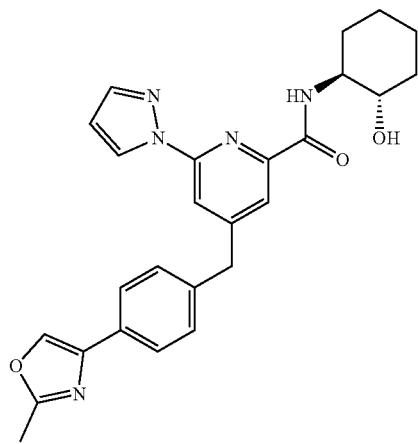 [SMILES: Cc1nc(-c2ccc(Cc3cc(C(=O)N[C@H]4CCCC[C@@H]4O)nc(-n4cccn4)c3)cc2)co1]

| | |
|---|---|
| 4-(4-(2-methyloxazol-4-yl)benzyl)-6-(1H-pyrazol-1-yl)-N-(2-oxaspiro[3.3]heptan-6-yl)picolinamide | 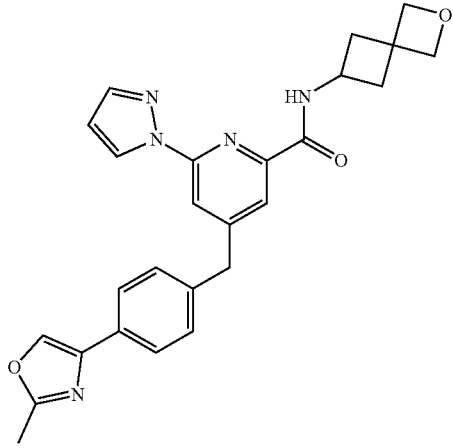 [SMILES: Cc1nc(-c2ccc(Cc3cc(C(=O)NC4CC5(COC5)C4)nc(-n4cccn4)c3)cc2)co1] |
| N-((1S,2S)-2-hydroxycyclopentyl)-4-(4-(2-methyloxazol-4-yl)benzyl)-6-(1H-pyrazol-1-yl)picolinamide | 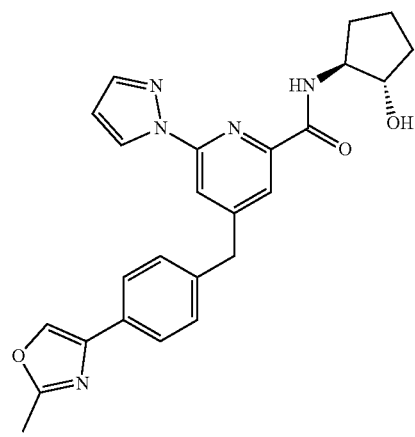 [SMILES: Cc1nc(-c2ccc(Cc3cc(C(=O)N[C@H]4CCC[C@@H]4O)nc(-n4cccn4)c3)cc2)co1] |
| N-((1S,2S)-2-hydroxycyclobutyl)-4-(4-(2-methyloxazol-4-yl)benzyl)-6-(1H-pyrazol-1-yl)picolinamide | 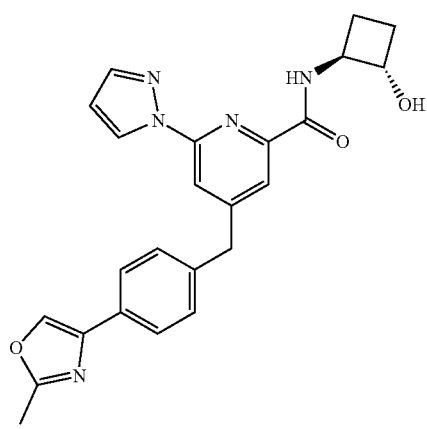 [SMILES: Cc1nc(-c2ccc(Cc3cc(C(=O)N[C@H]4CC[C@@H]4O)nc(-n4cccn4)c3)cc2)co1] |

| | |
|---|---|
| 4-((6-(1-methyl-1H-pyrazol-4-yl)pyridin-3-yl)methyl)-6-(1H-pyrazol-1-yl)-N-(tetrahydro-2H-pyran-4-yl)picolinamide | 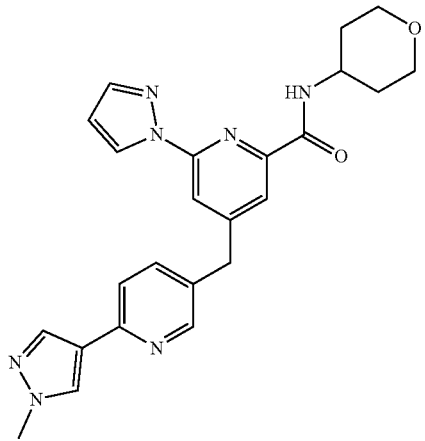 [SMILES: Cn1cc(-c2ccc(Cc3cc(C(=O)NC4CCOCC4)nc(-n4cccn4)c3)cn2)cn1] |
| 4-(4-(2-methyloxazol-4-yl)benzyl)-6-(1H-pyrazol-1-yl)-N-(tetrahydro-2H-pyran-4-yl)picolinamide | 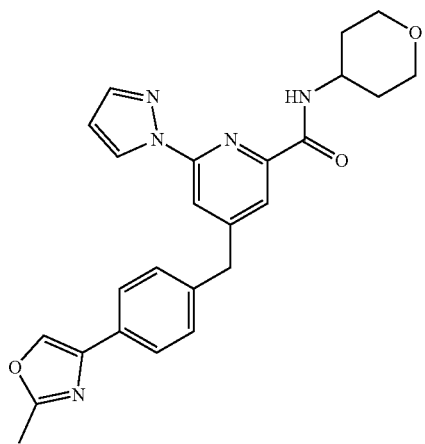 [SMILES: Cc1nc(-c2ccc(Cc3cc(C(=O)NC4CCOCC4)nc(-n4cccn4)c3)cc2)co1] |
| N-((3R,4S)-3-hydroxytetrahydro-2H-pyran-4-yl)-4-(4-(1-methyl-1H-pyrazol-3-yl)benzyl)-6-(1H-pyrazol-1-yl)picolinamide | 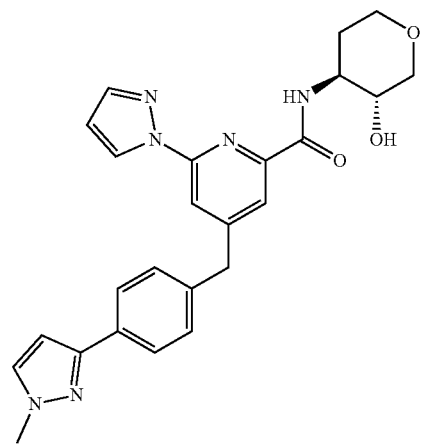 [SMILES: Cn1ccc(-c2ccc(Cc3cc(C(=O)N[C@H]4CCOC[C@@H]4O)nc(-n4cccn4)c3)cc2)n1] |

N-((1S,2S)-2-hydroxycyclohexyl)-4-(4-(1-methyl-1H-pyrazol-3-yl)benzyl)-6-(1H-pyrazol-1-yl)picolinamide
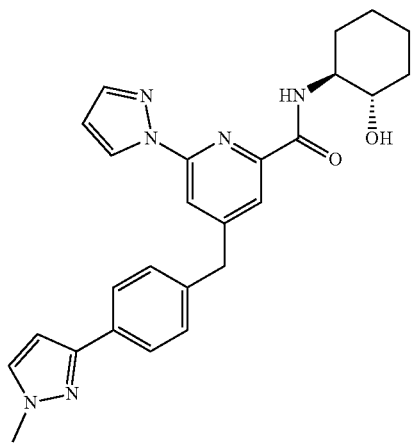 [SMILES: Cn1ccc(-c2ccc(Cc3cc(C(=O)N[C@H]4CCCC[C@@H]4O)nc(-n4cccn4)c3)cc2)n1]
4-(4-(1-methyl-1H-pyrazol-3-yl)benzyl)-6-(1H-pyrazol-1-yl)-N-(tetrahydro-2H-pyran-4-yl)picolinamide
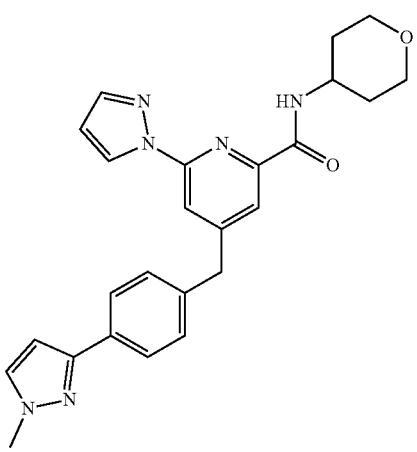 [SMILES: Cn1ccc(-c2ccc(Cc3cc(C(=O)NC4CCOCC4)nc(-n4cccn4)c3)cc2)n1]
4-(4-(1-methyl-1H-pyrazol-3-yl)benzyl)-6-(1H-pyrazol-1-yl)-N-(2-oxaspiro[3.3]heptan-6-yl)picolinamide
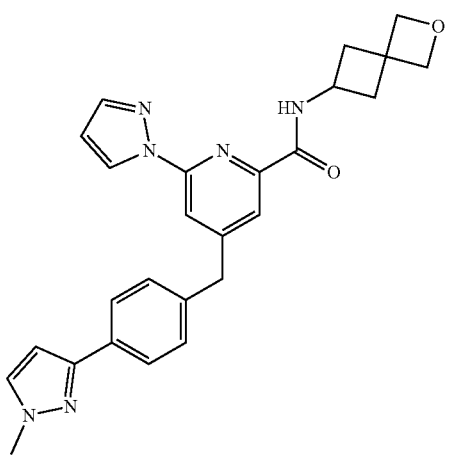 [SMILES: Cn1ccc(-c2ccc(Cc3cc(C(=O)NC4CC5(COC5)C4)nc(-n4cccn4)c3)cc2)n1]

N-((1S,2S)-2-hydroxycyclobutyl)-4-(4-(1-methyl-1H-pyrazol-3-yl)benzyl)-6-(1H-pyrazol-1-yl)picolinamide
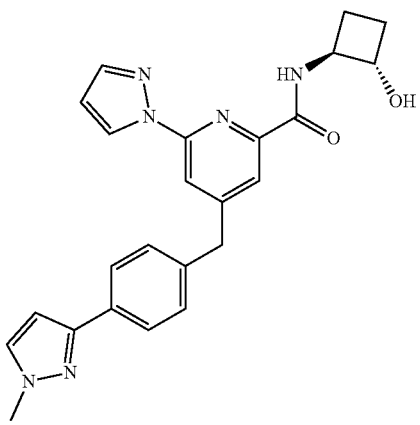 [SMILES: Cn1ccc(-c2ccc(Cc3cc(C(=O)N[C@H]4CC[C@@H]4O)nc(-n4cccn4)c3)cc2)n1]
N-((1S,2S)-2-hydroxycyclopentyl)-4-(4-(1-methyl-1H-pyrazol-3-yl)benzyl)-6-(1H-pyrazol-1-yl)picolinamide
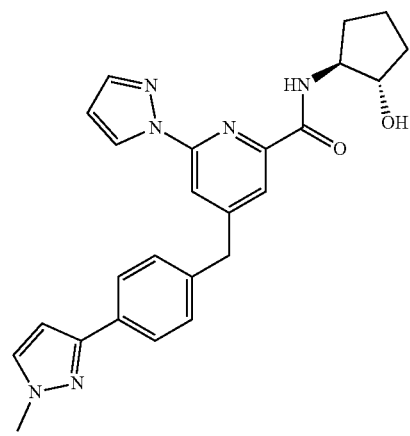 [SMILES: Cn1ccc(-c2ccc(Cc3cc(C(=O)N[C@H]4CCC[C@@H]4O)nc(-n4cccn4)c3)cc2)n1]
N-((1S,2S)-2-hydroxycyclohexyl)-6-(1-methyl-1H-pyrazol-3-yl)-4-(4-(1-methyl-1H-pyrazol-3-yl)benzyl)picolinamide
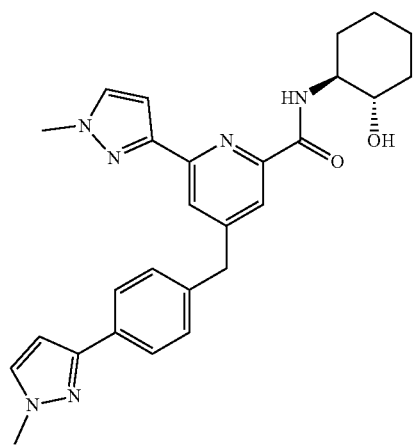 [SMILES: Cn1ccc(-c2ccc(Cc3cc(C(=O)N[C@H]4CCCC[C@@H]4O)nc(-c4ccn(C)n4)c3)cc2)n1]

6-(1-methyl-1H-pyrazol-3-yl)-4-(4-(1-methyl-1H-pyrazol-3-yl)benzyl)-N-(tetrahydro-2H-pyran-4-yl)picolinamide
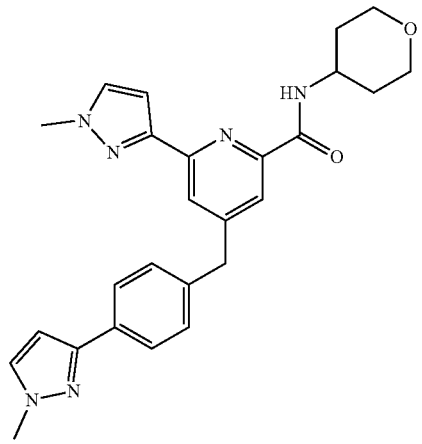 [SMILES: Cn1ccc(-c2ccc(Cc3cc(C(=O)NC4CCOCC4)nc(-c4ccn(C)n4)c3)cc2)n1]
6-(1-methyl-1H-pyrazol-3-yl)-4-(4-(1-methyl-1H-pyrazol-3-yl)benzyl)-N-(2-oxaspiro[3.3]heptan-6-yl)picolinamide
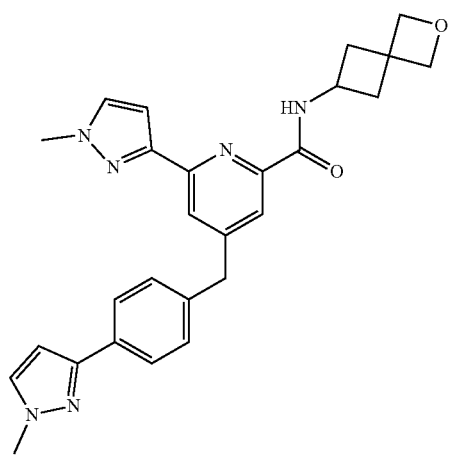 [SMILES: Cn1ccc(-c2ccc(Cc3cc(C(=O)NC4CC5(COC5)C4)nc(-c4ccn(C)n4)c3)cc2)n1]
N-((3R,4S)-3-hydroxytetrahydro-2H-pyran-4-yl)-6-(1-methyl-1H-pyrazol-3-yl)-4-(4-(1-methyl-1H-pyrazol-3-yl)benzyl)picolinamide
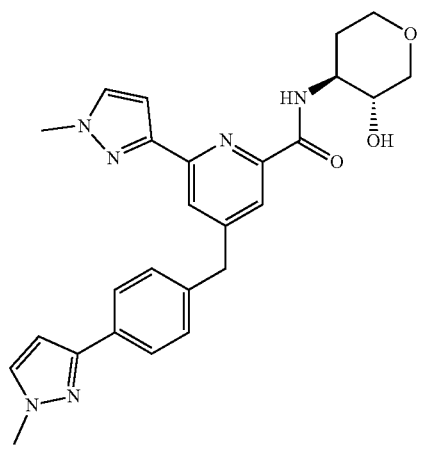 [SMILES: Cn1ccc(-c2ccc(Cc3cc(C(=O)N[C@H]4CCOC[C@@H]4O)nc(-c4ccn(C)n4)c3)cc2)n1]

N-((1S,2S)-2-hydroxycyclopentyl)-6-(1-methyl-1H-pyrazol-3-yl)-4-(4-(1-methyl-1H-pyrazol-3-yl)benzyl)picolinamide
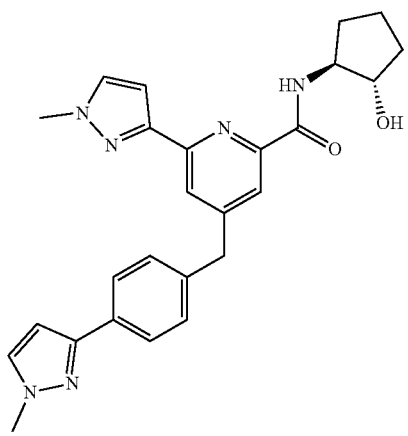 [SMILES: Cn1ccc(-c2ccc(Cc3cc(C(=O)N[C@H]4CCC[C@@H]4O)nc(-c4ccn(C)n4)c3)cc2)n1]
N-((3R,4S)-3-hydroxytetrahydro-2H-pyran-4-yl)-4-(4-(1-methyl-1H-pyrazol-3-yl)benzyl)-6-(1-methyl-1H-pyrazol-4-yl)picolinamide
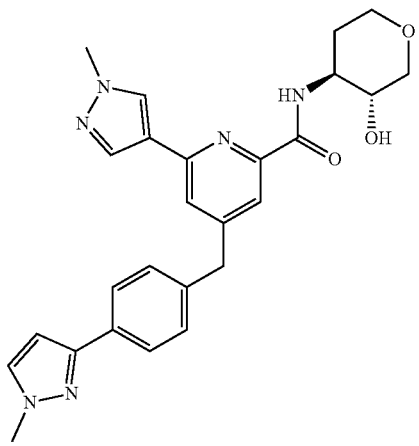 [SMILES: Cn1cc(-c2cc(Cc3ccc(-c4ccn(C)n4)cc3)cc(C(=O)N[C@H]3CCOC[C@@H]3O)n2)cn1]
N-((1S,2S)-2-hydroxycyclohexyl)-4-(4-(1-methyl-1H-pyrazol-3-yl)benzyl)-6-(1-methyl-1H-pyrazol-4-yl)picolinamide
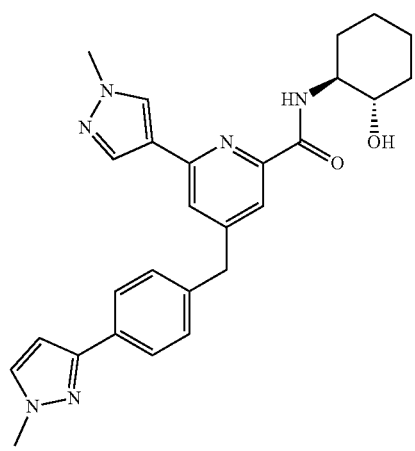 [SMILES: Cn1cc(-c2cc(Cc3ccc(-c4ccn(C)n4)cc3)cc(C(=O)N[C@H]3CCCC[C@@H]3O)n2)cn1]

N-((1S,2S)-2-hydroxycyclohexyl)-5-methyl-4-(4-(1-methyl-1H-pyrazol-3-yl)benzyl)-6-(1H-pyrazol-1-yl)picolinamide
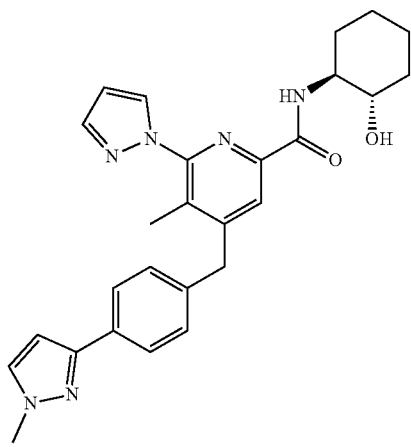 [SMILES: Cc1c(Cc2ccc(-c3ccn(C)n3)cc2)cc(C(=O)N[C@H]2CCCC[C@@H]2O)nc1-n1cccn1]
5-methyl-4-(4-(1-methyl-1H-pyrazol-3-yl)benzyl)-6-(1H-pyrazol-1-yl)-N-(tetrahydro-2H-pyran-4-yl)picolinamide
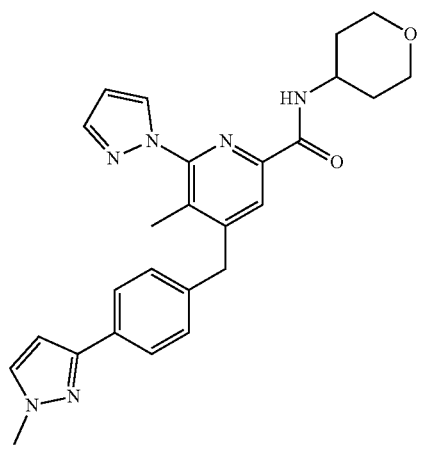 [SMILES: Cc1c(Cc2ccc(-c3ccn(C)n3)cc2)cc(C(=O)NC2CCOCC2)nc1-n1cccn1]
N-((1S,2S)-2-hydroxycyclopentyl)-5-methyl-4-(4-(1-methyl-1H-pyrazol-3-yl)benzyl)-6-(1H-pyrazol-1-yl)picolinamide
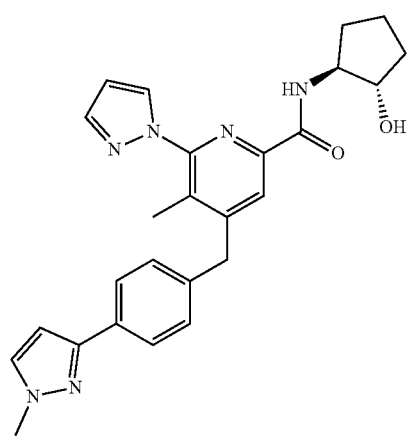 [SMILES: Cc1c(Cc2ccc(-c3ccn(C)n3)cc2)cc(C(=O)N[C@H]2CCC[C@@H]2O)nc1-n1cccn1]

N-((3R,4S)-3-hydroxytetrahydro-2H-pyran-4-yl)-5-methyl-4-((6-(1-methyl-1H-pyrazol-3-yl)pyridin-3-yl)methyl)-6-(1H-pyrazol-1-yl)picolinamide
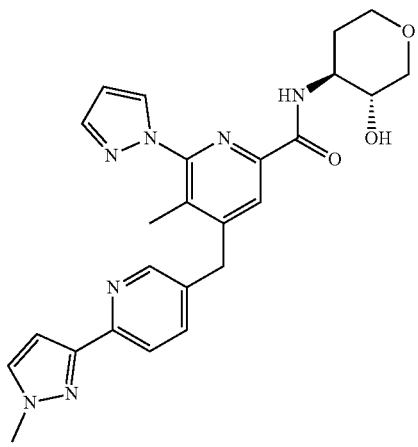 [SMILES: Cc1c(Cc2ccc(-c3ccn(C)n3)nc2)cc(C(=O)N[C@H]2CCOC[C@@H]2O)nc1-n1cccn1]
N-((3R,4S)-3-hydroxytetrahydro-2H-pyran-4-yl)-5-methyl-4-(4-(2-methyloxazol-4-yl)benzyl)-6-(1H-pyrazol-1-yl)picolinamide
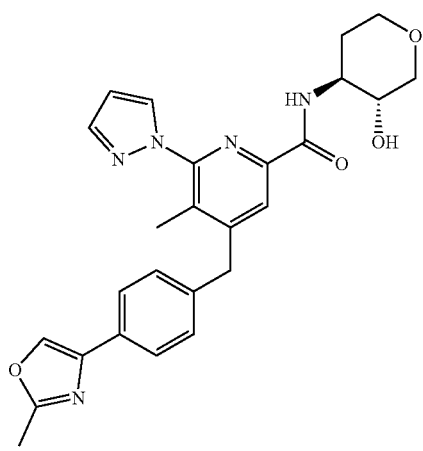 [SMILES: Cc1nc(-c2ccc(Cc3cc(C(=O)N[C@H]4CCOC[C@@H]4O)nc(-n4cccn4)c3C)cc2)co1]
N-((1S,2S)-2-hydroxycyclohexyl)-5-methyl-4-((6-(1-methyl-1H-pyrazol-3-yl)pyridin-3-yl)methyl)-6-(1H-pyrazol-1-yl)picolinamide
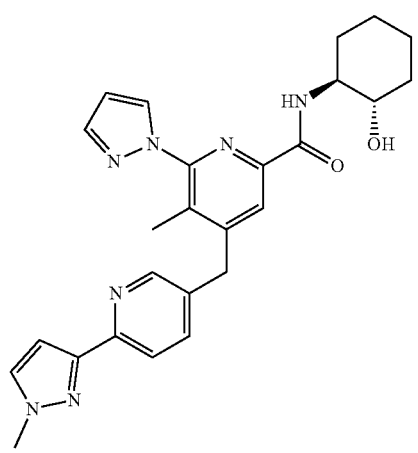 [SMILES: Cc1c(Cc2ccc(-c3ccn(C)n3)nc2)cc(C(=O)N[C@H]2CCCC[C@@H]2O)nc1-n1cccn1]

N-((1S,2S)-2-hydroxycyclohexyl)-5-methyl-4-((6-(1-methyl-1H-pyrazol-4-yl)pyridin-3-yl)methyl)-6-(1H-pyrazol-1-yl)picolinamide
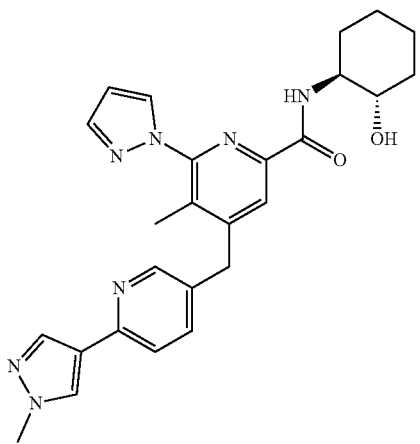 [SMILES: Cc1c(Cc2ccc(-c3cnn(C)c3)nc2)cc(C(=O)N[C@H]2CCCC[C@@H]2O)nc1-n1cccn1]
N-((1S,2S)-2-hydroxycyclohexyl)-5-methyl-4-(4-(2-methyloxazol-4-yl)benzyl)-6-(1H-pyrazol-1-yl)picolinamide
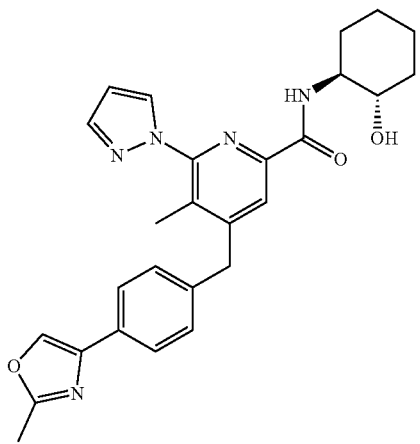 [SMILES: Cc1nc(-c2ccc(Cc3cc(C(=O)N[C@H]4CCCC[C@@H]4O)nc(-n4cccn4)c3C)cc2)co1]
5-methyl-4-((6-(1-methyl-1H-pyrazol-3-yl)pyridin-3-yl)methyl)-6-(1H-pyrazol-1-yl)-N-(tetrahydro-2H-pyran-4-yl)picolinamide
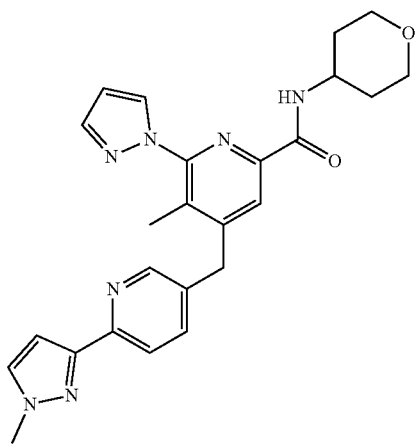 [SMILES: Cc1c(Cc2ccc(-c3ccn(C)n3)nc2)cc(C(=O)NC2CCOCC2)nc1-n1cccn1]

5-methyl-4-((6-(1-methyl-1H-pyrazol-4-yl)pyridin-3-yl)methyl)-6-(1H-pyrazol-1-yl)-N-(tetrahydro-2H-pyran-4-yl)picolinamide
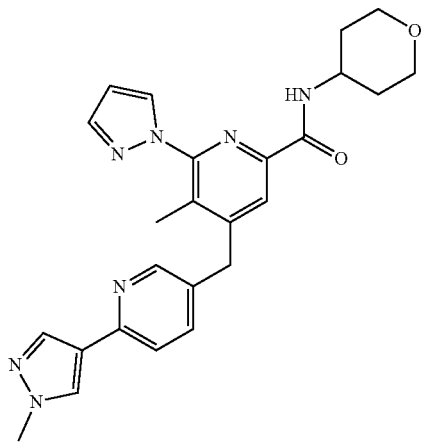 [SMILES: Cc1c(Cc2ccc(-c3cnn(C)c3)nc2)cc(C(=O)NC2CCOCC2)nc1-n1cccn1]
5-methyl-4-(4-(2-methyloxazol-4-yl)benzyl)-6-(1H-pyrazol-1-yl)-N-(tetrahydro-2H-pyran-4-yl)picolinamide
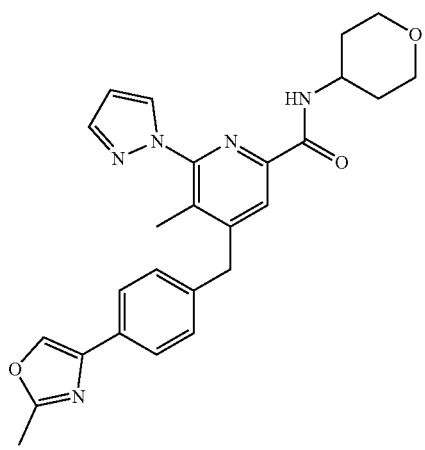 [SMILES: Cc1nc(-c2ccc(Cc3cc(C(=O)NC4CCOCC4)nc(-n4cccn4)c3C)cc2)co1]
N-((1S,2S)-2-hydroxycyclopentyl)-5-methyl-4-((6-(1-methyl-1H-pyrazol-3-yl)pyridin-3-yl)methyl)-6-(1H-pyrazol-1-yl)picolinamide
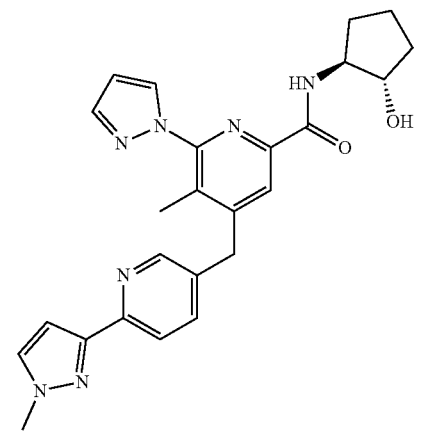 [SMILES: Cc1c(Cc2ccc(-c3ccn(C)n3)nc2)cc(C(=O)N[C@H]2CCC[C@@H]2O)nc1-n1cccn1]

N-((1S,2S)-2-hydroxycyclopentyl)-5-methyl-
4-((6-(1-methyl-1H-pyrazol-4-yl)pyridin-3-
yl)methyl)-6-(1H-pyrazol-1-yl)picolinamide
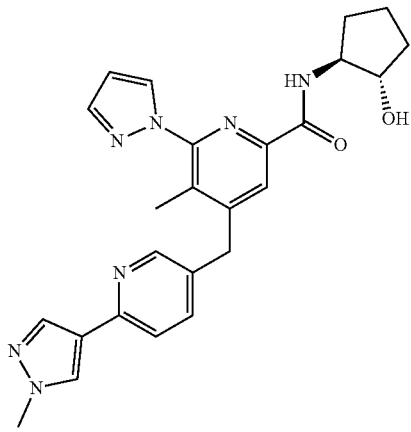
N-((1S,2S)-2-hydroxycyclopentyl)-5-methyl-
4-(4-(2-methyloxazol-4-yl)benzyl)-6-(1H-
pyrazol-1-yl)picolinamide
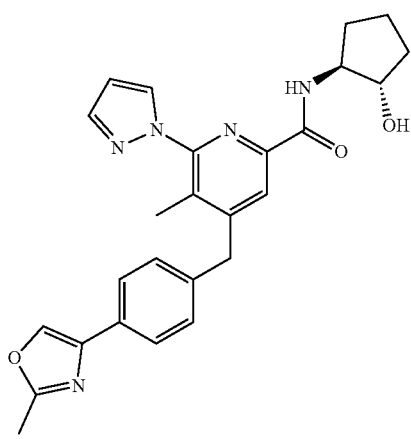 [SMILES: Cc1nc(-c2ccc(Cc3cc(C(=O)N[C@H]4CCC[C@@H]4O)nc(-n4cccn4)c3C)cc2)co1]
4-(4-(1H-pyrazol-1-yl)benzyl)-N-((3R,4S)-3-
hydroxytetrahydro-2H-pyran-4-yl)-5-methyl-
6-(1-methyl-1H-pyrazol-3-yl)picolinamide
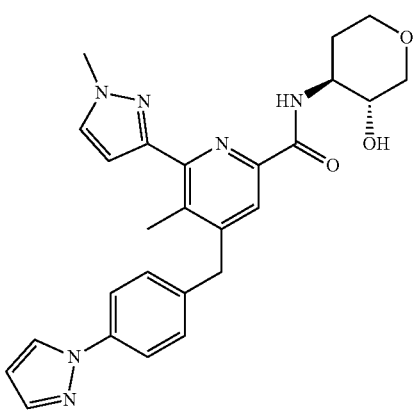 [SMILES: Cc1c(Cc2ccc(-n3cccn3)cc2)cc(C(=O)N[C@H]2CCOC[C@@H]2O)nc1-c1ccn(C)n1]

| | |
|---|---|
| 4-(4-(1H-pyrazol-1-yl)benzyl)-N-((1S,2S)-2-hydroxycyclohexyl)-5-methyl-6-(1-methyl-1H-pyrazol-3-yl)picolinamide | 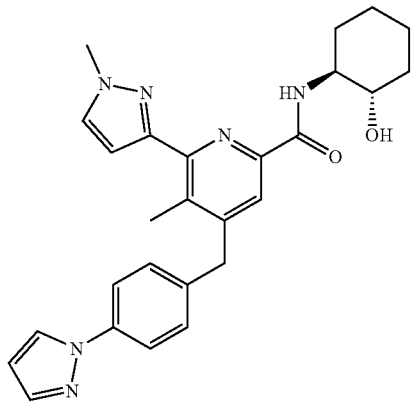 [SMILES: Cc1c(Cc2ccc(-n3cccn3)cc2)cc(C(=O)N[C@H]2CCCC[C@@H]2O)nc1-c1ccn(C)n1] |
| 4-(4-(1H-pyrazol-1-yl)benzyl)-5-methyl-6-(1-methyl-1H-pyrazol-3-yl)-N-(tetrahydro-2H-pyran-4-yl)picolinamide | 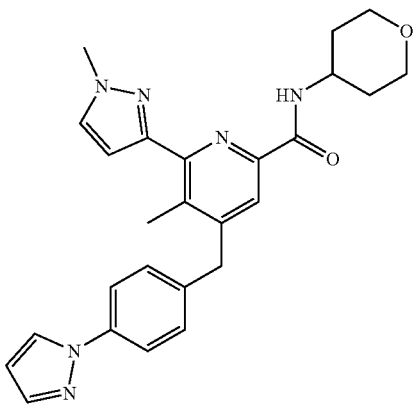 [SMILES: Cc1c(Cc2ccc(-n3cccn3)cc2)cc(C(=O)NC2CCOCC2)nc1-c1ccn(C)n1] |
| 4-(4-(1H-pyrazol-1-yl)benzyl)-5-methyl-6-(1-methyl-1H-pyrazol-3-yl)-N-(2-oxaspiro[3.3]heptan-6-yl)picolinamide | 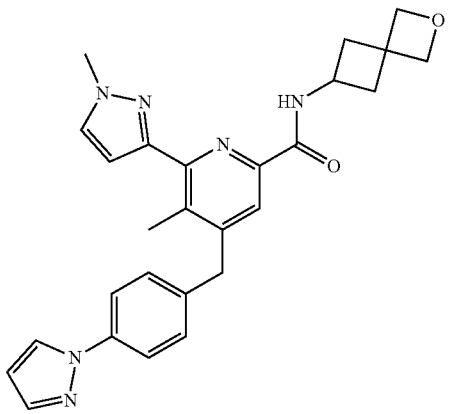 [SMILES: Cc1c(Cc2ccc(-n3cccn3)cc2)cc(C(=O)NC2CC3(COC3)C2)nc1-c1ccn(C)n1] |
| 4-(4-(1H-pyrazol-1-yl)benzyl)-N-((1S,2S)-2-hydroxycyclopentyl)-5-methyl-6-(1-methyl-1H-pyrazol-3-yl)picolinamide | 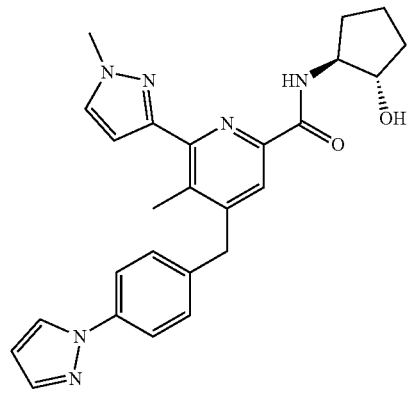 [SMILES: Cc1c(Cc2ccc(-n3cccn3)cc2)cc(C(=O)N[C@H]2CCC[C@@H]2O)nc1-c1ccn(C)n1] |

| | |
|---|---|
| 4-(4-(1H-pyrazol-1-yl)benzyl)-N-((1S,2S)-2-hydroxycyclobutyl)-5-methyl-6-(1-methyl-1H-pyrazol-3-yl)picolinamide | 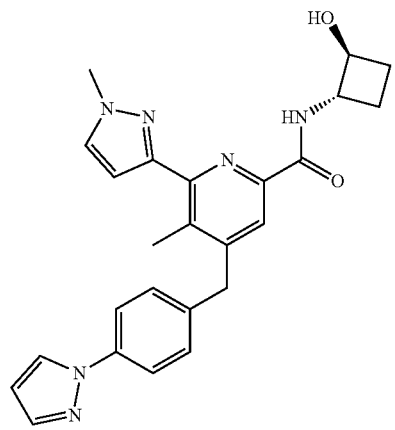 [SMILES: Cc1c(Cc2ccc(-n3cccn3)cc2)cc(C(=O)N[C@H]2CC[C@@H]2O)nc1-c1ccn(C)n1] |
| 4-(4-(1H-pyrazol-1-yl)benzyl)-5-methyl-6-(1-methyl-1H-pyrazol-3-yl)-N-((tetrahydro-2H-pyran-4-yl)methyl)picolinamide | 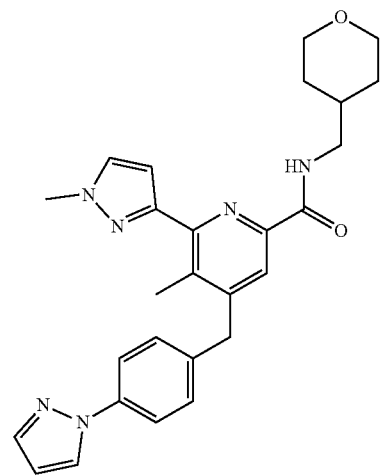 [SMILES: Cc1c(Cc2ccc(-n3cccn3)cc2)cc(C(=O)NCC2CCOCC2)nc1-c1ccn(C)n1] |
| (S)-4-(4-(1H-pyrazol-1-yl)benzyl)-5-methyl-6-(1-methyl-1H-pyrazol-3-yl)-N-((tetrahydrofuran-2-yl)methyl)picolinamide | 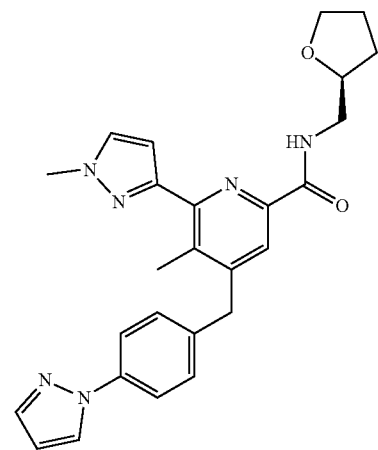 [SMILES: Cc1c(Cc2ccc(-n3cccn3)cc2)cc(C(=O)NC[C@@H]2CCCO2)nc1-c1ccn(C)n1] |

| | |
|---|---|
| (R)-4-(4-(1H-pyrazol-1-yl)benzyl)-5-methyl-6-(1-methyl-1H-pyrazol-3-yl)-N-((tetrahydrofuran-2-yl)methyl)picolinamide | 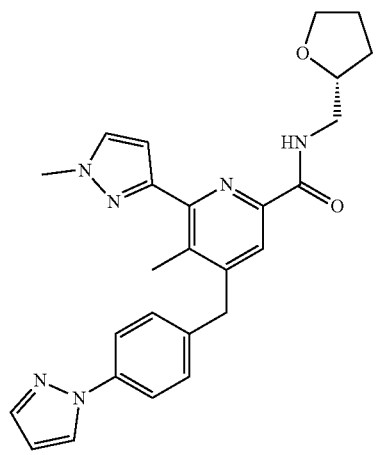 [SMILES: Cc1c(Cc2ccc(-n3cccn3)cc2)cc(C(=O)NC[C@H]2CCCO2)nc1-c1ccn(C)n1] |
| 4-(4-(1H-pyrazol-1-yl)benzyl)-N-(3,3-dimethyltetrahydro-2H-pyran-4-yl)-5-methyl-6-(1-methyl-1H-pyrazol-3-yl)picolinamide | 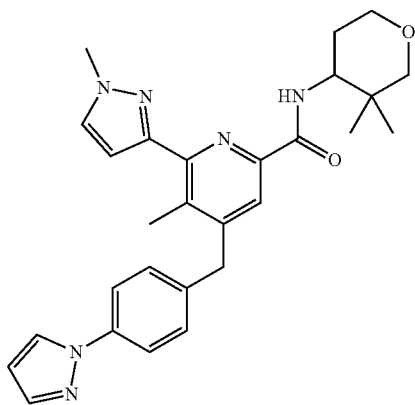 [SMILES: Cc1c(Cc2ccc(-n3cccn3)cc2)cc(C(=O)NC2CCOCC2(C)C)nc1-c1ccn(C)n1] |
| N-((3R,4S)-3-hydroxytetrahydro-2H-pyran-4-yl)-5-methyl-6-(1-methyl-1H-pyrazol-3-yl)-4-((6-methylpyridin-3-yl)methyl)picolinamide | 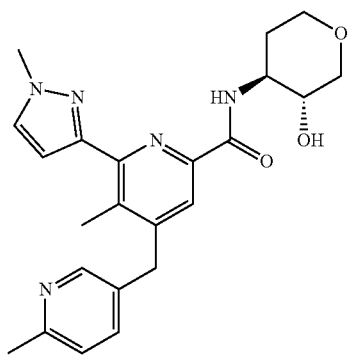 [SMILES: Cc1ccc(Cc2cc(C(=O)N[C@H]3CCOC[C@@H]3O)nc(-c3ccn(C)n3)c2C)cn1] |
| N-((1S,2S)-2-hydroxycyclohexyl)-5-methyl-6-(1-methyl-1H-pyrazol-3-yl)-4-((6-methylpyridin-3-yl)methyl)picolinamide | 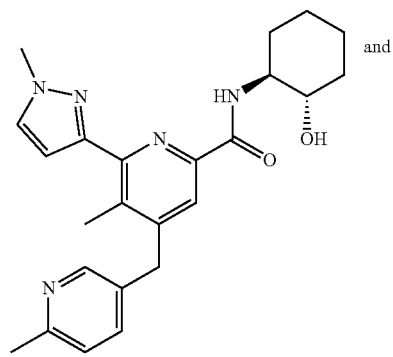 [SMILES: Cc1ccc(Cc2cc(C(=O)N[C@H]3CCCC[C@@H]3O)nc(-c3ccn(C)n3)c2C)cn1] and |

| N-((1S,2S)-2-hydroxycyclopentyl)-5-methyl-6-(1-methyl-1H-pyrazol-3-yl)-4-((6-methylpyridin-3-yl)methyl)picolinamide | 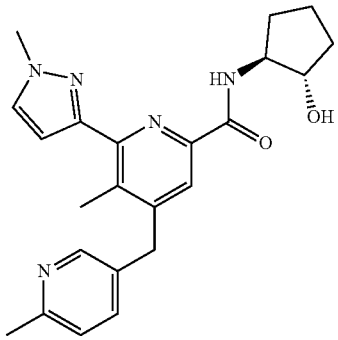 [SMILES: Cc1ccc(Cc2cc(C(=O)N[C@H]3CCC[C@@H]3O)nc(-c3ccn(C)n3)c2C)cn1] | or a pharmaceutically acceptable salt thereof.

17. A pharmaceutical composition comprising the compound of claim 1, or pharmaceutically acceptable salt thereof, and a pharmaceutically acceptable carrier.

18. A method for the treatment of a disorder comprising administering to a subject in need thereof, a therapeutically effective amount of the compound of claim 1, or a pharmaceutically acceptable salt thereof, wherein the disorder is selected from the group consisting of psychosis, schizophrenia, conduct disorder, disruptive behavior disorder, bipolar disorder, psychotic episodes of anxiety, anxiety associated with psychosis, psychotic mood disorders, severe major depressive disorder, mood disorders associated with psychotic disorders, acute mania, depression associated with bipolar disorder, mood disorders associated with schizophrenia, behavioral manifestations of mental retardation, conduct disorder, autistic disorder, movement disorders, Tourette's syndrome, akinetic-rigid syndrome, movement disorders associated with Parkinson's disease, tardive dyskinesia, drug induced and neurodegeneration based dyskinesias, attention deficit hyperactivity disorder, cognitive disorders, dementias, and memory disorders, or a combination thereof.

19. A method for the treatment of a disorder comprising administering to a subject in need thereof, a therapeutically effective amount of the compound of claim 1, or a pharmaceutically acceptable salt thereof, wherein the disorder is selected from the group consisting of Alzheimer's disease, schizophrenia, a sleep disorder, a pain disorder, and a cognitive disorder, or a combination thereof.

20. The method of claim 19, wherein the disorder is neuropathic pain, central pain syndrome, postsurgical pain syndrome, bone and joint pain, repetitive motion pain, dental pain, cancer pain, myofascial pain, perioperative pain, chronic pain, dysmennorhea, inflammatory pain, headache, migraine headache, cluster headache, headache, primary hyperalgesia, secondary hyperalgesia, primary allodynia, or secondary allodynia, or a combination thereof.

* * * * *